(12) United States Patent
Comi et al.

(10) Patent No.: US 11,452,737 B2
(45) Date of Patent: Sep. 27, 2022

(54) COMPOSITIONS AND METHODS FOR TREATING VASCULAR MALFORMATION AND RELATED CONDITIONS

(71) Applicants: THE JOHNS HOPKINS UNIVERSITY, Baltimore, MD (US); DUKE UNIVERSITY, Durham, NC (US); KENNEDY KRIEGER INSTITUTE, INC., Baltimore, MD (US)

(72) Inventors: Anne Comi, Baltimore, MD (US); Jonathan Pevsner, Baltimore, MD (US); Zhenhua Huang, Ellicott City, MD (US); Doug Marchuk, Chapel Hill, NC (US)

(73) Assignees: The Johns Hopkins University, Baltimore, MD (US); Duke University, Durham, NC (US); Kennedy Krieger Institute, Inc., Baltimore, MD (US)

( * ) Notice: Subject to any disclaimer, the term of this patent is extended or adjusted under 35 U.S.C. 154(b) by 286 days.

(21) Appl. No.: 15/750,674

(22) PCT Filed: Jul. 28, 2016

(86) PCT No.: PCT/US2016/044442
§ 371 (c)(1),
(2) Date: Feb. 6, 2018

(87) PCT Pub. No.: WO2017/023687
PCT Pub. Date: Feb. 9, 2017

(65) Prior Publication Data
US 2018/0235994 A1  Aug. 23, 2018

Related U.S. Application Data

(60) Provisional application No. 62/201,859, filed on Aug. 6, 2015, provisional application No. 62/302,035, filed on Mar. 1, 2016.

(51) Int. Cl.
*C12Q 1/6883* (2018.01)
*C12Q 1/6886* (2018.01)
(Continued)

(52) U.S. Cl.
CPC .......... *A61K 31/7076* (2013.01); *A61P 17/00* (2018.01); *A61P 35/00* (2018.01);
(Continued)

(58) Field of Classification Search
CPC ................ C12Q 1/6883; C12Q 1/6886; C12Q 2600/106
See application file for complete search history.

(56) References Cited

U.S. PATENT DOCUMENTS

| | | | |
|---|---|---|---|
| 8,163,546 B2 | 4/2012 | Akamatsu et al. | |
| 8,309,519 B2 | 11/2012 | Li et al. | |

(Continued)

FOREIGN PATENT DOCUMENTS

| | | |
|---|---|---|
| WO | 2014/172434 A1 | 10/2014 |
| WO | 2014172434 A1 | 10/2014 |

OTHER PUBLICATIONS

Amaro, A. et al. European Journal of Cancer 49:3353 (Jul. 2013). (Year: 2013).*

(Continued)

*Primary Examiner* — Diana B Johannsen
(74) *Attorney, Agent, or Firm* — Johns Hopkins Technology Ventures

(57) ABSTRACT

In one aspect, the present invention features a method of inhibiting proliferation and/or reducing survival of a cell comprising a GNAQ polynucleotide or polypeptide having a R183Q or Q209L mutation, comprising contacting the cell with puromycin or a puromycin analog, thereby inhibiting proliferation and/or reducing survival of the cell. In another aspect, a method of treating a vascular malformation or (Continued)

related condition in a subject, comprising administering to the subject an effective amount of puromycin or a puromycin analog is featured. In another aspect, the present invention features a method of identifying a candidate agent that modulates a GNAQ R183Q or Q209L mutation-associated disease, comprising contacting a cell comprising a GNAQ polynucleotide or polypeptide having a R183Q or Q209L mutation with puromycin and a candidate agent and comparing viability of the contacted cell with a reference level of viability, wherein an alteration in viability indicates that the candidate agent modulates the GNAQ R183Q or Q209L mutation-associated disease.

6 Claims, 10 Drawing Sheets

Specification includes a Sequence Listing.

(51) Int. Cl.
    *A61K 31/7076* (2006.01)
    *C12Q 1/68* (2018.01)
    *A61P 17/00* (2006.01)
    *A61P 35/00* (2006.01)

(52) U.S. Cl.
    CPC .............. *C12Q 1/68* (2013.01); *C12Q 1/6883* (2013.01); *C12Q 2600/106* (2013.01); *C12Q 2600/112* (2013.01); *C12Q 2600/118* (2013.01); *C12Q 2600/142* (2013.01); *C12Q 2600/156* (2013.01)

(56) References Cited

U.S. PATENT DOCUMENTS

| | | |
|---|---|---|
| 2009/0069556 A1 | 3/2009 | Gumina et al. |
| 2013/0102653 A1 | 4/2013 | Griewank et al. |
| 2014/0336138 A1 | 11/2014 | Comi et al. |

OTHER PUBLICATIONS

Amaro, A. et al. Supplementary Table 1 of European Journal of Cancer 49:3353 (Jul. 2013). (Year: 2013).*
Van Der Ent, W., et al., "Modeling of human uveal melanoma in zebrafish xenograft embryos", Investigative Ophthalmology & Visual Science, (2014) vol. 55, pp. 6612-6622.
Lyden, D., et al., "Id1 and Id3 are required for neurogenesis, angiogenesis and vascularization of tumour xenografts", Nature (1999) vol. 401, pp. 670-677.
Nakashima, M., et al., "The somatic GNAQ mutation C.548G>A (p.R183Q) is consistently found in Sturge-Weber syndrome", Journal of Human Genetics (2014) vol. 59, pp. 691-693.
Wahl, et al., Molecular hybridization of immobilized nucleic acids: theoretical concepts and practical considerations. Methods Enzymol. 1987;152:399-407.
Kimmel, Identification and characterization of specific clones: strategy for confirming the validity of presumptive clones. Methods Enzymol. 1987;152:507-11.
Benton, et al., Screening lambdagt recombinant clones by hybridization to single plaques in situ. Science. Apr. 8, 1977;196(4286):180-2.
Grunstein, et al., Colony hybridization: A method for the isolation of clofied DNAs that contain a specific gene. Proc Natl Acad Sci U S A. Oct. 1975;72(10):3961-5.
Geronemus, et al., The medical necessity of evaluation and treatment of port-wine stains. J Dermatol Surg Oncol. Jan. 1991;17(1):76-9.
Tallman, et al., Location of port-wine stains and the likelihood of ophthalmic and/or central nervous system complications. Pediatrics. Mar. 1991;87(3):323-7.
Comi, Presentation, diagnosis, pathophysiology, and treatment of the neurological features of Sturge-Weber syndrome. Neurologist. Jul. 2011;17(4):179-84.
Shirley, et al., Sturge-Weber syndrome and port-wine stains caused by somatic mutation in GNAQ. N Engl J Med. May 23, 2013;368(21):1971-9.
Sujansky, et al., Sturge-Weber syndrome: age of onset of seizures and glaucoma and the prognosis for affected children. J Child Neurol. Jan. 1995;10(1):49-58.
Comati, et al.. Upregulation of hypoxia-inducible factor (HIF)-1alpha and HIF-2alpha in leptomeningeal vascular malformations of Sturge-Weber syndrome. J Neuropathol Exp Neurol Jan. 2007;66(1):86-97.
Van De Nes, et al.. Targeted next generation sequencing reveals unique mutation profile of primary melanocytic tumors of the central nervous system. J Neurooncol. May 2016;127(3):435-44.
Van Raamsdonk, et al., Frequent somatic mutations of GNAQ in uveal melanoma and blue naevi. Nature. Jan. 29, 2009;457(7229):599-602.
Thomas, et al.. Mosaic Activating Mutations in GNA11 and GNAQ Are Associated with Phakomatosis Pigmentovascularis and Extensive Dermal Melanocytosis. J Invest Dermatol Apr. 2016;136(4):770-8.
Chan, et al., Genomic copy number analysis of a spectrum of blue nevi identifies recurrent aberrations of entire chromosomal arms in melanoma ex blue nevus. Mod Pathol. Mar. 2016;29(3):227-39.
Laviv, et al., BRAF, GNAQ, and GNA11 mutations and copy number in pediatric low-grade glioma. FEBS Open Bio. 2012; 2: 129-134.
O'Hayre, et al., The emerging mutational landscape of G proteins and G-protein-coupled receptors in cancer. Nat Rev Cancer. Jun. 2013;13(6):412-24.
Amirouchene-Angelozzi, et al., Establishment of novel cell lines recapitulating the genetic landscape of uveal melanoma and preclinical validation of mTOR as a therapeutic target. Mol Oncol. Dec. 2014; 8(8): 1508-1520.
Yu, et al., Mutant Gq/11 promote uveal melanoma tumorigenesis by activating YAP. Cancer Cell. Jun. 16, 2014; 25(6): 822-830.
Bachur, et al., Sturge-Weber Syndrome. Curr Treat Options Neurol. Oct. 2013;15(5):607-17.
Lance, et al., Stimulant Use in Patients with Sturge-Weber Syndrome: Safety and Efficacy. Pediatr Neurol. Nov. 2014;51(5): 675-680.
Di Trapani, et al., Light microscopy and ultrastructural studies of Sturge-Weber disease. Childs Brain. 1982;9(1):23-36.
Couto, et al.. Endothelial Cells from Capillary Malformations are Enriched for Somatic GNAQ Mutations. Plast Reconstr Surg. Jan. 2016; 137(1): 77e-82e.
Nakashima, et al., The somatic GNAQ mutation c.548G>A (p.R183Q) is consistently found in Sturge-Weber syndrome. J Hum Genet. Dec. 2014;59(12):691-3.
Wang, et al., Gq signaling causes glomerular injury by activating TRPC6. J Clin Invest. May 2015;125(5):1913-26.
Singh, et al., Galphaq-TRPC6-mediated Ca2+ entry induces RhoA activation and resultant endothelial cell shape change in response to thrombin. J Biol Chern. Mar. 16, 2007;282(11):7833-43.
Lin, et al., Chronic hypoxia-induced upregulation of store-operated and receptor-operated Ca2+ channels in pulmonary arterial smooth muscle cells: a novel mechanism of hypoxic pulmonary hypertension. Circ Res. Sep. 3, 2004;95(5):496-505.
Fan, et al., TRPC6: an underlying target for human glaucoma. Int J Ophthalmol. 2012; 5(4): 523-526.
Hamdollah Zadeh, et al., VEGF-Mediated Elevated Intracellular Calcium and Angiogenesis in Human Microvascular Endothelial Cells In Vitro Are Inhibited by Dominant Negative TRPC6. Microcirculation. Oct. 2008; 15(7): 605-614.
Koltsova, et al., Transcription factors NFAT2 and Egr1 cooperatively regulate the maturation of T-lymphoma in vitro. Biochemistry (Mosc). Sep. 2007;72(9):954-61.
Divito, et al., Id2, Id3 and Id4 overcome a Smad7-mediated block in tumorigenesis, generating TGF-β-independent melanoma. Carcinogenesis. Apr. 2014; 35(4): 951-958.

(56) References Cited

OTHER PUBLICATIONS

Kim, et al., BMP9 induces EphrinB2 expression in endothelial cells through an Alk1-BMPRII/ActRII-ID1/ID3-dependent pathway: Implications for Hereditary Hemorrhagic Telangiectasia Type II. Angiogenesis. Sep. 2012; 15(3): 497-509.
Sakurai, et al., Crucial role of inhibitor of DNA binding/differentiation in the vascular endothelial growth factor-induced activation and angiogenic processes of human endothelial cells. J Immunol. Nov. 1, 2004;173(9):5801-9.
De Bosscher, et al., The interplay between the glucocorticoid receptor and nuclear factor-kappaB or activator protein-1: molecular mechanisms for gene repression. Endocr Rev. Aug. 2003;24(4):488-522.
Ayroldi, et al., Glucocorticoid-Induced Leucine Zipper Inhibits the Raf-Extracellular Signal-Regulated Kinase Pathway by Binding to Raf-1. Mol Cell Biol. Nov. 2002; 22(22): 7929-7941.
Eddleston, et al., The anti-inflammatory effect of glucocorticoids is mediated by glucocorticoid-induced leucine zipper in epithelial cells. J Allergy Clin Immunol. Jan. 2007;119(1):115-22.
Kelly, et al., Corticosteroid-induced gene expression in allergen-challenged asthmatic subjects taking inhaled budesonide. Br J Pharmacol Mar. 2012;165(6):1737-1747.
Joha, et al., GILZ inhibits the mTORC2/AKT pathway in BCR-ABL(+) cells. Oncogene. Mar. 15, 2012;31(11):1419-30.
Cheng, et al., GILZ overexpression inhibits endothelial cell adhesive function through regulation of NF-κB and MAPK activity. J Immunol. Jul. 1, 2013;191(1):424-33.
Tan, et al., Sustained activation of c-Jun N-terminal and extracellular signal-regulated kinases in port-wine stain blood vessels. J Am Acad Dermatol. Nov. 2014; 71(5): 964-968.
Vural, et al., The expression of vascular endothelial growth factor and its receptors in port-wine stains. Otolaryngol Head Neck Surg. Oct. 2008;139(4):560-4.
Crouch, et al., The use of ATP bioluminescence as a measure of cell proliferation and cytotoxicity. J Immunol Methods. Mar. 15, 1993;160(1):81-8.
Kangas, et al., Bioluminescence of cellular ATP: a new method for evaluating cytotoxic agents in vitro. Med Biol. 1984;62(6):338-43.
Lundin, et al., Estimation of biomass in growing cell lines by adenosine triphosphate assay. Methods Enzymol. 1986;133:27-42.
Petty, et al., Comparison of MTT and ATP-based assays for the measurement of viable cell number. J Biolumin Chemilumin. Jan.-Feb. 1995;10(1):29-34.
Cree, et al., Methotrexate chemosensitivity by ATP luminescence in human leukemia cell lines and in breast cancer primary cultures: comparison of the TCA-100 assay with a clonogenic assay. Anticancer Drugs. Jun. 1995;6(3):398-404.
Cory, et al., Use of an aqueous soluble tetrazolium/formazan assay for cell growth assays in culture. Cancer Commun. Jul. 1991;3(7):207-12.
Barltrop, et al., 5-(3-carboxymethoxyphenyl)-2-(4,5-dimethylthiazolyl)-3-(4-sulfophenyl)tetrazolium, inner salt (MTS) and related analogs of 3-(4,5-dimethylthiazolyl)-2,5-diphenyltetrazolium bromide (MTT) reducing to purple water-soluble formazans As cell-viability indicators. Biorg Med Chem Let. 1991;1(11):611-614.
Paull, et al., The synthesis of XTT: A new tetrazolium reagent that is bioreducible to a water-soluble formazan. J Heterolytic Chem. May 1988;25:911.
Van Der Ent, et al., Modeling of human uveal melanoma in zebrafish xenograft embryos. Invest Ophthalmol Vis Sci. Sep. 23, 2014;55(10):6612-22.
Lyden, et al., Id1 and Id3 are required for neurogenesis, angiogenesis and vascularization of tumour xenografts. Nature. Oct. 14, 1999;401(6754):670-7.
De Mik, et al., Pathophysiology and treatment of focal segmental glomerulosclerosis: the role of animal models. BMC Nephrol. Apr. 1, 2013;14:74.
Norris, et al., Calcineurin triggers reactive/inflammatory processes in astrocytes and is upregulated in aging and Alzheimer's models. J Neurosci. May 4, 2005;25(18):4649-58.
Okamura, et al., A conserved docking motif for CK1 binding controls the nuclear localization of NFAT1. Mol Cell Biol. May 2004;24(10):4184-95.

\* cited by examiner

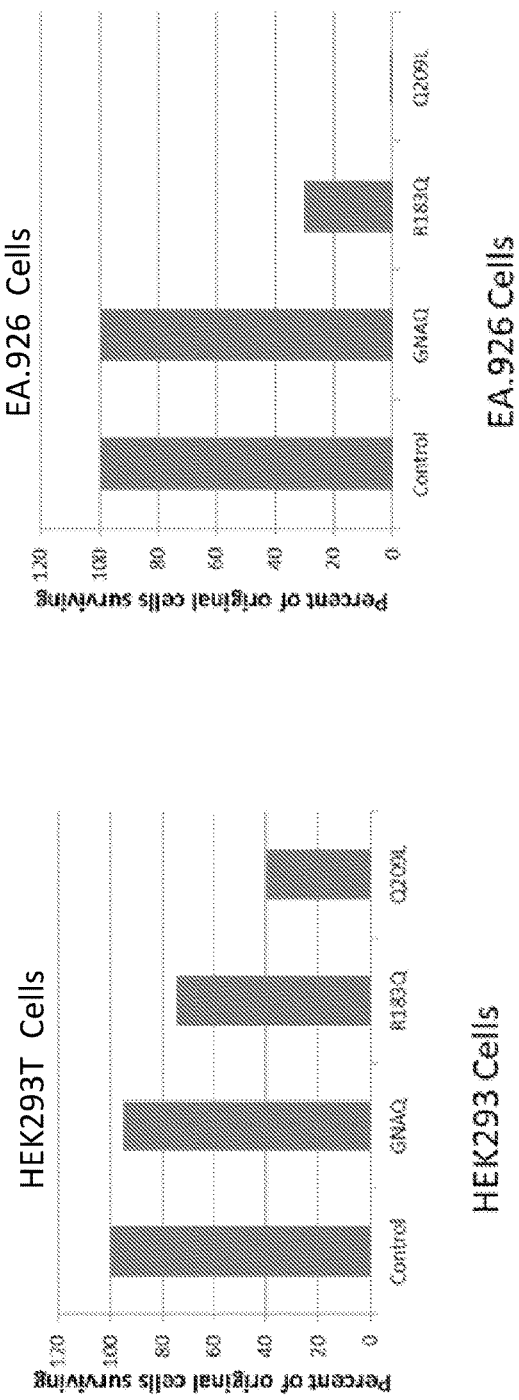
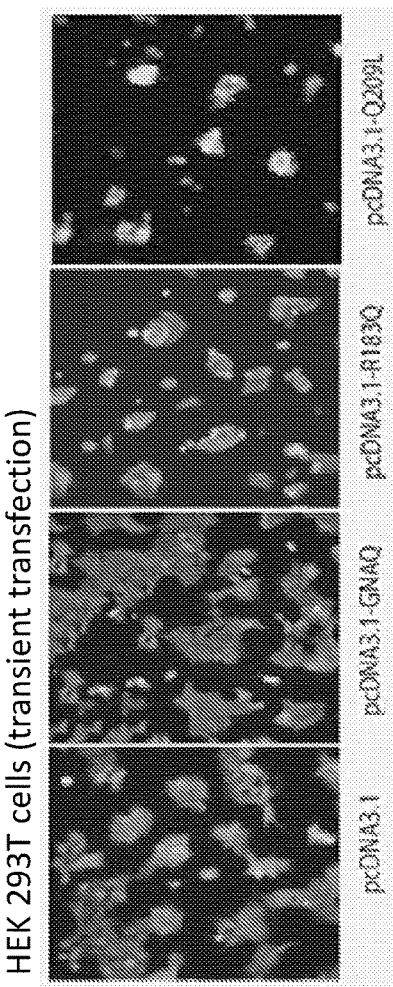
FIG. 2A
FIG. 2B
FIG. 2C
FIG. 2D

COMPOSITIONS AND METHODS FOR TREATING VASCULAR MALFORMATION AND RELATED CONDITIONS

CROSS-REFERENCE TO RELATED APPLICATIONS

This application is a 35 U.S.C. § 371 U.S. national entry of International Application PCT/US2016/044442 having an international filing date of Jul. 28, 2016, which claims the benefit of U.S. Provisional Application No. 62/302,035, filed Mar. 1, 2016 and U.S. Provisional Application No. 62/201,859 filed Aug. 6, 2015, the content of each of the aforementioned applications is herein incorporated by reference in their entirety.

STATEMENT OF GOVERNMENT INTEREST

This invention was made with government support under grant no. UCSF 5842SC U54 awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jul. 27, 2016, is named P13712-03_ST25.txt and is 42,826 bytes in size.

BACKGROUND OF THE INVENTION

Capillary malformations (port-wine birthmarks) occur in about 1 in 300 live births. Sturge-Weber syndrome is the same vascular malformation involving the brain, skin and eye. Patients with Sturge-Weber syndrome are at risk of developing glaucoma, seizures, strokes, and neurological impairment. Current treatments for vascular malformation are primarily symptomatic and inadequate. Thus, new methods of treating vascular malformation are urgently required.

SUMMARY OF THE INVENTION

As described below, the present invention features compositions and methods for treating vascular malformation and related conditions.

In one aspect, the present invention provides a method of inhibiting proliferation and/or reducing survival of a cell containing a GNAQ polynucleotide or polypeptide having a R183Q or Q209L mutation, the method containing the step of contacting the cell with puromycin or a puromycin analog, thereby inhibiting proliferation and/or reducing survival of the cell.

In another aspect, the present invention provides a method of reducing a vascular malformation in a subject, the method containing the step of administering to the subject an effective amount of puromycin or a puromycin analog.

In another aspect, the present invention provides a method of inhibiting progression of a vascular malformation in a subject, the method containing the step of administering to the subject an effective amount of puromycin or a puromycin analog.

In another aspect, the present invention provides a method of reducing appearance of a birthmark in a subject, the method containing the step of administering to the subject an effective amount of puromycin or a puromycin analog.

In another aspect, the present invention provides a method of treating a vascular malformation or related condition in a subject, the method containing the step of administering to the subject an effective amount of puromycin or puromycin analog.

In another aspect, the present invention provides a method of treating a uveal melanoma in a subject, the method containing the step of administering to the subject an effective amount of puromycin or puromycin analog.

In another aspect, the present invention provides a method of treating a disease associated with a R183Q or Q209L mutation in a subject, the method containing the step of administering to the subject an effective amount of puromycin or puromycin analog.

In various embodiments of any aspect delineated herein, the method contains the step of administering puromycin or puromycin analogue in addition to laser treatment to the subject. In various embodiments of any aspect delineated herein, the vascular malformation or related condition is a capillary malformation, vascular malformation in the brain, vascular malformation in the eye, or Sturge-Weber syndrome. In various embodiments of any aspect delineated herein, the puromycin or puromycin analog is administered topically, orally, by injection, or by ocular administration.

In various embodiments of any aspect delineated herein, the subject comprises a GNAQ polynucleotide or polypeptide having a R183Q or Q209L mutation. In various embodiments of any aspect delineated herein, the subject is a human.

In another aspect, the present invention provides a composition comprising a puromycin or puromycin analog formulated for topical administration, ocular administration, oral administration, or administration by injection. In various embodiments, the method according to any other aspect delineated herein contains the step of administering to the subject an effective amount of the composition of any other aspect delineated herein.

In another aspect, the present invention provides a transfected human embryonic kidney (HEK) or endothelial cell containing an isolated polynucleotide encoding a GNAQ polypeptide containing a R183Q or Q209L mutation. In various embodiments of any aspect delineated herein, the cell further contains an isolated polynucleotide encoding a puromycin resistance polypeptide. In various embodiments, the cell is HEK293, HEK293T, EA.926, EA.hy 926, or HUVEC. In various embodiments of any aspect delineated herein, the isolated polynucleotide encoding a GNAQ polypeptide containing a R183Q or Q209L mutation is in a lentivirus plasmid. In various embodiments, the cell is stably transfected or transiently transfected with the isolated polynucleotide encoding a GNAQ polypeptide containing a R183Q or Q209L mutation.

In another aspect, the present invention provides a method of identifying a candidate agent that modulates a GNAQ R183Q or Q209L mutation-associated disease, the method containing the steps of (a) contacting a cell comprising a GNAQ polynucleotide or polypeptide having a R183Q or Q209L mutation with puromycin and a candidate agent; and (b) comparing viability of the contacted cell with a reference level of viability, wherein an alteration in viability indicates that the candidate agent modulates the GNAQ R183Q or Q209L mutation-associated disease.

In another aspect, the present invention provides a method of identifying a candidate agent that modulates a vascular malformation or related condition, the method containing the steps of (a) contacting a cell comprising a GNAQ polynucleotide or polypeptide having a R183Q or Q209L mutation with puromycin and a candidate agent; and (b) comparing viability of the contacted cell with a reference level of viability, where an alteration in viability indicates that the candidate agent modulates a vascular malformation or related condition. In various embodiments, the cell is a cell according to any aspect delineated herein.

In various embodiments of any aspect delineated herein, the alteration in viability is positive or negative. In various embodiments of any aspect delineated herein, the GNAQ R183Q or Q209L mutation-associated disease or the vascular malformation or related condition is a capillary malformation, vascular malformation in the brain, vascular malformation in the eye, or Sturge-Weber syndrome.

In another aspect, the invention provides a method of identifying an agent that modulates a vascular malformation or related condition, the method containing the steps of (a) contacting a cell with a candidate agent; and (b) measuring a level or activity of a ID3, TSC22D3, or TEAD3 polynucleotide or polypeptide, where an alteration in the level or activity of the ID3, TSC22D3, or TEAD3 polynucleotide or polypeptide, indicates that the candidate agent modulates a vascular malformation or related condition.

In various embodiments of any one of the aspects delineated herein, the cell contains a GNAQ polynucleotide or polypeptide containing a R183Q or Q209L mutation. In various embodiments, the cell is a cell of any one of the aspects delineated herein. In some embodiments, the alteration is an increase or decrease in the level or activity of the ID3, TSC22D3, or TEAD3 polynucleotide or polypeptide.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" or "analogue" is meant a molecule that is not identical, but has analogous functional or structural features.

For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. By "puromycin analog" a molecule that is not identical, but has analogous functional or structural features to puromycin. Puromycin analogs include, without limitation, compounds derived from puromycin and having an inhibitory effect on protein translation. Examples of puromycin analogs include, without limitation, $N^6$-bis-demethylpuromycin, (2S)—N-{(1R,2S,4S,5S)-4-[6-(Dimethylamino)purin-9-yl]-1-(hydroxymethyl)bicyclo[3.1.0]hex-2-yl}-2-amino-3-(4-methoxyphenyl)propanamide, (2S)—N-{(1S,3S,4S,5S)-1-[6-(dimethylamino)purin-9-yl]-4-(hydroxymethyl)bicyclo[3.1.0]hex-3-yl}-3-(4-methoxy-phenyl)propanamide, (2S)—N-[(1R,2S,4S,5S)-4-(6-aminopurin-9-yl)-1-(hydroxymethyl)bicyclo[3.1.0]hex-2-yl]-2-amino-3-(4-methoxyphenyl)propanamide, and (2S)—N—R1S,3S,4S,5S)-1-(6-aminopurin-9-yl)-4-(hydroxy-methyl)bicyclo[3.1.0]hexan-3-yl]-2-amino-3-(4-methoxy-phenyl)propanamide.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. By "disease associated with a GNAQ R183Q or Q209Lmutation" or "GNAQ R183Q or Q209L mutation-associated disease" is meant a disease caused by or associated with a R183Q or Q209Lmutation in a GNAQ polynucleotide or polypeptide. Examples of diseases associated with a GNAQ R183Q or Q209L mutation include vascular malformation, capillary malformation, vascular malformation in the brain, vascular malformation in the eye, Sturge-Weber syndrome, and Q209L or R183Q uveal melanoma.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "GNAQ polypeptide" is meant a polypeptide or fragment thereof having at least about 85% or greater amino acid identity to the amino acid sequence provided at NCBI Accession No. NP_002063 and having GNAQ or Gαq biological activity. Exemplary GNAQ or Gαq biological activities include activation of phospholipase C (PLC) and modulation of signaling pathways in a cell. An exemplary GNAQ polypeptide sequence (SEQ ID. NO: 1) is provided below:

```
  1  mtlesimacc lseeakearr indeierqlr rdkrdarrel kllllgtges gkstfikqmr
 61  iihgsgysde dkrgftklvy qniftamqam iramdtlkip ykyehnkaha qlvrevdvek
121  vsafenpyvd aikslwndpg iqecydrrre yqlsdstkyy lndldrvadp aylptqqdvl
181  rvrvpttgii eypfdlqsvi frmvdvggqr serrkwihcf envtsimflv alseydqvlv
241  esdnenrmee skalfrtiit ypwfqnssvi lflnkkdlle ekimyshlvd yfpeydgpqr
301  daqaarefil kmfvdlnpds dkiiyshftc atdtenirfv faavkdtilq lnlkeynlv
```

By "GNAQ polynucleotide" is meant a polynucleotide encoding a GNAQ polypeptide. An exemplary GNAQ polynucleotide sequence is provided at NCBI Accession No. NM_002072 (SEQ ID NO: 2). SEQ ID NO:2 is provided below:

```
   1  agactatccg ctcccaccgc gccccggcc cacctggtgg ccccggccct ggccgccgcc
  61  cccgcggcgg ttcccggagc tcgtcccgga cgcgcgcccg ggcggcgggg gctcggcggc
 121  caccgctgcc tcggggagc gagggcggga gggtgtgtgt gcgcgctgtg agcaggggt
 181  gccggcgggg ctgcagcgga ggcactttgg aagaatgact ctggagtcca tcatggcgtg
 241  ctgcctgagc gaggaggcca aggaagcccg gcggatcaac gacgagatcg agcggcagct
 301  ccgcagggac aagcgggacg cccgccggga gctcaagctg ctgctgctcg gacaggaga
 361  gagtggcaag agtacgttta tcaagcagat gagaatcatc catgggtcag gatactctga
 421  tgaagataaa aggggcttca ccaagctggt gtatcagaac atcttcacgg ccatgcaggc
 481  catgatcaga gccatggaca cactcaagat cccatacaag tatgagcaca ataaggctca
 541  tgcacaatta gttcgagaag ttgatgtgga aaggtgtct gcttttgaga atccatatgt
 601  agatgcaata aagagtttat ggaatgatcc tggaatccag aatgctatg atagacgacg
 661  agaatatcaa ttatctgact ctaccaaata ctatcttaat gacttggacc gcgtagctga
 721  ccctgcctac ctgcctacgc aacaagatgt gcttagagtt cgagtcccca ccacagggat
 781  catcgaatac cctttgact tacaaagtgt cattttcaga atggtcgatg taggggggcca
 841  aagtcagag agaagaaaat ggatacactg ctttgaaaat gtcacctcta tcatgtttct
 901  agtagcgctt agtgaatatg atcaagttct cgtggagtca gacaatgaga accgaatgga
 961  ggaaagcaag gctctcttta gaacaattat cacatacccc tggttccaga actcctcggt
1021  tattctgttc ttaaacaaga aagatcttct agaggagaaa atcatgtatt cccatctagt
1081  cgactacttc ccagaatatg atggacccca gagagatgcc caggcagccc gagaattcat
1141  tctgaagatg ttcgtggacc tgaacccaga cagtgacaaa attatctact cccacttcac
1201  gtgcgccaca gacaccgaga atatccgctt tgtctttgct gccgtcaagg acaccatcct
1261  ccagttgaac ctgaaggagt acaatctggt ctaattgtgc ctcctagaca cccgccctgc
1321  ccttccctgg tgggctattg aagatacaca agagggactg tatttctgtg gaaaacaatt
1381  tgcataatac taatttattg ccgtcctgga ctctgtgtga gcgtgtccac agagtttgta
```

-continued

```
1441  gtaaatatta tgattttatt taaactattc agaggaaaaa cagaggatgc tgaagtacag
1501  tcccagcaca tttcctctct atcttttttt taggcaaaac cttgtgactc agtgtatttt
1561  aaattctcag tcatgcactc acaaagataa gacttgtttc tttctgtctc tctctctttt
1621  tcttttctat ggagcaaaac aaagctgatt tcccttttt cttcccccgc taattcatac
1681  ctccctcctg atgttttcc caggttacaa tggcctttat cctagttcca ttcttggtca
1741  agttttctc tcaaatgata cagtcaggac acatcgttcg atttaagcca tcatcagctt
1801  aatttaagtt tgtagttttt gctgaaggat tatatgtatt aatacttacg gttttaaatg
1861  tgttgctttg gatacacaca tagtttcttt tttaatagaa tatactgtct tgtctcactt
1921  tggactggga cagtggatgc ccatctaaaa gttaagtgtc atttctttta gatgtttacc
1981  ttcagccata gcttgattgc tcagagaaat atgcagaagg caggatcaaa gacacacagg
2041  agtcctttct tttgaaatgc cacgtgccat tgtctttcct cccttctttg cttcttttc
2101  ttaccctctc tttcaattgc agatgccaaa aaagatgcca acagacacta cattaccca
2161  atggctgcta cccagaacct tttataggt tgttcttaat ttttttgttg ttgttgttca
2221  agcttttcct ttctttttt tcttggtgtt tgggccacga ttttaaaatg acttttatta
2281  tgggtatgtg ttgccaaagc tggcttttg tcaaataaaa tgaatacgaa cttaaaaaat
2341  aaaagctggt atcttaaaat gtaagagagt aagactgtga agcctaaaat gactggctga
2401  gaatgaacca gaaatgccat tgccaaaca gttgtaacta gaaatttgat tctcacggtc
2461  cattcttttc tttgtcctta agatgacatt gttagtgttc acgtcccatg ttcagtgtcc
2521  aaaccggcaa tgtaaaaagt atcctgtgtg gtttaacagg aaatctgttt atgtctcttt
2581  atttgaaacc agttttactc tcagtggttc tttaagttca atgaagtctg ccaggaacat
2641  tggttggtag tattattccg acacctttaa tttccaaaat ctgaagttcc tgctagttta
2701  ccaccttcat gatcttcttg aactggtaac tgattaggtt gaacttatgg aagatttgtg
2761  gacttaactc aaaagtaacc tctcagtgtt ctatagaaca tgtatttgtg taactgaacc
2821  taccaggaga aatgtttgga attctatatg tgcaatttt caacaaatgc aaaaaaaata
2881  cagcacatgt attgacaagc ttctgtcaag cagcttgagt tgaaatttga tttaagaaaa
2941  taaatcatga ttgttcaaag ctgctgggac gttagaatta ggccatgata ctggtctcat
3001  tttaactaca gtggtatttg gcactagtgt aaacttccat ataaatcact cttttggaac
3061  aacaaagggg gagggagaaa aatcacggcc tgttaaatga gtaccaaagc cgcccaacag
3121  taatgagatg ttctcatcct tgattctccc agcctcaaac aacacagctt acttttttt
3181  tcccttgctc agaaagtacc tgtaatttaa caaacagact gcctgtaggt atagtgcaat
3241  tacaaatgct ctaatcattg tacatacatc tctcttgata ttgcagcatc catactggct
3301  ttgtaatcat taatttttg gcagattgaa tgtgctgtat tgatatgtat ctatgtaatt
3361  gtattgtatg tctatagcta attcacgttt tgaataatgt tatttattt acttttttaa
3421  gagaggagaa tgtaaatttg tcagtttatt tctgactagg gatattttct ttccatttag
3481  aaaagaagaa aaaaaaaaaa ccttactgtc atacagagcg tactagcgt cgtgctgtat
3541  aaaatcattt gcacattcct gagtagaggt atactgatta taagacccaa aggtaatttc
3601  atagcaaaat acataaaatc agtcggagct tttatacaaa catggaaacc aactttgtag
3661  aacttttgcc atttgatcta ggattggaat atgagctttt atacaattca tattcttatt
3721  tggcaaatgc acagtttagt attacctctc tgatggcctt tactagaaag gcagttttag
3781  aagctattgt gatccactaa ggaaatgttt taacagctag agaccactgc ttgcctgaaa
3841  gggcgttctt aaatttggtg cagcaaaaaa aaaaaaaaaa aaaaaaaaaa ttaaacaaca
```

-continued

```
3901  acatttgaag gcctacagtg tgtatagaga aaacctcatc acaagatcat aagtgttaca
3961  gttttaggga atcaagatat tctatttaat agagctatag taaatgtagt caattaaacc
4021  tgatctcaaa gcttgaagaa gctgagcaaa acagggaaag attgttatat ttgtctttat
4081  gaaattggga tggaatttgc tatgcagaat tgaggtttgt ggcttcgctg ttcctgtagg
4141  gtgcatgaca agatcccttc tcttgagaaa ggaaaaaatt gatcaccta gcagcagtga
4201  tgcatagaaa cctaatttta gccacaccag tcaatcgaag ctaaaggatt ttcttttttg
4261  tttcttcggg gttttattga aggggctagg ggcgggacgg gattcttttc agttttgtat
4321  aaaaacaaag tttactcatg ctttatatta tattgtgatt gcaagcgtta taagcgtgtg
4381  ccactggcct cctattgttg atgcttaggt aatggaggcc tgtggtgagt tttatggtga
4441  cttgggcatg tcttattcaa aaacaaaaac ataaaacaca gaaacctttc ttcagcatac
4501  caaggcaagc agccatttca tgactcactt aacacattgc agtgtaccag tttacagatg
4561  attttcccct ttttgcgtga catggcagtt ctaaccccca gagaattcct tatttgtaaa
4621  ttggaagttt ctactatgcc ttacagagct taaattcaga agtttgtgcc tcatatctga
4681  aacaaaggga ataacacac ccattcaaaa gtaaataaat ctcctagaag tttttgtttt
4741  taacatttcc atataaagag ctctgttgaa tgtcatgaat agactggaaa aaaaaatttt
4801  aagaacctgc atatgttgtt tactagcaga tgacaactac aaaaggaatc tgaagaacac
4861  gtaaaacttg tatttttttt tttttggtag attaactagc aggcctattt taaaaaggta
4921  attcagctaa agggcaattt acttttttgt acttcagact atcttgattg tcaaagtgta
4981  cgaactgtaa ttttaaaatt tatactgcca catgattgta aattttagtt gtcttaagtt
5041  aggaattggt gaaaagctat ttatgctgga tttgggtcaa aatgacttat ttgcaaaaaa
5101  ataataatg ggaagaaagg gctgtataat gaaatactgc aagactcaca tattggttgg
5161  aaatttccct caaatcacct accgattacc cttgattcc ctttgttttc agtttctcaa
5221  aacgaatgaa atgaaatata gcagaatgtt aacccatata aaaataaagt gtacccaaat
5281  attgtaatgt atattgctgc tcttcttcaa attaaataag ggtttaaaac cacttaattg
5341  gtaatcaaca tctcaattga tacaaataag gtgtgcttgg tatacattaa tatttcttc
5401  caaagatata tctttggtta gaaacacaaa aaaataaaac tagtaatatt gtatgtttat
5461  ctatctctac atatttccag catatgtagc gttaatagat ctgtcctggt aactgtgtct
5521  ttgggatttc attttggttc catcaaatta ggaaaagaaa tggcttagtt gtatatgatt
5581  agctagagat ttttggagcc agacacctgc tgtttagtag ataacttagt acagacccta
5641  aacttgtcat ttgttttct cacagaatag ccatttcctg ctgtcttccc aatgatcact
5701  gcccttcca taacactctt gcctctagaa tcatatgttc aaagtatgaa tacacaccta
5761  gcacatagta ggtgctcaaa tattaatttc ctccttgcct tccttatcta ccctgtgtcc
5821  tccatttccc cgtatgattc caacccaata tagcaaatga catttacatg ttatgaaaac
5881  atctattggg taaaatcaga tcttggataa agaaattctg acttttatat aagcttttgg
5941  tagacagaaa aaacagaaag gtattcgttg gtagaacatt tttaagttca ggaaagaaag
6001  ctggaataat actacgtaac tttgtccagg ttactttgac tgaaacacgt ttttggtgga
6061  tttctttcc tcaaagaact ctctaaatgc aactccttgc tggattcctc acccatcatc
6121  ctgttggaaa ccccttactag acctatgtat ttagggagtt ttgtcagaaa acatttttaa
6181  cttgcagtat ttaaaagaat atttactgtt cctaaaatgt cattcaaatg catgtactgt
```

```
6241   ctattgtttg gggatgggaa ctagttttgc aaaaaacacc taatgttgta taataatgcc 6301   ccaatgatct tgctggttaa aaatacagta tttttggcca taa
```

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "ID3 polypeptide" is meant a polypeptide or fragment thereof having at least about 85% or greater amino acid identity to the amino acid sequence provided at NCBI Accession No. NP_002158.3 and having ID3 polypeptide biological activity. Exemplary ID3 biological activities include forming heterodimer with helix-loop-helix (HLH) proteins and inhibition of DNA binding activity and transcriptional activity of basic helix-loop-helix transcription factors. An exemplary ID3 polypeptide sequence is provided below (NP_002158.3) (SEQ ID NO:3):

By "increasing cell survival" is meant positively altering cell viability. By "reducing cell survival" is meant negatively altering cell viability.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant

```
  1    mkalspvrgc yeavcclser slaiargrgk gpaaeeplsl lddmnhcysr lrelvpgvpr 61    gtqlsqveil grvidyildl qvvlaepapg ppdgphlpiq taeltpelvi sndkrsfch
```

By "ID3 polynucleotide" is meant a polynucleotide encoding a ID3 polypeptide. An exemplary ID3 polynucleotide sequence is provided at NCBI Accession No. NM_002167.4 (SEQ ID NO:4). SEQ ID NO:4 is provided below:

DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified"

```
   1    gatctggggt gctgccagga aaaagcaaat tctggaagtt aatggttttg agtgattttt 61    aaatccttgc tggcggagag gcccgcctct ccccggtatc agcgcttcct cattctttga 121    atccgcggct ccgcggtctt cggcgtcaga ccagccggag gaagcctgtt tgcaatttaa 181    gcgggctgtg aacgcccagg gccggcgggg gcagggccga ggcgggccat tttgaataaa 241    gaggcgtgcc ttccaggcag gctctataag tgaccgccgc ggcgagcgtg cgcgcgttgc 301    aggtcactgt agcgggactt cttttggttt tctttctctt tggggcacct ctggactcac 361    tccccagcat gaaggcgctg agcccggtgc gcggctgcta cgaggcggtg tgctgcctgt 421    cggaacgcag tctggccatc gcccggggcc gagggaaggg cccggcagct gaggagccgc 481    tgagcttgct ggacgacatg aaccactgct actcccgcct gcgggaactg gtacccggag 541    tcccgagagg cactcagctt agccaggtgg aaatcctaca gcgcgtcatc gactacattc 601    tcgacctgca ggtagtcctg gccgagccag cccctggacc cctgatggc ccccaccttc 661    ccatccagac agccgagctc actccggaac ttgtcatctc caacgacaaa aggagctttt 721    gccactgact cggccgtgtc ctgacacctc cagaacgcag gtgctggcgc ccgttctgcc 781    tgggaccccg ggaacctctc ctgccggaag ccggacggca gggatgggcc ccaacttcgc 841    cctgcccact tgacttcacc aaatcccttc ctggagacta aacctggtgc tcaggagcga 901    aggactgtga acttgtggcc tgaagagcca gagctagctc tggccaccag ctgggcgacg 961    tcaccctgct cccacccac ccccaagttc taaggtctct tcagagcgtg gaggtgtgga 1021    aggagtggct gctctccaaa ctatgccaag gcggcggcag agctggtctt ctggtctcct 1081    tggagaaagg ttctgttgcc ctgatttatg aactctataa tagagtatat aggttttgta 1141    ccttttttac aggaaggtga ctttctgtaa caatgcgatg tatattaaac ttttataaa 1201    agttaacatt ttgcataata aacgattttt aaacacttga aaaaaaaaa aa
``` can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder or that is associated with sensitivity or resistance to an agent. For example, a R183Q mutation in a GNAQ polynucleotide or polypeptide is a marker for Sturge-Weber syndrome, capillary malformation, and uveal melanoma. The R183Q mutation in a GNAQ polynucleotide or polypeptide is also a marker for puromycin sensitivity of a cell.

As used herein, "obtaining" as in "obtaining an agent" includes synthesizing, purchasing, or otherwise acquiring the agent.

As used herein, a "puromycin resistance polypeptide" is a polypeptide that confers resistance to puromycin in cells. Exemplary puromycin resistance polypeptides include, without limitation, a Pac (puromycin N-acetyltransferase) polypeptide. An exemplary sequence of a puromycin resistance polypeptide is provided at UniProtKB Accession No. P13249 (SEQ ID NO: 5). SEQ ID NO:5 is provided below.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM

```
         10         20         30         40         50
MTEYKPTVRL ATRDDVPRAV RTLAAAFADY aATRHTVDPD RHIERVTELQ 60         70         80         90        100
ELFLTRVGLD IGKVWVADDG AAVAVWTTPE SVEAGAVFAE IGPRMAELSG 110        120        130        140        150
SRLAAQQQME GLLAPHRPKE PAWFLATVGV SPDHQGKGLG SAVVLPGVEA 160        170        180        190
AERAGVPAFL ETSAPRNLPF YERLGFTVTA DVEVPEGPRT WCMTRKPGA
``` trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a murine, bovine, equine, canine, ovine, or feline.

By "TEAD3 polypeptide" is meant a polypeptide or fragment thereof having at least about 85% or greater amino acid identity to the amino acid sequence provided at NCBI Accession No. NP_003205.2, and having TEAD3 polypeptide biological activity. Exemplary TSC22D3 biological activities include transcription factor and DNA-binding activity. An exemplary TEAD3 polypeptide sequence is provided below (NP_003205.2) (SEQ ID NO:6):

```
  1    masnswnass spgearedgp egldkgldnd aegvwspdie qsfqealaiy ppcgrrkiil 61    sdegkmygrn eliaryiklr tgktrtrkqv sshiqvlark kvreyqvgik amnldqvskd 121    kalqsmasms saqivsasvl qnkfsppspl pqavfstssr fwssppllgq qpgpsqdikp 181    faqpaypiqp plpptlssye plaplpsaaa svpvwqdrti assrlrlley safmevqrdp 241    dtyskhlfvh igqtnpafsd ppleavdvrq iydkfpekkg glkelyekgp pnafflvkfw 301    adlnstiqeg pgafygvssq yssadsmtis vstkvcsfgk qvvekvetey arlengrfvy 361    rihrspmcey minfihklkh lpekymmnsv lenftilqvv tsrdsqetll viafvfevst 421    sehgaqhhvy klvkd
```

By "TEAD3 polynucleotide" is meant a polynucleotide encoding a TEAD3 polypeptide. An exemplary ID3 polynucleotide sequence is provided at NCBI Accession No. NM_003214.3 (SEQ ID NO:7). SEQ ID NO:7 is provided below:

```
   1   tcctcaacac aaactttccg tcccgctcgc tccctcctcc gcgctcggcg cctcccgctc
  61   cagcccggct cattccgcac attccggcca gcccctccc cacgaccccc cttccccggc
 121   cccccttgcg gctccctcgg gcccggcgga gcggcccggc cggagcgccc cgcgagctc
 181   ggaccaggct cagccgccca gtgggctcag gcccagagcc cagagcaacc agcacaatag
 241   cgtccaacag ctggaacgcc agcagcagcc ccggggaggc ccgggaggat gggcccgagg
 301   gcctggacaa ggggctggac aacgatgcgg agggcgtgtg gagcccggac atcgagcaga
 361   gcttccagga ggccctggcc atctacccgc cctgcggccg gcggaagatc atcctgtcag
 421   acgagggcaa gatgtacggc cgaaatgagt tgattgcacg ctatattaaa ctgaggacgg
 481   ggaagactcg gacgagaaaa caggtgtcca gccacataca ggttctagct cggaagaagg
 541   tgcgggagta ccaggttggc atcaaggcca tgaacctgga ccaggtctcc aaggacaaag
 601   cccttcagag catggcgtcc atgtcctctg cccagatcgt ctctgccagt gtcctgcaga
 661   acaagttcag cccaccttcc cctctgcccc aggccgtctt ctccacttcc tcgcggttct
 721   ggagcagccc ccctctcctg ggacagcagc tggaccctc tcaggacatc aagccctttg
 781   cacagccagc ctaccccatc cagccgcccc tgccgccgac gctcagcagt tatgagcccc
 841   tggcccccgct cccctcagct gctgcctctg tgcctgtgtg gcaggaccgt accattgcct
 901   cctcccggct gcggctcctg gagtattcag ccttcatgga ggtgcagcga gaccctgaca
 961   cgtacagcaa acacctgttt gtgcacatcg ccagacgaa ccccgccttc tcagacccac
1021   ccctggaggc agtagatgtg cgccagatct atgacaaatt ccccgagaaa aagggaggat
1081   tgaaggagct ctatgagaag gggcccccta atgccttctt ccttgtcaag ttctgggccg
1141   acctcaacag caccatccag gagggcccgg gagccttcta tggggtcagc tctcagtaca
1201   gctctgctga tagcatgacc atcagcgtct ccaccaaggt gtgctccttt ggcaaacagg
1261   tggtagagaa ggtggagact gagtatgcca ggctggagaa cgggcgcttt gtgtaccgta
1321   tccaccgctc gcccatgtgc gagtacatga tcaacttcat ccacaagctg aagcacctgc
1381   ccgagaagta catgatgaac agcgtgctgg agaacttcac catcctgcag gtggtcacga
1441   gccgggactc ccaggagacc ctgcttgtca ttgcttttgt cttcgaagtc tccaccagtg
1501   agcacgggc ccagcaccat gtctacaagc tcgtcaaaga ctagggtgcc ctctgcgcct
1561   ccttaaggat gcagggtgag catctcctct ccacacctgc ctggcacccc tgggggggtc
1621   caggattgag gattcatcta cctgccaggc ctcaggccca ggacccagga ggcctcccca
1681   cctaccccag cacacacact ccctgccact gttctgcgct ttaattgtgg gagaagagag
1741   gagaggaggg ctcagcggtg gggcagcctg tccggggcgc tgacccacca tcaccctgct
1801   ctgcccagcc tcgcgtgacc tcagagaggt ggggatagggg gacaccttca gcctccagca
1861   tgtgtggcca ctgtacccccc acccacccctt ggggagcat gatgggcagg tgagggcagg
1921   atggagacca agggagtcag tgagcagagg ccctgggagt gtccggttgg ggttggactg
1981   aggacagagg ggcccacact tccttgcccc tttgtgtccc aggcctggtg cccagactcc
2041   ttgcatggct tgtgtggtcc tcagactccg cacagcgagc gtaggtctct gggtttcaga
2101   tgaagtgccc aggctccagg aagttgaggg acccacagga gaggtgggca gagctggagt
2161   tctcatccag ggctgcttgt ccccagagcc caggtttata ctacctccct ggggcggggg
```

```
2221   ctggccgcag ggtaggggag aggctctgca gtgtggagtg gagcctcatc gaggggcgct
2281   gggttagggg agcacctgtt tcagactggg catgaagaag ggagcacagc agctactaga
2341   ccccattagc acctcattag cccacaagcc agccaggggc cccaggaaga tggggcaccc
2401   cccagcaccc tccagattga gagcaaggta gaggaaggag tcccagcctc tgggcagacc
2461   agaggcccag agggagagag tagcagaagg cttttgattt ttctcttgcc tgaggcttga
2521   atctgacaaa cccttggtgg gcactgctcc cttaggttct tccccacctc aatctacctg
2581   cctagagtag cagctcccag acccagttct gggactgaag gttaacccTT cacctgctgt
2641   cccttcttaa cacccaggcc cccagagcca gctgggcctg tccagcagcc acctgtgggt
2701   atttatgagt ttcatatgaa gtactgtgcc ccttcccttc ctcatcccga ccctgcccga
2761   gcttcctgaa ggtcctcact gtttgcatat cgctcaggcc acctccaaac cccacctagg
2821   ttttataatg tatattatat attttttgt gtattttaa aatccagctg tgatgggtta
2881   tatcataaat gcagcttggg gttggagcag gggccctcaa aggcccagct cctgctcaaa
2941   aaaaaaaaaa aaaaaaatt aaagttattt gtttgtgggt cagtcatgta aaaaaaaaa
3001   aaaaaaaaaa aaaaaaaaaa aaa
```

By "TSC22D3 polypeptide" is meant a polypeptide or fragment thereof having at least about 85% or greater amino acid identity to the amino acid sequence provided at NCBI Accession No. NP_001305399.1 (isoform 1), NP_004080.2 (isoform 2), or NP_004080.2 (isoform 3) and having TSC22D3 polypeptide biological activity. Exemplary TSC22D3 biological activities include inhibition of NFAT/AP-1 transcription and inhibition of the mTORC2 pathway. An exemplary ID3 polypeptide sequence is provided below (NP_001305399.1) (SEQ ID NO:8):

```
  1   maqskldcrs pvgldccncc ldlahrsglq rgssgennnp gsptvsnfrq lgeklvfenl
 61   ntdklnsimr qdslepvlrd pcylinegic nrnidqtmls illffhsasg asvvaidnki
121   eqamdlvknh lmyavreeve ilkeqirelv eknsqleren tllktlaspe qlekfqscls
181   peepapespq vpeapggsav
```

By "TSC22D3 polynucleotide" is meant a polynucleotide encoding a TSC22D3 polypeptide. An exemplary ID3 polynucleotide sequence is provided at NCBI Accession No. NM_001318470.1 (SEQ ID NO: 9). SEQ ID NO: 9 is provided below:

```
  1   gtcatatccc agtgctgact cccgggcgtg cagaccgcta actagctcac tcgctctcag
 61   ctcctgccac cgctcagccg tcacagccca ggggagcccg agagcctgag agcctgcaaa
121   ccggggaggg aggagcaaa ggagggaggg agcaagggcg cgccctggct ctccctctgc
181   cctgctgccc gccttcctg cctccacagg caccctggag tcccctcagg ccagctcggt
241   gggcgcgcac ctgccagccg cccctgacct cgcaggccag gcgacctccg agcctgagaa
301   gatgcccag tccaagctcg attgccgctc acctgtcggc ctcgactgct gcaactgctg
361   cctggacctg gccatcgga gtgggctcca gcgaggcagc agcggggaga caacaaccc
421   gggcagccct acagtgagca actttcggca gctgcaggaa aagctggtct ttgagaacct
481   caataccgac aagctcaaca gcataatgcg gcaggattcg ctagagccgg tgctgcggga
541   cccctgctac ctgatcaacg agggcatctg caaccgcaac atcgaccaga ccatgctctc
601   catcctgctc ttcttccaca gtgcctccgg agccagcgtg gtggccatag acaacaagat
661   cgaacaggcc atggatctgg tgaagaatca tctgatgtat gctgtgagag aggaggtgga
721   gatcctgaag gagcagatcc gagagctggt ggagaagaac tcccagctag agcgtgagaa
```

```
 781   caccctgttg aagaccctgg caagcccaga gcagctggag aagttccagt cctgtctgag 841   ccctgaagag ccagctcccg aatccccaca agtgcccgag gccctggtg gttctgcggt 901   gtaagtggct ctgtcctcag ggtgggcaga gccactaaac ttgttttacc tagttctttc 961   cagtttgttt ttggctcccc aagcatcatc tcacgaggag aactttacac ctagcacagc 1021   tggtgccaag agatgtccta aggacatggc caccctgggtc cactccagcg acagacccct 1081   gacaagagca ggtctctgga ggctgagttg catggggcct agtaacacca agccagtgag 1141   cctctaatgc tactgcgccc tgggggctcc cagggcctgg gcaacttagc tgcaactggc 1201   aaaggagaag ggtagtttga ggtgtgacac cagtttgctc cagaaagttt aagggggtctg 1261   tttctcatct ccatggacat cttcaacagc ttcacctgac aacgactgtt cctatgaaga 1321   agccacttgt gttttaagca gaggcaacct ctctcttctc ctctgtttcg tgaaggcagg 1381   ggacacagat gggagagatt gagccaagtc agccttctgt tggttaatat ggtataatgc 1441   atggctttgt gcacagccca gtgtgggatt acagctttgg gatgaccgct tacaaagttc 1501   tgtttggtta gtattggcat agttttctcta tatagccata aatgcgtata tatacccata 1561   gggctagatc tgtatcttag tgtagcgatg tatacatata cacatccacc tacatgttga 1621   agggcctaac cagccttggg agtattgact ggtcccttac ctcttatggc taagtctttg 1681   actgtgttca tttaccaagt tgacccagtt tgtcttttag gttaagtaag actcgagagt 1741   aaaggcaagg aggggggcca gcctctgaat gcggccacgg atgccttgct gctgcaaccc 1801   tttccccagc tgtccactga aacgtgaagt cctgttttga atgccaaacc caccattcac 1861   tggtgctgac tacatagaat ggggttgaga gaagatcagt ttgggcttca cagtgtcatt 1921   tgaaaacgtt ttttgttttg ttttgtaatt attgtggaaa actttcaagt gaacagaagg 1981   atggtgtcct actgtggatg agggatgaac aaggggatgg ctttgatcca atggagcctg 2041   ggaggtgtgc ccagaaagct tgtctgtagc gggttttgtg agagtgaaca ctttccactt 2101   tttgacacct tatcctgatg tatggttcca ggatttggat tttgattttc caaatgtagc 2161   ttgaaatttc aataaacttt gctctgtttt tctaaaaata aaaaaaaaa aaaaaaaaa 2221   aaa
```

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 2A-2D are plots and images showing results of lentiviral infection with Empty, WT, or mutant constructs in HEK 293T and in EA.296 cells. FIG. 2A and FIG. 2B each shows that a mutant HEK293T cell line and a mutant EA.296 cell line respectively showed less cell survival (approximate percent survival) compared to empty or wild-type. FIG. 2C shows that expression of Gαq was less in mutant compared to Empty and WT in both cell lines; insufficient growth of the EA.296 Q209L was obtained to gather protein for western. FIG. 2D shows that cells with mutant construct showed more rounded morphology than wildtype or empty (images shown are from transient transfection in HEK 293T cells that showed this same morphology).

FIG. 3A shows results of a Western blot showing levels of Gαq in cells transfected with the WT and mutant constructs. FIG. 3B shows a quantification of the Western blot results shown in FIG. 3A.

FIG. 4A shows results of a Western blot showing levels of p-ERK in cells transfected with the WT and mutant constructs. FIG. 4B shows a quantification of the Western blot results shown in FIG. 4A. P-ERK normalized to HSP90 (FIG. 4A) was significantly increased in mutant cells compared to WT (Panel B, *p<0.0).

FIG. 6A, FIG. 6B, FIG. 6C, FIG. 6D, FIG. 6E, and FIG. 6F each respectively show mRNA levels of TSC22D3, ID3, PIK3C2B, TEAD3, PRKCQ, and TRIO in cells transfected with WT and mutant constructs. Cells with mutant constructs were more sensitive to puromycin (0.4 μg/μl). TSC22D3 mRNA expression was decreased in cells with mutant constructs compared to WT and further decreased by puromycin exposure (FIG. 6A,*p<0.05). ID3 and TEAD3 expression were increased in mutants compared to WT and further increased by puromycin (FIG. 6B and FIG. 6D, *p<0.05).

FIG. 8A shows p-ERK immunohistochemistry and DAPI staining of blood vessel in the leptomeninges from subject with SWS. FIG. 8B shows p-ERK immunohistochemistry and DAPI staining of blood vessel in the leptomeninges from subject with Epilepsy (focal cortical dysplasia). FIG. 8C shows phosphorylated ERK expression was greater in endothelial cells from leptomeningeal vessels in subjects with SWS (*p<0.05).

DETAILED DESCRIPTION OF THE INVENTION

Figure 1:
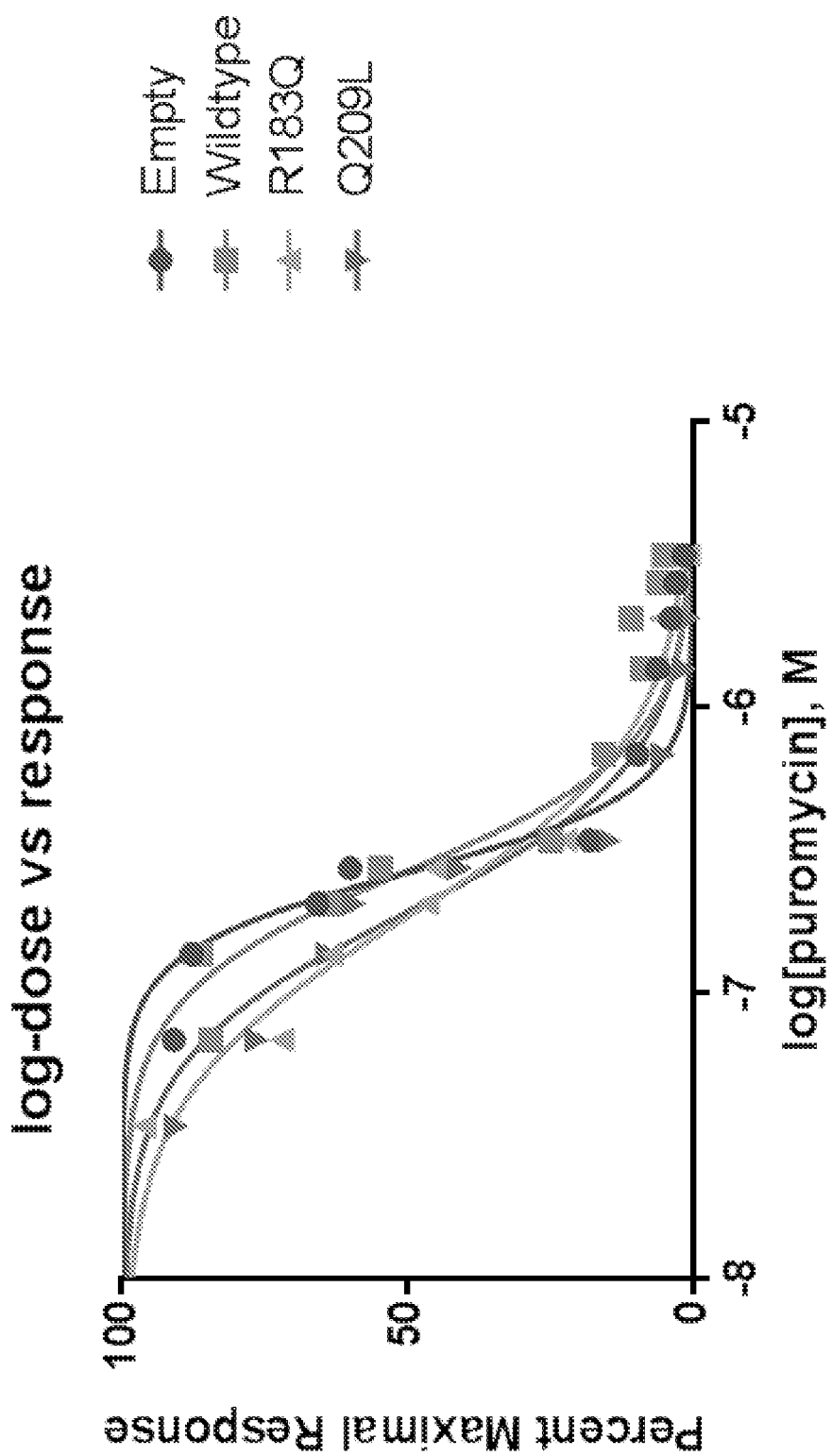
FIG. 1 is a plot showing response of cells as a function of puromycin concentration. HEK293T cells were transiently transfected with empty, wildtype, R183Q, or Q209L constructs and then exposed to puromycin for 3 days before cell number was assessed by MTT assay in 24 well plate. Half maximal inhibitory concentrations ($IC_{50}$) were 0.29 μM for empty and for wildtype, and 0.19 for R183Q and for Q209L. Two-way ANOVA demonstrated significant effects of both construct and dose (p<0.0001).

The invention features compositions and methods that are useful for treating vascular malformations or related conditions. The invention is based, at least in part, on the discovery of increased puromycin sensitivity in cells transfected with a GNAQ containing a R183Q or Q209L mutation. R183Q mutations in GNAQ cause Sturge-Weber syndrome (SWS), a rare congenital neurocutaneous disorder, and capillary malformations (port-wine birthmarks), as well as uveal melanoma. Q209L or R183Q mutations in GNAQ cause uveal melanoma. Puromycin exposure was noted to impair efforts to establish stable cell lines with either the GNAQ R183Q or Q209L mutation. When puromycin was removed from the media, the efforts to establish stable cell lines with the mutations were successful. Based on these observations, experiments were performed to better understand the effect of these mutations and puromycin upon gene expression in cells transiently transfected with these GNAQ mutations.

HEK293T cells were transiently transfected with R183Q or Q209L constructs and a puromycin dose response curve completed. A dose of puromycin which partially inhibited cell growth was identified. Gene expression changes resulting from the mutations and from the puromycin treatment were assessed by RT-PCR and western analyses. Puromycin inhibited cell growth in cells with the R183Q and Q209L mutations. mRNA expression of ID3 and TEAD3 were up-regulated and TSC22D3 mRNA down-regulated significantly in R183Q or Q209L mutants compared to GNAQ wildtype. In addition, TSC22D3 expression was further down-regulated and ID3 expression was further up-regulated by puromycin treatment.

Vascular Malformation/Sturge-Weber Syndrome

Capillary malformations/port-wine birthmarks occur in about 1 in 300 births and are very common. Sturge-Weber syndrome is a vascular malformation syndrome involving the brain, skin (capillary malformation/port-wine birthmark) and eye occurring in about 1 in 20,000 live births. Current treatments are primarily symptomatic and inadequate. The gene causing both Sturge-Weber syndrome and isolated port-wine birthmarks (capillary malformation of the skin not associated with brain or eye involvement) is the R183Q mutation in GNAQ. Recent evidence suggests that endothelial cells of the malformed blood vessels harbor the mutation (North et al., ISSVA 2014). Without being bound by theory, it is possible that other cell types also harbor the mutation.

Capillary Malformations

Capillary malformations (port-wine stains) occur in about 1 in 300 live births and most of these occur on the head and neck regions. Some fading of the birthmark may be noted during the first year of life; however, these malformations are not self-resolving and require multiple courses of laser treatment with varying degrees of success. Capillary malformations frequently change from pink to red in early adulthood to a deep purple color later in adulthood. The surface may thicken (cobblestoning) and soft and bony hypertrophy may occur; these changes occur in about 60% of patients to varying degrees (Geronemus et al. (1991) J. Dermatol. Surg. Oncol.; 17(1):76-9). Nodular vascular lesions or pyogenic granulomas with bleeding can develop in adulthood. Psychosocial disability secondary to facial disfigurement can be severe, can worsen with adulthood, and include greater self-concern, self-doubt in interpersonal interactions, social inhibition, isolation, stigmatization from society, and limited opportunities compared to those without facial disfigurement (Geronemus et al. (1991) J. Dermatol. Surg. Oncol. 17(1):76-9). Less commonly acquired port-wine stains can occur at any age and are identical to congenital capillary malformations both clinically and histologically. Trauma, chronic UV exposure, and infections, have all been implicated in triggering the formation of acquired capillary malformations and a latent lesion brought out by trauma has been considered as a possible mechanism and acquired capillary malformation has been reported after trauma in the context of a congenital lesion (Tallman et al. (1991) Pediatrics 87(3):323-7).

Overall about 10% of facial capillary malformations are associated with vascular malformations in brain and/or eye (Sturge-Weber syndrome) but the risk primarily involves those infants born with a birthmark on the forehead, temple region, and/or upper eyelid (20-50%) (Comi (2011) Neurologist 17(4):179-84). Risk of glaucoma in these patients ranges from 25-75% (Tallman et al. (1991) Pediatrics 87(3): 323-7) and the glaucoma can be refractory to available medical and surgical treatments resulting in vision loss. Brain involvement with the "leptomeningeal angioma" presents with seizures, strokes, migraines and focal neurologic impairments usually in the first two years of life (Shirley et al. (2013) N. Engl. J. Med. 368(21):1971-9), however about 10% of these individuals present later in childhood, adolescence or adulthood. Impaired venous drainage results in impaired brain perfusion which is exacerbated by seizures (Sujansky et al. (1995) J. Child Neurog. 10(1):49-58). The mainstay of current treatment for Sturge-weber syndrome is aggressive use of anticonvulsants. However medical management is effective in suppressing seizures in only about half of these patients, side effects are common, and neurologic impairments almost universal. Some patients have extensive, bilateral brain involvement and early onset of medically refractory seizures; for these patients especially the available treatments are very inadequate.

Pathophysiology

The cause of both Sturge-Weber syndrome and isolated port-wine birthmarks is a R183Q somatic mosaic mutation in GNAQ in endothelial cells (Shirley et al. (2013) N. Engl. J. Med. 368(21):1971-9). Without being bound by theory, the mutation is predicted to impair autohydrolysis of the GTP binding site of Gαq thus maintaining the protein in an abnormally activated state. Transient transfection studies in HEK293T cells suggested that this mutation constitutively activates downstream pathways, with westerns demonstrating increased phosphorylated ERK and JNK (Shirley et al. (2013) N. Engl. J. Med. 368(21):1971-9). Histology demonstrates an increased number of capillary-venous vessels which dilate over time; the ectatic vessels tend to progress from the superficial dermis to the deeper dermis and subcutaneous tissues. Immunohistological studies of capillary malformations and Sturge-Weber syndrome brain tissue have implicated increased endothelial cell VEGF signaling. Vascular endothelial growth factor (VEGF)-A and its most active receptor VEGF-R2 expression are significantly increased in capillary malformation skin tissue compared with control skin (Comati et al. (2007) J. Neuropathol. Exp. Neurol. 66(1):86-97); similarly VEGF-R expression is increased in the endothelial cells of the malformed Sturge-Weber leptomeningeal vessels while mRNA expression levels of VEGF is increased in the underlying cortex (Comati et al. (2007) J. Neuropathol. Exp. Neurol. 66(1):86-97). Studies therefore suggest that venous stasis promotes surrounding tissue hypoxia and increases VEGF expression which may contribute to progression of the vascular malformation.

GNAQ Mutations in Various Disorders

Hyperactivating mutations in GNAQ results in a growing number of disorders recently identified including uveal melanoma, blue nevi, Phakomatosis Pigmentovascularis and extensive dermal melanocytosis, melanocytic tumors originating in the central nervous system, low-grade glioma, port-wine birthmarks and Sturge-Weber syndrome (van de Nes et al. J. Neurooncol. 2016, doi:10.1007/s11060-015-2052-2; Shirley et al., N. Engl. J. Med. 2013; 368:1971-1979; Van Raamsdonk et al., Nature 2009; 457:599-602; Thomas et al., J. Invest Dermatol. 2016, doi: 10.1016/j.jid.2015.11.027; Chan et al., Mod. Pathol. 2016, doi: 10.1038/modpathol.2015.153; Laviv et al., FEBS Open. Bio 2012; 2:129-134). GNAQ codes for Gαq, part of the trimeric G protein complex associated with a large subgroup of G protein coupled receptors (O'Hayre et al., Nat. Rev. Cancer 2013; 13:412-424). The R183Q and Q209L mutations are predicted to result in impaired auto-hydrolysis and therefore impaired deactivation of Gαq and constitutive hyperactivation of downstream pathways (Shirley et al., N. Engl. J. Med. 2013; 368:1971-1979; Van Raamsdonk et al., Nature 2009; 457:599-602). The involved hyperactivated pathways are beginning to be elucidated and include the Ras-Raf-MEK-ERK (Shirley et al., N. Engl. J. Med. 2013; 368:1971-1979), mTOR (Amirouchene-Angelozzi et al., Mol. Oncol. 2014; 8:1508-1520), and YAP-HIPPO pathways (Yu et al., Cancer Cell 2014; 25:822-830), however current understanding of the impact of these pathways upon gene expression is far from complete. Furthermore, efforts to identify novel targets or treatment approaches for capillary malformations, Sturge-Weber syndrome, uveal melanoma and other impacted tumors continue.

Sturge-Weber Syndrome (SWS), a sporadic neurocutaneous syndrome is classically associated with facial port-wine birthmark (PWB), with an ipsilateral vascular malformation in the eye causing glaucoma, and a leptomeningeal angioma involving the brain (Bachur et al., Curr. Treat. Options. Neurol. 2013; 15:607-617). The patients with Sturge-Weber Syndrome (SWS) present with clinical features including seizures, stroke-like episodes, and glaucoma because of vascular malformations involving the skin, brain, and eyes. Some patients display cognitive issues with attention issues/attention deficit hyperactivity disorder (Lance et al., Pediatr. Neurol. 2014; 51:675-680; Kavanaugh et al., Child Neuropsychol. 2015; 1-14. Isolated port-wine birthmarks occur in approximately 1:300 live births and consist of abnormal capillary-venous vessels in the dermis of the skin (Tallman et al., Pediatrics 1991; 87:323-327). The leptomeningeal vascular malformation consists of an increased number of tortuous vessels in the leptomeninges many of which are thin-wall and some of which are narrowed by sub-endothelial proliferation and hyalinization (Comati et al., J. Neuropathol. Exp. Neurol. 2007; 66:86-97; Di Trapani et al., Childs Brain 1982; 9:23-36). Recently both SWS and isolated port-wine birthmarks (capillary malformations) were shown to be associated with R183Q mutations in GNAQ (Shirley et al., N. Engl. J. Med. 2013; 368:1971-1979; Couto et al., Plast. Reconstr. Surg. 2016 January; 137(1):77e-82e. doi: 10.1097/PRS.0000000000001868; Nakashima et al., J. Hum. Genet. 2014; 59:691-693).

Both R183Q and Q209L GNAQ mutations have been demonstrated in uveal melanoma, with the Q209L mutation being the more common mutation (Van Raamsdonk et al., Nature 2009; 457:599-602). Prior studies have shown that the Q209L mutation is more activating than the R183 mutation (Shirley et al., N. Engl. J. Med. 2013; 368:1971-1979); the mutation is predicted to interfere more with the auto-hydrolysis site of the protein.

While pursuing efforts to establish stable endothelial cells (EA.hy926) lines with lentivirus plasmids and puromycin selection, it was noted that both R183Q and Q209L infectedcells barely survived puromycin selection, whereas most of those cells infected by empty and wildtype GNAQ plasmids survived under the same conditions. Work with human microvascular endothelial cells (HMEC) to produce stable cell lines with puromycin selection also resulted in fewer clones, with less robust protein expression and impaired growth when the cells were maintained with puromycin. These observations suggested that the R183Q and Q209L mutations may induce enhanced cell vulnerability to puromycin. Therefore transient transfection of pcDNA3.1-E, -GNAQ, -R183Q and -Q209L into HEK293T cells was performed, and then a puromycin dose response curve was performed, followed by RT-PCR and western analyses for gene expression changes resulting from the mutant transfections combined with puromycin exposure. Results of these experiments are described elsewhere herein.

GNAQ and Cellular Signaling

An interaction, between the effects of hyperactivating GNAQ mutations and cellular insults from exposure to puromycin, has been previously described; however this interaction has been previously studied from a very different perspective and in a very different context. Wang et. al. studied the puromycin aminonucleoside nephrosis (PAN model) of focal segmental glomerulosclerosis both in vitro and in vivo, and combined this with expression of the constitutively hyperactive Q209L GNAQ mutation. They found that the Q209L mutation alone was insufficient to produce injury, however adding exposure to puromycin resulted in cellular injury, albuminurea, and focal segmental glomerulosclerosis which was more severe than in the Q209L animals treated with vehicle. Using a calcineurin/NFAT and Q209L reporter mouse they showed that GNAQ hyperactivation signaled through NFAT. An important gene target of NFAT signaling is Transient Receptor Potential Channel 6 (TRPC6) activity, an ion channel with activity that was increased by Gαq induction and inhibited by the calcineurin inhibitor FK506. TRPC6 knockout Q209L mice treated with puromycin did not demonstrate the increased susceptibility to puromycin suggesting that the enhance puromycin sensitivity was at least partially reliant on TRPC6 activity (Wang, J Clinical Invest 2015 May; 125(5): 1913-26).

TRP channels are cation-permeable channels broadly expressed in organisms and tissue types, including the brain and the vasculature. TRP channels mediate a wide range of physiological functions including cell cycle regulation, cell apoptosis and survival. Endothelial cells express several transient receptor potential isoforms; their activity modulates cytosolic calcium levels and membrane potential (Kwan et al. Biochemica et Biophysica Acta 2007 August; 1772(8):907-14). Gαq activation of TRPC6 signals the activation of PKCα which then induces RhoA activity, endothelial cell contraction (Singh et al 2007, J Biol Chem March 16; 282(11):7833-43), and resulting in endothelial barrier dysfunction. Interestingly, a rounded shape with inter-endothelial gaps is described in the abnormal endothelial cells of both port-wine blood vessels and of the leptomeningeal vessels in Sturge-Weber syndrome and noted in this study as well. Contrast enhancement on Mill imaging is used to diagnose the leptomeningeal angioma in SWS; this clinical finding also suggests endothelial barrier dysfunction. Inhibiting excessive TRPC6 signaling may result in improved endothelial barrier and vascular function. Furthermore, TRPC6 is associated with pressure related diseases in many conditions and its expression can be induced by mechanical stimulation. The intravascular pressure-induced depolarization and constriction of small arteries and arterioles are regulated by TRPC6 and its expression is increased in pulmonary hypertension (Lin et al., Circ Res. 2004; 95(5):496-505). TRPC6 complexes with other proteins and appears to form an environmental pressure sensor. This has generated interest regarding the role of TRPC6 in glaucoma (Fan et al., Int J Ophthalmol. 2012; 5(4): 523-526) and suggests a role for this protein in the response to capillary-venous engorgement and impaired function in capillary malformations and Sturge-Weber syndrome. Endothelial TRPC6 contributes to VEGF-induced calcium influx in microvessel endothelial cells (Hamdollah Zadeh et al., Microcirculation. 2008 October; 15(7): 605-614). Therefore, excessive activation could result in impaired cellular function, and inhibiting this pathway theoretically could be protective.

Ca++ influx via TRPC6 also activates calcineurin, increases ERK phosphorylation and increases NFAT expression. NFAT is known to induce the activity of inhibitor of DNA binding (ID3), at least in some contexts. Koltsova et al. reported Egr1 and NFAT act together to promote the development of T-cells and cooperatively induce the expression of ID3 (Koltsova et al., Biochemistry (Mosc). 2007 September; 72(9):954-61). The ERK and Ca++ signaling pathways act in concert by converging on the NFAT pathway. Ids are a small family of helix-loop-helix proteins that lack the ability to interact with DNA but act as dominant-negative transcription factors, and regulate a variety of cellular functions including cell cycle progression, proliferation, migration, angiogenesis, and invasion. Upregulation has been found in a variety of cancers, including melanoma (DiVito et al 2014, Carcinogenesis, April; 35(4):951-8).

ID3 is pro-angiogenic and it has been suggested as a therapeutic target for the treatment of melanoma and several other cancers where ID3 expression is increased (DiVito et al 2014, Carcinogenesis, April; 35(4):951-8). ID1 and ID3 expression regulated by Akl1 are both necessary for full induction of EphrinB2, itself critical to driving blood vessels to either venular phenotype (EphrinB2−) or to arteriolar phenotype (EphrinB2+) (Kim et al. 2012 Angiogenesis. 2012 September; 15(3):497-509). In T-helper cells, ID3 modulates the activities of the PI3K-AKT-mTORC1-HIF1α pathway to modulate cellular proliferation. In endothelial cells, Id1 and Id3 are induced by VEGF and TGFbeta and overexpression of these Id proteins enhance MMP2 and MMp9 expression and tube formation (Sakurai et al 2004, J Immunol. 2004 Nov. 1; 173(9):5801-9.). ID protein inhibition has been suggested as a target for treatment in vascular malformations. The results in this study suggest that over-expression of mutant Gαq results in increased ID3 expression and we hypothesize that this may have a role in the abnormal vascular structure and function of the leptomeningeal blood vessels. Constitutively increased ID3 expression furthermore may contribute to increased sensitivity to puromycin toxicity. Further studies are needed to address this hypothesis.

TSC22D3 (also known as GILZ) is a glucocorticoid induced leucine zipper gene. TSC22D3 inhibits NFAT/AP-1 transcription (de Bosscher et al. 2003, Endocr Rev. 2003 August; 24(4):488-522), interacts directly with c-Fos and c-Jun, and inhibits Raf-1 phosphorylation (and thereby suppress MEK and ERK phosphorylation) in normal T-cells (Ayroldi et al 2002 Mol Cell Biol. November; 22(22):7929-41). TSC22D3 expression is induced by glucocorticoid (corticosteroid) treatment in airway epithelial cells (Eddleston et al. 2007, J Allergy Clin Immunol. January; 119(1):115-22) and smooth muscle cells (Kelly et al. 2012 Br J Pharmacol. March; 165(6):1737-47). GILZ is a key inhibitor of the mTORC2 pathway and reduces AKT (Joha 2012 Oncogene. March 15; 31(11):1419-30). GILZ overexpression in microvascular endothelial cells inhibited TNF-α induced activation of p38, ERk, and JNK MAPKs (Cheng et al. 2013 J Immunol. July 1; 191(1):424-33). Here TSC22D3 expression was decreased in the GNAQ mutants and further decreased by puromycin in all the cells. Without being bound by theory, decreased TSC22D3 expression is believed to contribute to hyperactivation of the MEK-ERK pathway and therefore enhance susceptibility to puromycin toxicity.

Corticosteroids are used intermittently in patients with Sturge-Weber syndrome when anticonvulsants and other acute management fail to bring prolonged episodes of seizures, migraines and stroke-like episodes under control. One function of corticosteroids in the treatment of Sturge-Weber syndrome may be to increase the inhibition of these pathways through increased expression of GILZ. Chronic steroid use has significant medical complications and therefore identification of drugs lacking off target effects is currently underway for a number of conditions impacted by these pathways that should include uveal melanoma, Sturge-Weber syndrome and port-wine birthmarks.

Transcriptional enhancer factor (TEF-5) is the protein that in humans is encoded by the TEAD3 gene. It is a member of the transcriptional enhancer factor (TEF) family of transcription factors which contain the TEA/ATTS DNA-binding domain. It plays a key role in the Hippo signaling pathway, a pathway involved in organ size control and tumor suppression by restricting proliferation and promoting apoptosis. The pathway is essentially composed of a kinase cascade where MST1/MST2, in complex with its regulatory protein SAV1, phosphorylates and activates LATS1/2 complexed with its regulatory protein MOB1, which in turn phosphorylates and inactivates the YAP1 oncoprotein and WWTR1/TAZ. TEF-5 acts by mediating gene expression of YAP1 and WWTR1/TAZ to regulate cell proliferation and migration. It binds to multiple functional elements of the human chorionic somatomammotropin-B gene enhancer and normally it is predominately expressed in the placenta, but is also expressed in the nervous system and muscles of embryonic fish, and in the early developing mouse heart. TEF-5 is important in the transactivation of the chorionic somatomammotropin-B gene enhancer (also called human placental lactogen; hPL) which has weak actions similar to growth hormone although 100 times greater amounts are required to produce the same effect. $\alpha^1$-adrenergic receptor activity in neonatal mouse cardiac myocytes increases TEF-5 activity, suggesting a role in the signaling downstream of Gαq.

GNAQ and Clinical Relevance

Previous studies of molecular neuropathology in Sturge-Weber syndrome provide an important context for the interpretation of these results. Comati et al. reported in 2007 that the majority of the vessels were thin walled vessels of variable caliber, ectatic, CD34+, and covered by a layer of smooth muscle/pericytes (Comati et al., J Neuropathol Exp Neurol. 2007 January; 66(1):86-97). Most SWS vessels did not have an internal elastic lamina, as indicated by Elastica van Gieson stain indicating that the leptomeningeal angioma primarily consists of vessels with venous characteristics. Arterial vessels with an internal elastic lamina were scattered within the leptoangiomatous lesion. Compared to control leptomeningeal vessels, and cortical vessels from the same SWS samples, these SWS leptomeningeal vessels expressed greater amounts of VEGFR-1 and VEGFR-1 and HIF1α and HIF2α. They suggested a model whereby increased VEGF released by the hypoxic cortex stimulated the increased release HIF1α and further increases in VEGF. A greater mitotic index for the endothelial cells of these vessels was also noted suggesting ongoing vascular remodeling. Decreased protein levels of fibronectin expression in SWS leptomeningeal vessels have also been reported. VEGF and VEGFR signal through Gαq, and therefore the hyperactivating R183Q mutation in GNAQ may increase the expression of HIF1α and this data suggests that increased ID3 expression may be involved.

In port-wine birthmarks, increased endothelial cell p-ERK expression has also been reported and suggested to contribute to early morphological vascular structural and functional abnormalities (Tan et al 2014 J Am Acad Dermatol. November; 71(5):964-8). Adult and hypertrophied port-wine birthmarks are reported to also demonstrate increase expression of other downstream kinases suggesting that progressive hyperactivation of these pathways may contribute to the vascular ectasia and birthmark hypertrophy that can occur over time. It has also been suggested that increased expression of VEGF and VEGF expression contributes to vascular hypertrophy in port-wine birthmarks (Vural et al Otolaryngol Head Neck Surg. 2008 October; 139(4):560-4). Puromycin is an aminoglycocide antibiotic that is utilized frequently in the lab for selection of transfected cells with a gene conveying antibiotic resistance. Its toxicity in non-resistant cells is generally understood to result from its inhibition of protein transcription. However it also inhibits Puromycin-sensitive aminopeptidase (PSA; also called NPEPPS) which contains the zinc-binding domain characteristic of the gluzincin group of zinc metalloproteases. NPEPPS is an aminopeptidase with broad substrate specificity for several peptides. It is involved in proteolytic events essential for cell growth and viability. It may act as regulator of neuropeptide activity, have a role in the antigen-processing pathway for MHC class I molecules and be involved in the N-terminal trimming of cytotoxic T-cell epitope precursors. It digests the poly-Q peptides found in many cellular proteins.

Constitutively increased ID3 expression in the GNAQ mutants in the studies herein was associated with increased sensitivity to puromycin toxicity; without being bound by theory, constitutively increased ID3 may increase HIF1α expression and drive further VEGF release. Similarly, in the studies herein, decreased TSC22D3 expression was associated with increased puromycin susceptibility.

Puromycin's toxicity limits its clinical usefulness, although it has, in the past, been studied in a few clinical cancer trials. Here the value of puromycin is primarily as a metabolic stressor highlighting that the GNAQ mutations increase cell vulnerability. Considering treatment strategies, without being bound by theory, puromycin (or a safer analogue) administered topically after laser treatment of a capillary malformation (port-wine birthmark) would preferentially reduce regrowth of abnormal blood vessels. It is also a possible treatment strategy for uveal melanoma.

Bestatin (ubenimex, Eiger BioPharmaceuticals, Inc.), is an oral, competitive, reversible protease inhibitor of the leukotriene $A_4$ hydrolase ($LTA_4H$), an enzyme that converts $LTA_4$ to $LTB_4$, and an inflammatory mediator that occurs naturally. It has also been shown to inhibit PSA and to inhibit cell proliferation. Bestatin has been marketed in Japan for more than 25 years for the treatment of Pulmonary Arterial Hypertension (PAH) and other inflammatory diseases. It is currently in clinical trials for the treatment of AML. If PSA inhibition is important to the increase puromycin sensitivity of the GNAQ mutants observed here, the bestatin, a drug current in clinical trials may mimic these effects.

Ultimately the goal of translational research is to identify novel molecular targets and treatment strategies for clinical conditions. Without being bound by theory, data herein indicate that puromycin analogues, or other drugs targeting ID3, TSC22D3 or PSA (such as Bestatin) could provide novel targets for further study. These studies have been crucial to the success of efforts to establish stable endothelial cell lines with these GNAQ mutations. With these stable cell lines, efforts have now begun to further study these targets and carry out dose response curves to test the ability of drugs to induce cell death or normalize cellular function.

Puromycin and Cellular Signaling

Puromycin is an aminonucleoside known to have toxic effects upon cells. It is an antibiotic commonly used in stable cell line selection. Recently reported work in mice with GqQ>L (Q209L) induction in podocytes exposed to puromycin (model for a kidney disease called focal glomerular sclerosis) developed more glomerular injury compared to control animals and linked this finding to TRPC6 signaling (Wang et al. (2015) J. Clin. Invest 125(5):1913-26). TRPC6 channels are Ca2+ permeable non-selective cation channels that can be activated by both G-protein coupled receptors (GPCR) and by receptor tyrosine kinases via phospholipase C (PLC) and diacylglycerol (DAG) mediated signaling. In podocytes with the induced Q209L mutation TRPC6 activation did not cause glomerular damage in the absence of an additional cell stressor.

Increased Sensitivity to Puromycin in GNAQ R183Q Cells

The present invention features a method of inhibiting proliferation and/or reducing survival of a cell comprising a GNAQ polynucleotide or polypeptide having a R183Q or Q209L mutation, comprising contacting the cell with puromycin or a puromycin analog. In the process of establishing HEK293 and endothelial cell lines with the R183Q and Q209L GNAQ mutations, an unexpected finding which has several important translational implications was stumbled upon. Wildtype, R183Q, and Q209L GNAQ constructs were inserted into a lentivirus-plasmid, the sequences were confirmed and after transfection, and puromycin selection was done to generate stable HEK293 and EA.hy 296 (endothelial) cell lines. In the HEK293 cells, 90-100% of the cells with empty or wildtype GNAQ construct survived the selection whereas only 75% of the cells with the R183Q and 40% of the Q209L mutations survived the selection. In the EA.hy 926 endothelial cells 100% of the cells with the empty or wildtype constructs, but only 30% of those with the R183Q and less than <5% of those with the Q209L mutation survived the puromycin selection. This amount of cell death after puromycin selection was unexpected. Without wishing to be bound by theory, it was possible that the cells did not tolerate the transfection with multiple copies of the QNAQ mutations. However, this much cell death after transient transfection into these cells with the GNAQ mutant constructs was not previously observed. Without being bound by theory, an alternative explanation was that puromycin was more toxic to cells with the mutations.

The studies described herein are the first to link puromycin sensitivity to the R183Q and Q209L GNAQ mutation in endothelial cells and vascular malformations and related syndromes, and to suggest use of this antibiotic, its analogs, or its inhibitors for the treatment of capillary malformations and related syndromes. Furthermore, the finding indicates that human endothelial cells with the R183Q GNAQ mutation are puromycin sensitive, implying that capillary malformations may be treated with puromycin (or puromycin analog) applied topically, either following laser treatment or as the sole treatment to cause fading of the birthmark or to prevent the progression (blebbing, soft tissue hypertrophy). Accordingly, the present invention provides methods of reducing a vascular malformation in a subject, inhibiting progression of a vascular malformation in a subject, reducing appearance of a birthmark in a subject, and treating a vascular malformation or related condition in a subject. The methods comprise administering to the subject an effective amount of puromycin or a puromycin analog.

This finding also has immediate implications for efforts to generate cell culture models of capillary malformations/Sturge-Weber syndrome since it is common to maintain stable cell lines in media with puromycin after selection. Thus, the present invention features cell lines comprising an isolated polynucleotide encoding a GNAQ polypeptide comprising a R183Q or Q209L mutation. In some embodiments, the cell lines further comprise an isolated polynucleotide encoding a puromycin resistance polypeptide.

Finally, puromycin sensitivity may also serve as a suitable and titratable in vitro assay for identification of drugs which block this effect. Candidate drugs blocking or enhancing puromycin sensitivity could prove useful for treatment of vascular malformations. Accordingly, the present invention features methods of identifying candidate agents that modulate a vascular malformation. The screening methods comprise contacting a cell comprising a GNAQ polynucleotide or polypeptide having a R183Q or Q209L mutation with puromycin and a candidate agent; and comparing viability of the contacted cell with a reference level of viability. The screening methods may also comprise comparing levels of GNAQ polypeptide or polynucleotide and levels of polypeptides or polynucleotides of genes downstream of GNAQ polypeptide (or Gαq) dependent signaling pathways.

Treatment of Vascular Malformation and Related Conditions with Puromycin

Puromycin was identified as an agent useful for preventing or ameliorating a disease associated with a GNAQ R183Q mutation. Diseases associated with a GNAQ R183Q mutation include, without limitation, vascular malformation, vascular malformation in the eye, vascular malformation in the brain, capillary malformation, Sturge-Weber syndrome, and uveal melanoma. For example, the cause of both Sturge-Weber syndrome and isolated port-wine birthmarks is a R183Q somatic mosaic mutation in GNAQ in endothelial cells. The same mutation in melanoma cells causes uveal melanoma.

Accordingly, the present invention provides methods of treating disease associated with a GNAQ Q209L or R183Q mutation and/or disorders or symptoms thereof which comprise administering a therapeutically effective amount of a pharmaceutical composition comprising a puromycin or puromycin analog to a subject (e.g., a mammal such as a human). One embodiment is a method of treating a subject suffering from or susceptible to a disease associated with GNAQ R183Q mutation (e.g., vascular malformation, vascular malformation in the eye, vascular malformation in the brain, capillary malformation, Sturge-Weber syndrome, and uveal melanoma) or disorder or symptom thereof. The method includes the step of administering to the mammal a therapeutic amount of puromycin or a puromycin analog sufficient to treat the disease or disorder or symptom thereof, under conditions such that the disease or disorder is treated.

The methods herein include administering to the subject (including a subject identified as in need of such treatment) an effective amount of a puromycin or puromycin analog, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of puromycin or puromycin analog to a subject (e.g., animal, human) in need thereof, including a mammal, particularly a human. Such treatment will be suitably administered to subjects, particularly humans, suffering from, having, susceptible to, or at risk for vascular malformation, vascular malformation in the eye, vascular malformation in the brain, capillary malformation, Sturge-Weber syndrome, and uveal melanoma. In particular embodiments, the puromycin or puromycin analog is administered to a subject having a capillary malformation ("port wine stain" or "port wine birthmark") to cause fading of the birthmark. In particular embodiments, the puromycin or puromycin analog is administered to a subject having a vascular malformation to prevent the progression of the disease (e.g., blebbing, soft tissue hypertrophy).

Determination of those subjects "at risk" can be made by any objective or subjective determination by a diagnostic test or opinion of a subject or health care provider (e.g., genetic test (particularly, genetic test for GNAQ R183Q mutation), enzyme or protein marker, family history, and the like). The puromycin compositions herein may be also used in the treatment of any other disorders in which the GNAQ R183Q mutation may be implicated.

In some embodiments, a subject is selected for treatment with puromycin or a puromycin analog by detection of a GNAQ R183Q mutation in a sample obtained from the subject. The sample obtained from the subject may be a sample of endothelial cells from a capillary malformation in the subject. Methods for detecting a GNAQ R183Q mutation in the sample include immunoassay, direct sequencing, and probe hybridization to a polynucleotide encoding the mutant polypeptide.

The administration of a therapeutic composition comprising puromycin or puromycin analog may be by any suitable means that results in a concentration of the therapeutic that, combined with other components, is effective in ameliorating, reducing, or stabilizing a GNAQ R183Q mutation-associated disease (e.g., vascular malformation, vascular malformation in the eye, vascular malformation in the brain, capillary malformation, Sturge-Weber syndrome, and uveal melanoma). The therapeutic composition comprising puromycin or a puromycin analog may be administered systemically, for example, formulated in a pharmaceutically-acceptable buffer such as physiological saline. The therapeutic composition comprising puromycin or a puromycin analog may also be administered topically. Routes of administration include, for example, subcutaneous, intravenous, interperitoneally, intramuscular, or intradermal injections that provide continuous, sustained levels of the drug in the patient.

Treatment of human patients or other animals is carried out using a therapeutically effective amount of puromycin or a puromycin analog in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the GNAQ R183Q mutation-associated disease. Generally, amounts will be in the range of those used for other agents used in the treatment of the GNAQ R183Q mutation-associated disease, although in certain instances lower amounts will be needed because of the increased specificity of the compound. The therapeutic composition is administered at a dosage that ameliorates the GNAQ R183Q mutation-associated disease and/or symptoms thereof (e.g., reduces the vascular malformation or reduces appearance of a birthmark) as determined by a method known to one skilled in the art.

The therapeutic agent may be contained in any appropriate amount in any suitable carrier substance, and is generally present in an amount of 1-95% by weight of the total weight of the composition. The composition may be provided in a dosage form that is suitable for parenteral (e.g., parenterally by injection) administration route. The composition may be provided in a dosage form that is suitable for topical administration or ocular administration. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Compositions may be provided in unit dosage forms (e.g., in single-dose ampoules), or in vials containing several doses and in which a suitable preservative may be added. The composition may be in the form of a solution (e.g., eye drops, spray, oil), a suspension (e.g., gel, hydrogel, ointment, paste), an emulsion, a dermal application (e.g., topical cream, liniments, film, patch, lotion, balm), or any appropriate method known in the art. It may be presented as a dry powder (e.g., effervescent powder) to be reconstituted with water or another suitable vehicle before use. Apart from the active agent(s) that reduces or ameliorates a GNAQ R183Q mutation-associated disease (e.g., a vascular malformation or related condition), the composition may include suitable parenterally acceptable carriers and/or excipients. Furthermore, the composition may include suspending, solubilizing, stabilizing, pH-adjusting agents, tonicity adjusting agents, and/or dispersing, agents.

In particular embodiments, the composition is formulated for ocular or ophthalmic administration. In particular embodiments, the composition is in the form of a solution, particularly a solution suitable for ophthalmic application (e.g., eye drops). In particular embodiments, the composition is formulated for topical administration. In particular embodiments, the composition is in the form for dermal application (e.g., a topical cream). In compositions suitable for dermal application, the puromycin or puromycin analog may be incorporated with petroleum jelly, beeswax, paraffin, polyethylene glycol, gelatin, or the like.

In particular embodiments, the composition is formulated for administration by injection. Pharmaceutical compositions according to the invention may be prepared in the form suitable for sterile injection. To prepare such a composition, the puromycin or puromycin analog is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

In particular embodiments, the composition is formulated for oral administration. Formulations for oral administration include tablets containing puromycin or a puromycin analog in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed. The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra.

Combination Therapies

In some embodiments, the therapeutic composition comprising puromycin or a puromycin analog may be administered to a subject having vascular malformation or related condition, in combination with any other standard therapy for the disease. Standard therapy for vascular malformation includes, for example, laser treatment.

Kits

The invention provides kits for the treatment or prevention of a GNAQ R183Q mutation-associated disease (e.g., vascular malformation, vascular malformation in the eye, vascular malformation in the brain, capillary malformation, Sturge-Weber syndrome, and uveal melanoma). In one embodiment, the kit includes a therapeutic or prophylactic composition containing an effective amount of puromycin or puromycin analog. In some embodiments, the kit comprises a sterile container which contains the therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the therapeutic or prophylactic composition is provided together with instructions for administering the puromycin or puromycin analog to a subject having or at risk of developing a GNAQ R183Q mutation-associated disease (e.g., vascular malformation, vascular malformation in the eye, vascular malformation in the brain, capillary malformation, Sturge-Weber syndrome, and uveal melanoma). The instructions will generally include information about the use of the composition for the treatment or prevention of the GNAQ R183Q mutation-associated disease. In other embodiments, the instructions include at least one of the following: description of puromycin or puromycin analog; dosage schedule and administration for treatment or prevention of vascular malformation or related conditions or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Cell Lines Expressing Mutant GNAQ

The present invention provides recombinant human embryonic kidney (HEK) or endothelial cell lines comprising an isolated polynucleotide encoding a GNAQ polypeptide comprising a R183Q mutation. Such cell lines may be useful for screening candidate agents that modulate vascular malformation or a related condition.

Those skilled in the field of molecular biology will understand that any of a wide variety of expression systems may be used to provide a cell line heterologously expressing GNAQ polypeptide comprising a R183Q mutation. The precise host cell used is not critical to the invention. A polypeptide of the invention may be produced in mammalian cells (e.g., HEK cells, endothelial cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987). In particular embodiments, the cells are transiently transfected with expression vectors for producing mutant GNAQ polypeptides. In particular embodiments, the cells are stably transfected with expression vectors for producing mutant GNAQ polypeptides. In particular embodiments, the cells are HEK293, HEK293T, EA.926, EA.hy 926, or HUVEC.

A variety of expression systems exist for heterologous expression of mutant GNAQ polypeptides. Expression vectors useful for producing such polypeptides include, without limitation, virus-derived vectors, e.g., vectors derived from viruses such as baculoviruses, papova viruses, such as SV40, vaccinia viruses, adenoviruses, fowl pox viruses, pseudorabies viruses and retroviruses, and vectors derived from combinations thereof. In particular embodiments, the vector is a lentivirus plasmid.

Screening Assays

Methods of the invention are useful for the high-throughput low-cost screening of candidate agents that modulate a GNAQ R183Q mutation-associated disease, such as vascular malformation. Screening assays of the invention are based, at least in part, on the discovery of a link between puromycin sensitivity and the GNAQ R183Q mutation. Cells with hyperactivating GNAQ mutations have increased vulnerability to puromycin; recognizing this is essential to efforts to establish and maintain stable cell lines with these mutations. The mutations altered expression of proteins impacting molecular pathways downstream of Gαq and critical to angiogenesis, cell differentiation and cell survival. Puromycin further altered expression of these proteins impacting proteins which offer insights into possible novel targets for drug development.

Without intending to be bound by theory, it is believed that puromycin sensitivity in GNAQ R183Q mutant cells is linked to the same cellular signaling pathway(s) implicated in vascular malformations and other GNAQ R183Q mutation-associated diseases. Thus, candidate drugs identified could prove useful for treatment of vascular malformations. In particular embodiments, the screening assay comprises (a) contacting a cell comprising a GNAQ polynucleotide or polypeptide having a R183Q mutation with puromycin and a candidate agent; and (b) comparing viability of the contacted cell with a reference level of viability. In particular embodiment, an alteration in viability indicates that the candidate agent modulates a GNAQ R183Q mutation-associated disease. In particular embodiments, an alteration in viability indicates that the candidate agent modulates a vascular malformation.

Results of studies herein also indicate that ID3, TSC22D3, and TEAD3 are linked to the same cellular signaling pathway(s) implicated in vascular malformations and other GNAQ R183Q mutation-associated diseases. Accordingly, the in another aspect, the invention provides a method of identifying an agent that modulates a vascular malformation or related condition, where the method contains the steps of (a) contacting a cell with a candidate agent, and (b) measuring a level or activity of a ID3, TSC22D3, or TEAD3 polynucleotide or polypeptide, where an alteration in the level or activity of the ID3, TSC22D3, or TEAD3 polynucleotide or polypeptide indicates that the candidate agent modulates a vascular malformation or related condition.

Cell lines according to the invention (e.g., HEK or endothelial cells comprising an isolated polynucleotide encoding a GNAQ polypeptide comprising a R183Q mutation) may be used in the screening assays. The viability of a cell contacted with a candidate agent may be measured using cell viability assays known in the art. Assays for measuring cell viability are known in the art, and are described, for example, by Crouch et al. (J Immunol. Meth. 160, 81-8); Kangas et al. (Med. Biol.62, 338-43, 1984); Lundin et al., (Meth. Enzymol.133, 27-42, 1986); Petty et al (Comparison of J. Biolum. Chemilum.10, 29-34, 1995); and Cree et al (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega). In particular embodiments, the cell viability is measured using an MTT assay.

One skilled in the art appreciates that the effects of a candidate agent on a cell is typically compared to a corresponding control cell not contacted with the candidate agent. Thus, the screening methods include comparing the proliferation of a cell comprising a GNAQ R183Q mutation contacted by a candidate agent to the proliferation of an untreated control cell. The viability of cells contacted with puromycin and a candidate agent may be compared with a reference level of viability. For example, a reference level of viability may be the viability of cells not contacted with the candidate agent and contacted with puromycin only. In particular embodiments, the alteration in viability is positive (i.e., cells contacted with the candidate agent and puromycin have increased viability compared to cells contacted with puromycin only). In particular embodiments, the alteration in viability is negative (i.e., cells contacted with the candidate agent and puromycin have decreased viability compared to cells contacted with puromycin only).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Cells Harboring GNAQ R183Q or Q209L Mutation had Increased Cell Death after Transfection with GNAQ R183Q or Q209L Construct Using Puromycin Selection In the process of establishing HEK and endothelial cell lines with the R183Q and Q209L GNAQ mutations, an unexpected finding which potentially has several important translational implications was stumbled upon. Wildtype, R183Q, and Q209L GNAQ mutants were inserted into a lentivirus-plasmid. The sequences were confirmed and after transfection, puromycin selection done to generate stable HEK (human embryonic kidney) and EA.296 (endothelial) cell lines. In the HEK293 cells, 90-100% of the cells with empty or WT GNAQ survived the selection whereas only 75% of the cells with the R183Q and 40% of the Q209L mutations survived the selection. In the EA.926 endothelial cells 100% of the cells with the empty or WT constructs, but only 30% of those with the R183Q and less than <5% of those with the Q209L survived the puromycin selection.

The amount of cell death after puromycin selection was unexpected. Without being bound by theory, it was possible that the cells did not tolerate the transfection with multiple copies of the GNAQ mutations. However, this much cell death with the transient transfection was not typically observed. Without intending to be bound by theory, it was also possible that puromycin was more toxic to cells with the mutations.

Example 2: Cell Viability Assay Results Indicate that a R183Q Mutation in GNAQ Conferred Increased Sensitivity to Puromycin in HEK293 Cells To determine whether mutations in GNAQ conferred increased sensitivity to puromycin, an MTT (3-(4,5-dimethylthiazol-2-yl)-2,5-diphenyltetrazolium bromide) assay dose response curve was done with HEK239 cells (including standard curve and normalization) after transient transfection. Puromycin exposure in HEK293 cells transiently transfected with R183Q or Q209L (no puromycin selection) over greater than a 100 fold dose range was then tested.

FIG. 1 shows the impact of puromycin upon cell survival, over a 100 fold range of concentrations. Results of the MTT assay showed that, compared to cells with the empty or WT constructs, cells with the mutant constructs had decreased survival after exposure to a lower dose. Half maximal inhibitory concentration ($IC_{50}$) for puromycin inhibition of cell growth was decreased in R183Q and Q209L mutant cells compared to cells with empty and wildtype constructs.

The assays were performed according to the methods described below.

MTT Assay Methods

HEK 293 cells ($5 \times 10^5$ cells/well) in 6 well-plates were transient transfected with 1 μg of construct (pcDNA3.1-GNAQ, pcDAN3.1-R183Q and pcDNA3.1-Q209L) per well. Twenty-four (24) hours later, the cells were digested, counted and aliquoted into 24 well plates ($0.8 \times 10^5$ cells/well). After another 24 hours, the transfected cells were incubated with various concentrations of puromycin.

Three days later, the relative cell numbers were detected using MTT assay reagents (CellTiter 96® Aqueous One Solution Cell Proliferation Assay Reagents) as follows. After being thawed at room temperature, 40 μl the CellTiter 96® Aqueous One Solution Reagent was pipetted into each well of the 24-well assay plate containing the samples in 200 μl of culture medium. Then, the plates were incubated at 37° C. for 2 hours in a humidified, 5% $CO_2$ atmosphere. The supernatants were transferred into 96-well plates. The absorbance at 490 nm of each sample was read by using a plate reader (SpectraMax M5). Optical density directly correlated with viable cell quantity.

Controls

Percent maximal response to puromycin (change in cell number) in the cells transfected with the R183Q mutation was compared to that in cells with the empty and those with the wildtype construct. Comparisons were made to that in cells with the other activating Q209L mutation (positive control).

Statistical and Data Analyses

A software program (GraphPad Prism) was used to generate Dose Response Curves. A non-linear regression was done to graph the Log [puromycin molar concentration] versus Maximal Inhibitory Response. The GraphPad program was used to calculate the $IC_{50}$ of puromycin for each cell line (dose that gives a 50% maximal response) and the 95% confidence intervals. A 2-way ANOVA (Dose by Construct) was done to determine if there is a significant effect of construct upon puromycin effect with p-value of <0.05 used to determine significance.

Example 3: Viability Assays to Confirm that Mutation R183Q in GNAQ in Various Cell Lines Cells Results in an Increased Sensitivity to Puromycin To confirm that the R183Q mutation in GNAQ confers increased sensitivity to puromycin, the assay performed in Example 2 is repeated and additional cell viability assays are performed using various cell lines. HEK293T cells plated in 48 well plates are transiently transfected with empty, wild-type, R183Q, and Q209L (positive control) constructs and 24 hours later are exposed to puromycin for 1-4 days. A standard curve is first done to determine the range of cell numbers over which the assay is sensitive. All data is normalized to an internal experimental standard. Samples are analyzed on a 48 well plate reader (SpectraMax 5M) available to the lab by a researcher who is blinded to the construct and treatment identity of the samples. Ten (10) to twenty (20) different concentrations (including 0) of puromycin are tested in duplicate by MTT ((3-(4,5-dimethylthiazol-2-yl)-2,5-diphenyltetrazolium bromide)) assay in order to obtain a dose response curve plotting the % Maximal Response (change in cell number) versus the Log [drug concentration, in M] over a 100-fold concentration change. The dose response curve experiment is repeated a second time.

The MTT assay using EA.hy 926 endothelial cells, which are commercially available and widely used to study endothelial cell biology and function, are assayed as described above with the HEK293 cells. The same controls and experimental approach are also used to obtain a dose response curve for puromycin in these cells. The MTT assay may also be done with another commercially available endothelial cell line such as HUVEC cells.

Example 4: Puromycin Vulnerability in GNAQ Mutants

Puromycin vulnerability in GNAQ mutants was further investigated herein. pcDNA3.1-GNAQ, pcDNA3.1-R183Q, and GNAQ-Q209L were inserted into lentivirus-plasmids G3.3, which has Puromycin selection to generate G3.3-Gnaq, G3.3-R183Q, G3.3-Q209L (Comi lab). Then G3.3-Gnaq, G3.3-R183Q, G3.3-Q209L were used to produce lentivirus particles which were used to infect either HEK 293T cells or EA.hy926 cells. After being infected, the target cells were selected with 2 ug/ml puromycin (FIGS. 2A-2D). Only about 75% of the HEK 293T cells with the R183Q and only about 40% of the HEK 293T cells (FIG. 2A) with the Q209L mutation survived puromycin selection, and only about 30% of the EA.hy926 cells with the R183Q and less than 5% of the EA.hy926 cells with the Q209L mutation (FIG. 2B) survived the selection, whereas the stably transfected Empty and wild-type GNAQ cells demonstrated high survival. Furthermore, the mutants expressed lower levels of Gαq protein, while the cells with empty and wildtype constructs expressed higher levels of Gαq protein expression (FIG. 2C). Both HEK and endothelial cells with the mutant constructs grew more slowly than wildtype and demonstrated a more balled-up phenotype (FIG. 2D shows this morphology in transiently transfected cells; the endothelial cells with the Q209L mutation hardly grew at all.

Problems with the human mammary epithelial cell (HMEC) transfections (Table 1) were noted after failure to detect any induction of GNAQ by Western blots from most of the HMEC clones tested from infection 3. The clones were then examined for the presence of the full length GNAQ by PCR and only ~25% of the clones contained full length plasmid-GNAQ. Of these few clones, stable, inducible GNAQ expression was seen only in 4 WT clones, 1-2 R183Q clones and 1-2 Q209L clones. The WT expression was always more robust than the mutant clones. Also, the morphology and growth patterns of the mutant clones, particularly of the Q209L clones, were noticeably different than the WT clones which themselves grew more slowly than the HMEC parent cells. These finding were utilized to modify ongoing attempts to establish stable endothelial cell lines using a Tet-ON system. With removal of puromycin from the media, these efforts which had previously resulted in non-viable cells or poor Gαq expression were quickly successful.

Figure 3B:
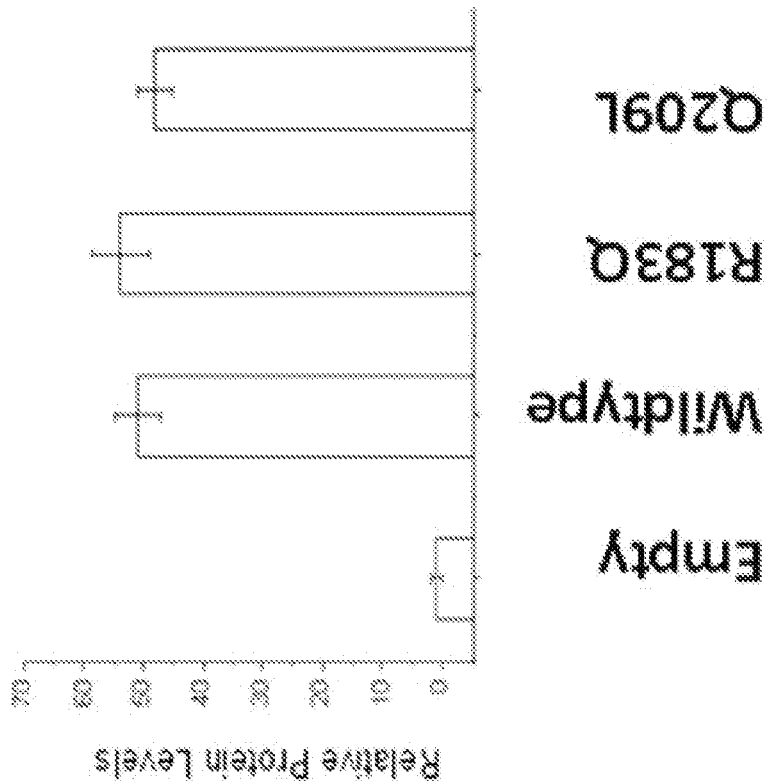
FIGS. 3A-3B are an image and plot showing overexpression of Gαq after transfection with GNAQ constructs. HEK 293T cells in six well plates were transiently transfected with pcDNA3.1-E, pcDNA3.1-GNAQ, pcDNA3.1-R183Q, pcDNA3.1-Q209L. 24 hours later, cells were digested and re-plated into 6-well plates. 24 hours later, the plates were incubated in DMEM (10% FBS). Three days later, protein was isolated. Gαq overexpression was demonstrated in cells transfected with the WT and mutant constructs.
Figure 3A:
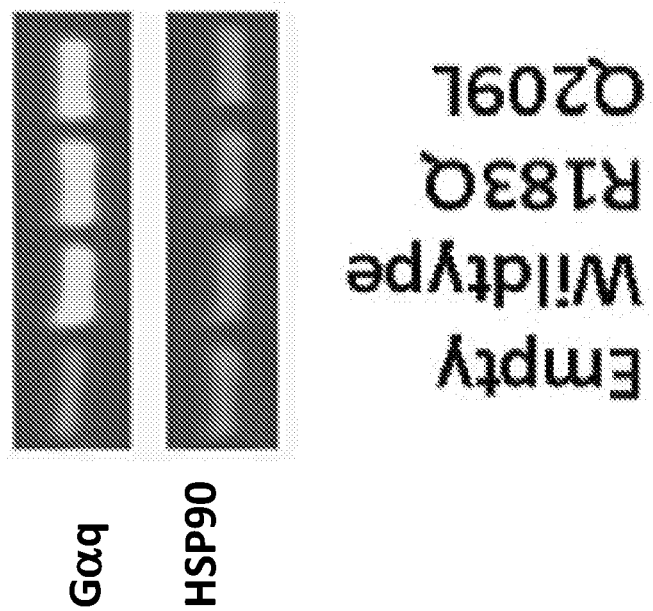
Figure 4A:
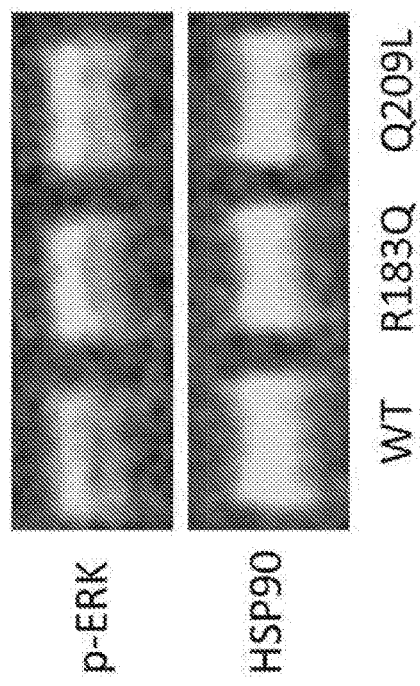
FIGS. 4A-4B are an image and plot showing phosphorylated ERK in HEK 293T cells transiently transfected with GNAQ constructs.
Figure 4B:
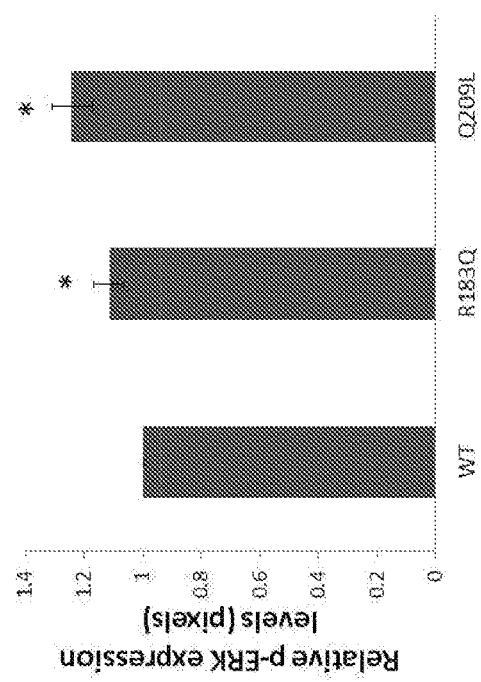

Overexpression of Gαq and p-ERK in HEK293T Cells Transiently Transfected with WT and Mutant GNAQ To assess the protein levels of Gαq in HEK293T cells transiently transfected with these plasmids, western blot analysis was performed (FIGS. 3A-3B) on the protein samples; data shown is from protein gathered for the 3 experiments for RNA and western analyses. The western blot analysis results demonstrated that protein levels of Gαq were significantly up-regulated (FIGS. 3A-3B, p<0.05) in HEK293T cells with WT or mutant constructs, compared to cells with the empty construct. p-ERK expression was also significantly increased in the mutants compared to WT (FIGS. 4A-4B).

GNAQ Mutations are More Sensitive to Puromycin

Figure 5:
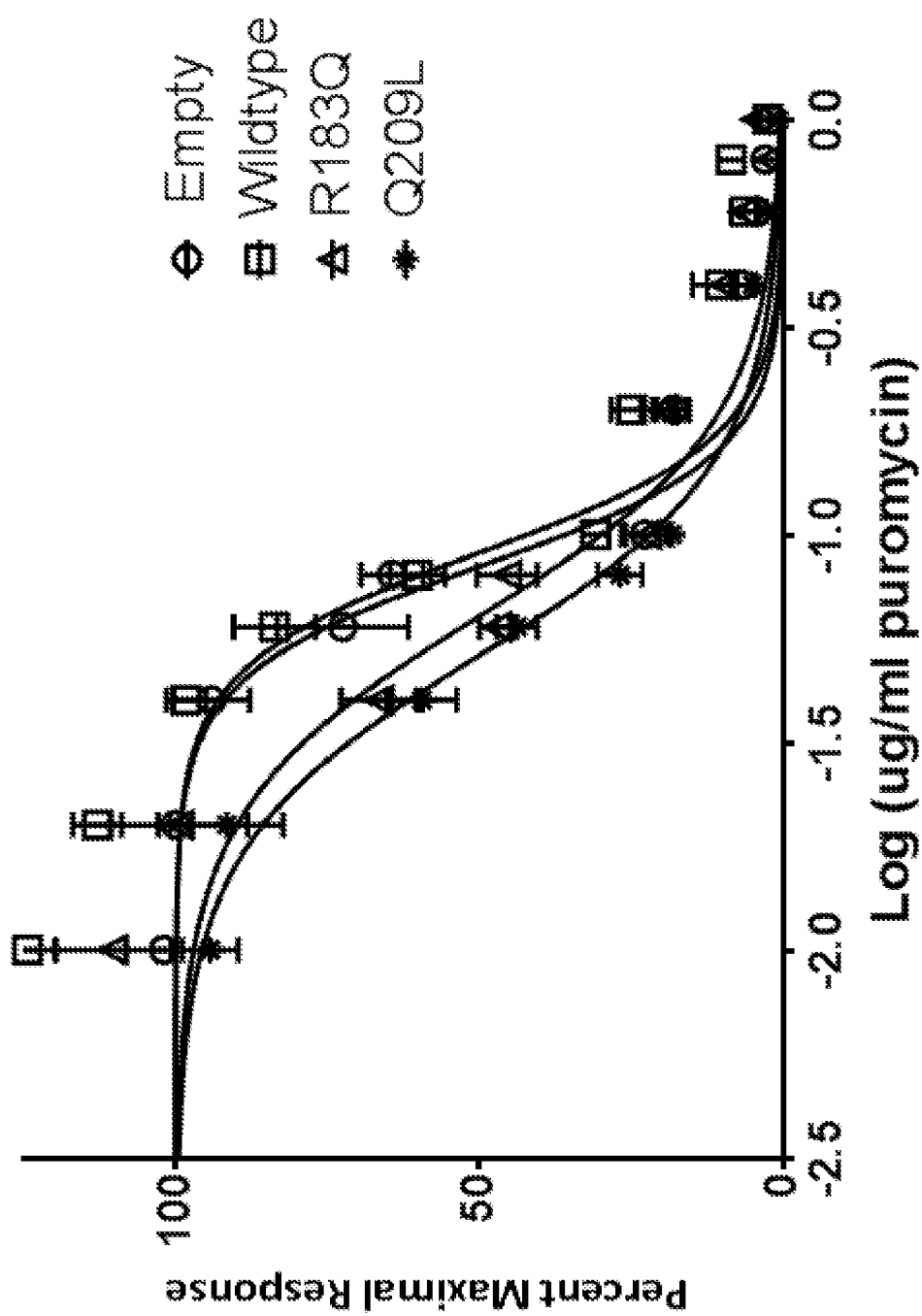
FIG. 5 is a plot showing a dose response curve for puromycin. HEK 293T cells ($5 \times 10^5$ cells/well in six-well plate) were transiently transfected with pcDNA3.1-E, pcDNA3.1-GNAQ, pcDNA3.1-R183Q, pcDNA3.1-Q209L. Twenty-four (24) hours later, the cells were digested, counted and aliquoted into 96-well plates. Twenty-four (24) hours later, the cells were incubated with a series of puromycin concentrations. Three days later, the relative cell numbers were detected using a cell proliferation assay.

A dose response curve (cell number in response to puromycin concentration) for HEK293T cells transiently transfected pcDNA3.1-E, pcDNA3.1-GNAQ, pcDNA3.1-R183Q and pcDNA3.1-Q209L and treated with puromycin is shown in FIG. 5. Cells expressing either the pcDNA3.1-R183Q or pcDNA3.1-Q209L plasmids were more sensitive to puromycin compared with cells transfected with the pcDNA3.1-E or pcDNA3.1-GNAQ plasmids. The half maximal inhibitory concentration (IC50) of puromycin for cells with the pcDNA3.1-R183Q was 0.064 µg/ml (95% CI 0.053 to 0.077 ug/ml) and for pcDNA3.1-Q209L was 0.051 µg/ml (95% CI 0.046 to 0.058 µg/ml) while for cells with pcDNA3.1-E it was 0.084 µg/ml (95% CI 0.074 to 0.095 µg/ml) and for the cells with the pcDNA3.1-GNAQ it was 0.091 µg/ml (95% CI 0.072 to 0.114 µg/ml).

Real Time PCR Results

Figure 6A:
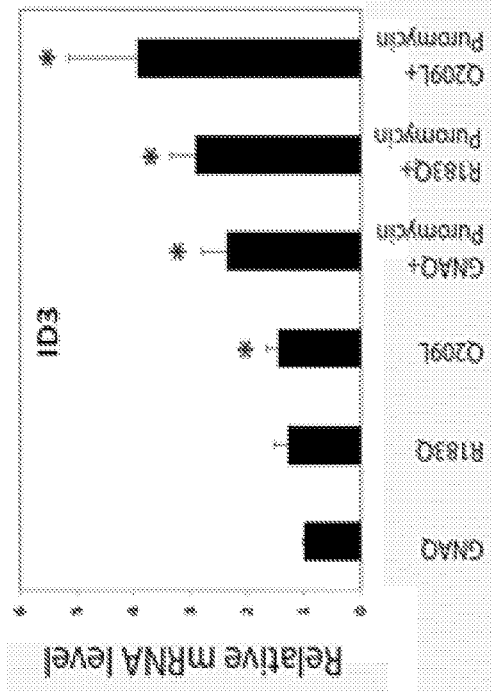
FIGS. 6A-6F are plots showing gene expression in WT and GNAQ mutant cells with and without puromycin. A panel of genes, important to the regulation of the pathways downstream of GNAQ, were evaluated by RT-PCR in mRNA samples gathered from cells with the pcDNA3.1-E, pcDNA3.1-GNAQ, pcDNA3.1-R183Q or pcDNA3.1-Q209L plasmids with or without puromycin treatment.
Figure 6B:
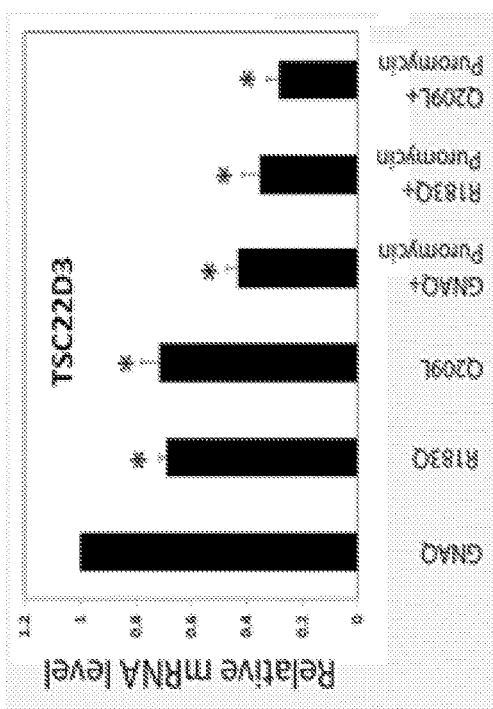

A panel of genes, important to the regulation of the pathways downstream of GNAQ, were evaluated by RT-PCR in mRNA samples gathered from cells with the pcDNA3.1-E, pcDNA3.1-GNAQ, pcDNA3.1-R183Q or pcDNA3.1-Q209L plasmids with or without puromycin treatment of 0.04 ug/ul (FIGS. 6A-6F, n=3 per group from 3 separate experiments). In cells expressing either R183Q or Q209L, the mRNA levels of TSC22D3 were down-regulated compared to empty or wildtype plasmid (vehicle treated). Treatment with puromycin was associated with decreased TSC22D3 mRNA expression (compared to vehicle treated wildtype), while treatment of cells expressing the R183Q or Q209L plasmids was associated with further decreased mRNA levels of TSC22D3 (FIG. 6A). mRNA levels of ID3 was up-regulated in cells overexpressing Q209L, and was also up-regulated in wildtype cells treated by puromycin (compared to vehicle treated). ID3 was also upregulated in cells expressing either 183Q and Q209L mutant Gαq treated with puromycin (compared to wildtype puromycin treated and to vehicle treated mutant cells; FIG. 6B).

Figure 6C:
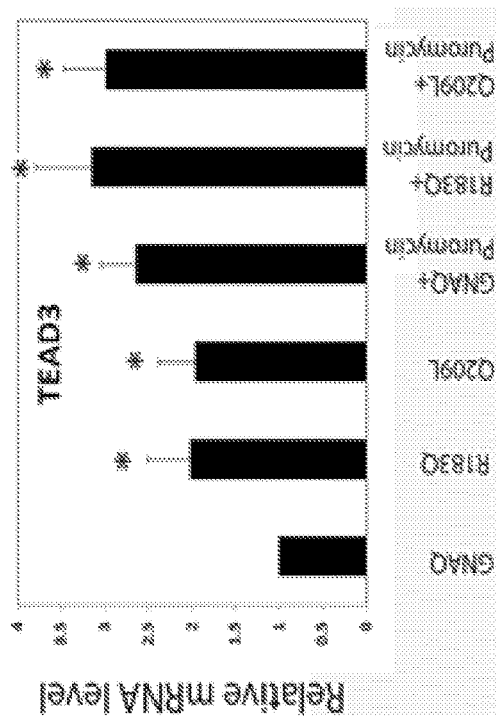
Figure 6D:
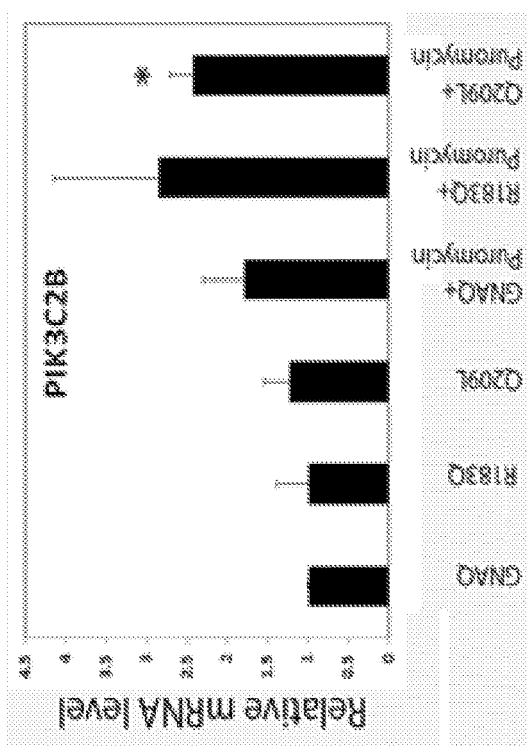
Figure 6F:
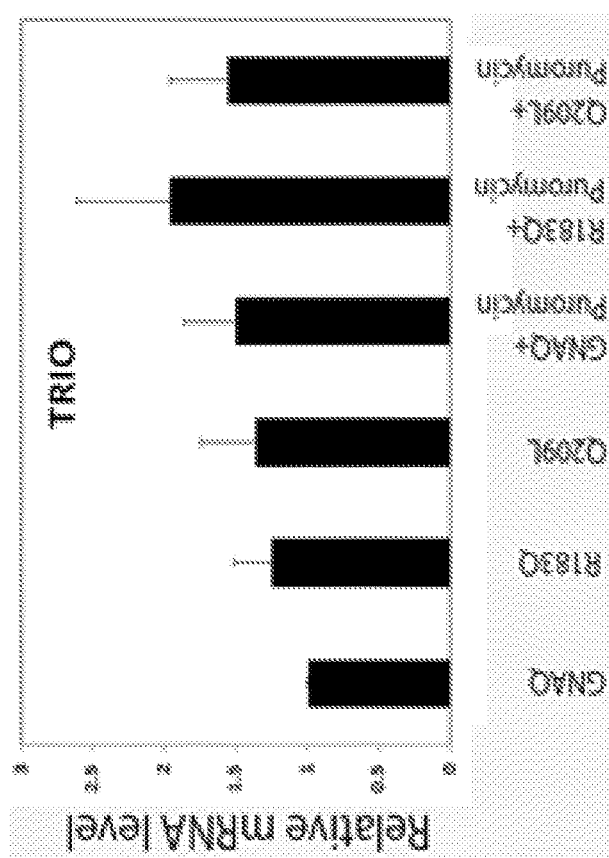
Figure 6E:
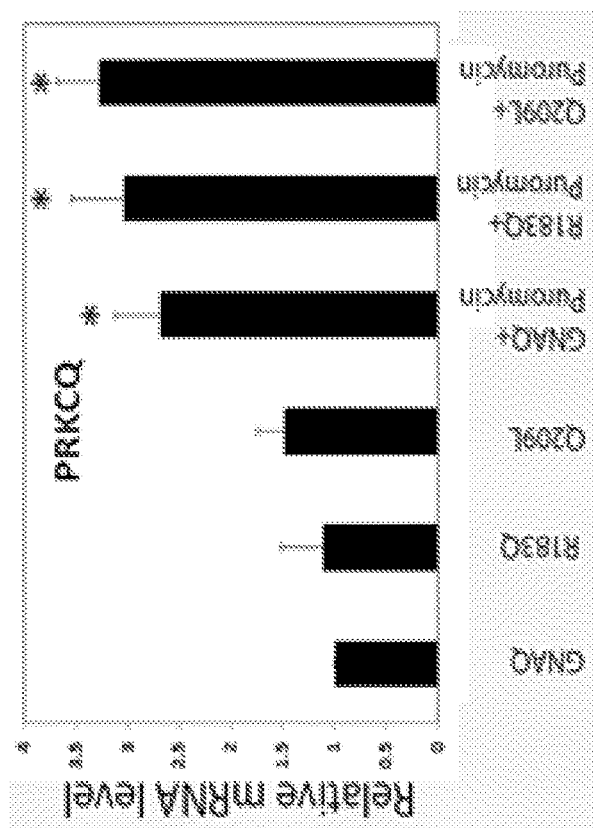

Furthermore, both R183Q and Q209L mutants were associated with significantly up-regulated mRNA levels of TEAD3 (P-value<0.05) compared to HEK293T cells with wildtype construct (FIG. 6D). PIK3C2B (FIG. 6C), PRKCQ (FIG. 6E), and TRIO (FIG. 6F) levels were increased compared to wildtype but not significantly. Levels of these transcripts were up-regulated in all three constructs by puromycin alone, but only significantly for TEAD3 and PRKCQ (FIG. 6E), and for PIK3C2B in Q209L cells treated with puromycin (FIG. 6C).

Western Results

Figure 7:
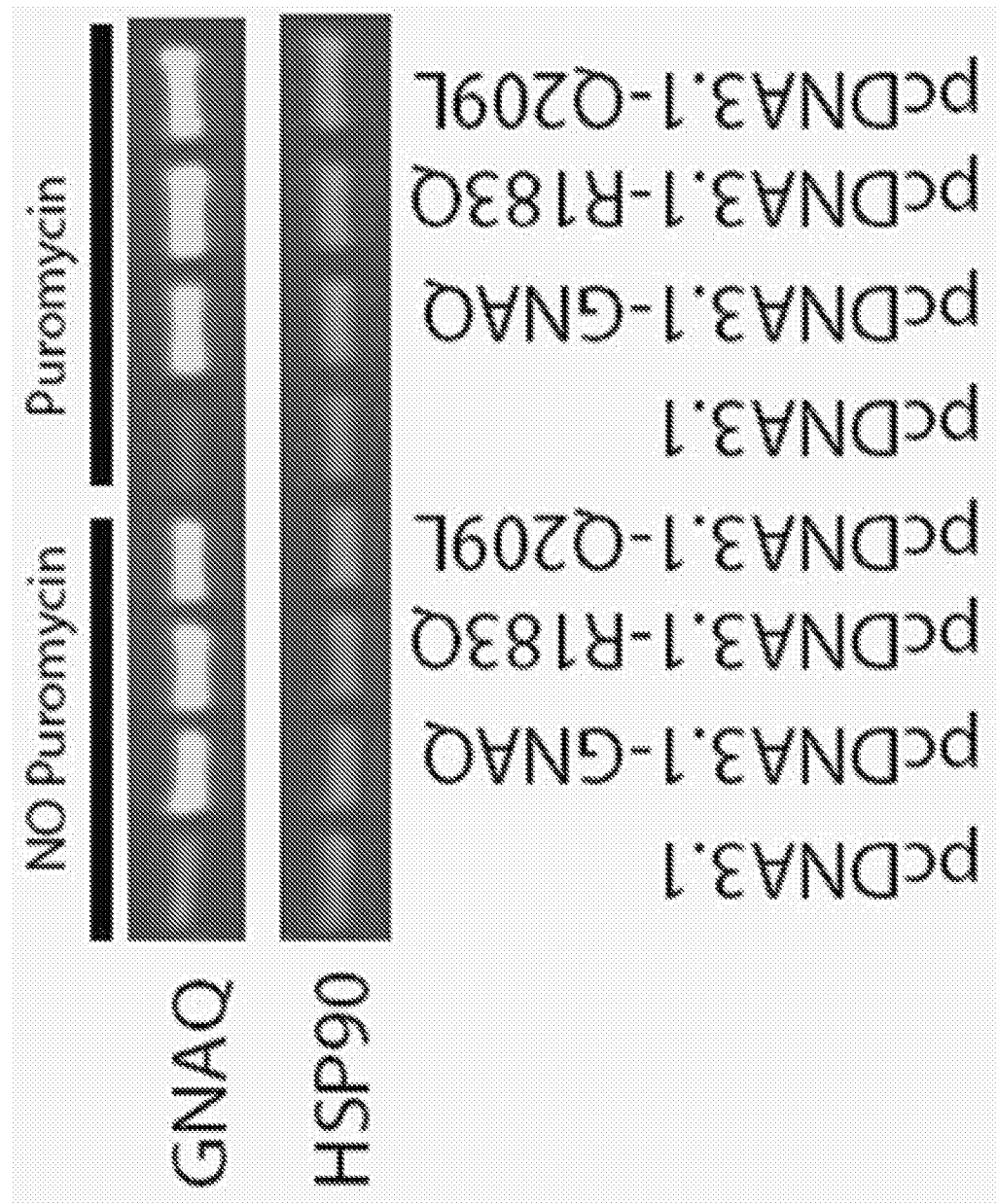
FIG. 7 is a Western blot showing Gαq expression after puromycin treatment. Gαq protein expression was evaluated by RT-PCR in samples gathered from cells with the pcDNA3.1-E, pcDNA3.1-GNAQ, pcDNA3.1-R183Q or pcDNA3.1-Q209L plasmids with or without puromycin treatment. Cells with all GNAQ constructs treated with puromycin expressed similar levels of puromycin compared to untreated cells.

No significant differences were observed in Gαq levels between the puromycin and vehicle treated cells, and no difference in molecular weight of Gαq was noted in any of the cells treated with puromycin, either wildtype or empty (FIG. 7). Protein levels of ID3 in R183Q and Q209L cells further increased with puromycin treatment in all three groups (pcDNA3.1-GNAQ, pcDNA3.1-R183Q or pcDNA3.1-Q209L).

Immunohistochemistry Results

Figure 8A:
FIGS. 8A-8C are images and a plot showing p-ERK immunohistochemistry and p-ERK expression in SWS leptomeningeal vessel endothelial cells.
Figure 8A:
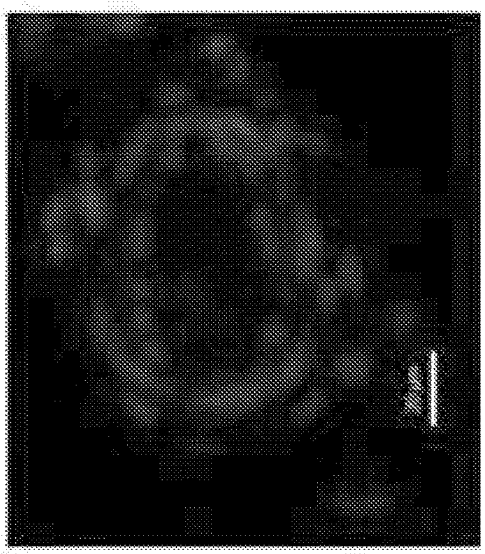
Figure 8A:
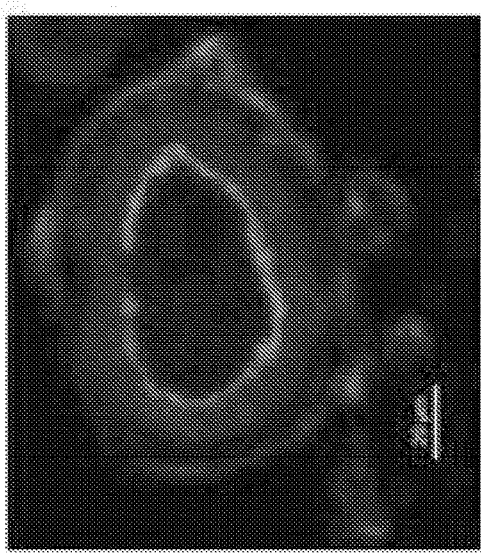
Figure 8B:
Figure 8B:
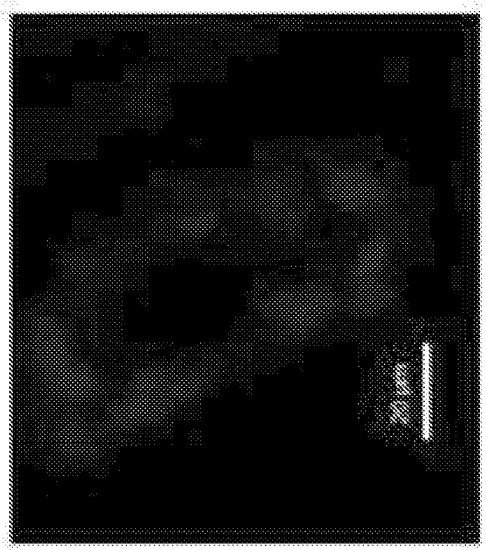
Figure 8B:
Figure 8C:
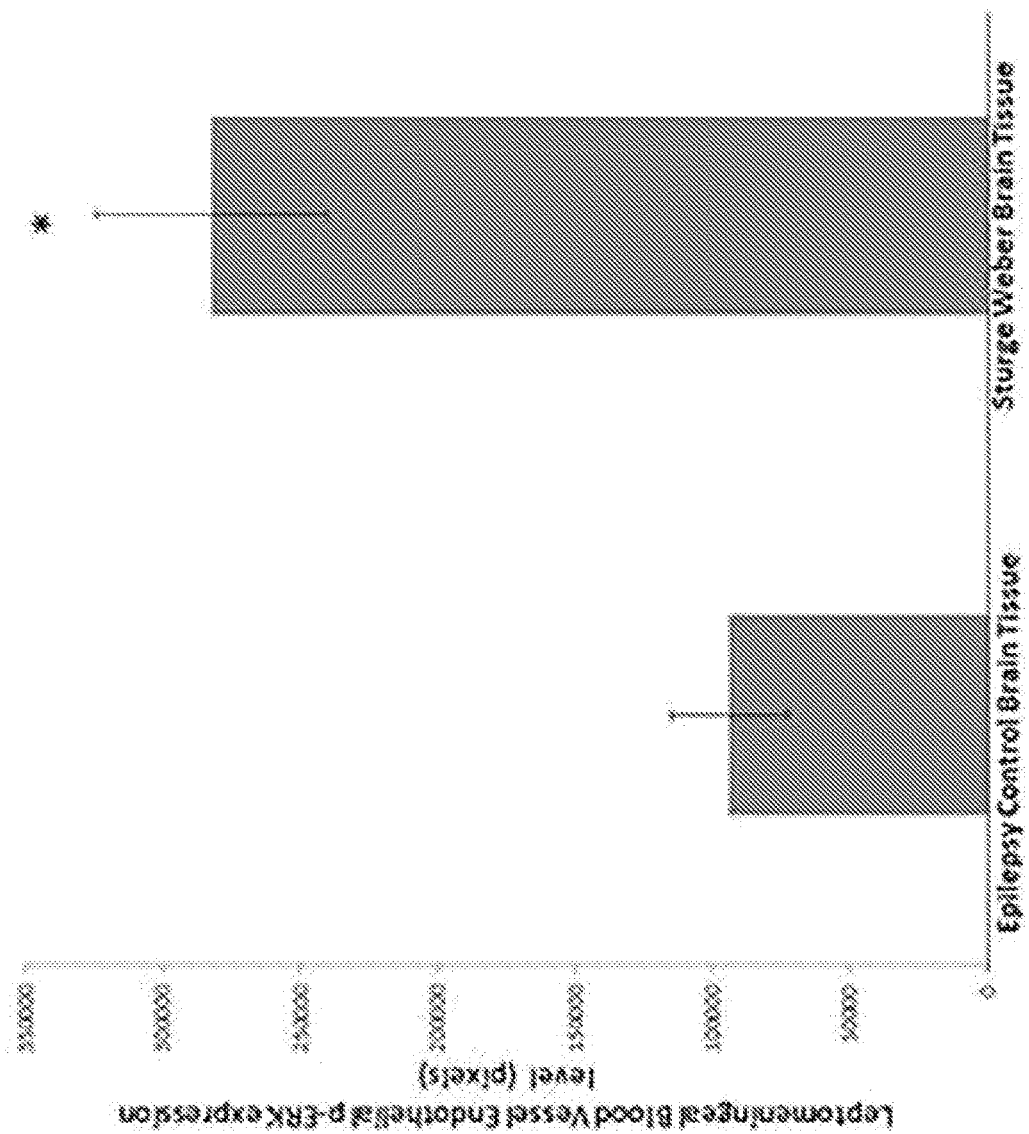

Disrupted organization of blood vessel cellular structure was noted on a-tubulin immunohistochemistry, and discontinuity of CD34+ labeling of SWS leptomeningeal blood vessels compared to vessels from epilepsy controls was noted. Blood vessels in Sturge-Weber brain tissue samples had significantly higher p-ERK expression in the endothelial cells of leptomeningeal vessels than epilepsy control samples (28,2192±SEM16,8902 vs. 9,4042±SEM 4,7340, p<0.05 (FIGS. 8A-8C).

Results described herein were obtained using the following methods and materials.

GNAQ and Mutant Plasmids

The plasmids of wild type GNAQ its mutations (pcDNA3.1-GNAQ, pcDAN3.1-R183Q and pcDNA3.1-Q209L) were generously provided by Dr. Kun-Liang Guan (Department of Pharmacology, University of California San Diego, USA). The empty plasmid (pcDNA3.1E) was constructed from pcDNA3.1-GNAQ by cutting the cDNA of GNAQ out with PmeI, and then the backbone of pcDNA3.1 was ligated. All GNAQ WT and mutant plasmids (pcDNA3.1-R183Q, pcDNA3.1-Q209L) were sequenced with CMV promoter as forward primer and BGH sequence as reverse primer and the correct mutation sites were confirmed. Sequence results are provided below:

GNAQ Wild type forward
(SEQ ID NO: 10)
NNNNNNNNNNNNNNNNNNNGAGCTCTCTGGCTAACTAGAGAACCCACTGC

TTACTGGCTTATCGAAATTAATACGACTCACTATAGGGAGACCCAAGCT

GGCTAGCGTTTAAACTTAAGCTTGGTACCACCATGACTCTGGAGTCCAT

CATGGCGTGCTGCCTGAGCGAGGAGGCCAAGGAAGCCCGGCGGATCAAC

GACGAGATCGAGCGGCAGCTCCGCAGGGACAAGCGGGACGCCCGCCGGG

AGCTCAAGCTGCTGCTGCTCGGGACAGGAGAGAGTGGCAAGAGTACGTT

TATCAAGCAGATGAGAATCATCCATGGGTCAGGATACTCTGATGAAGAT

AAAAGGGGCTTCACCAAGCTGGTGTATCAGAACATCTTCACGGCCATGC

AGGCCATGATCAGAGCCATGGACACACTCAAGATCCCATACAAGTATGA

GCACAATAAGGCTCATGCACAATTAGTTCGAGAAGTTGATGTGGAGAAG

GTGTCTGCTTTTGAGAATCCATATGTAGATGCAATAAAGAGTTTATGGA

ATGATCCTGGAATCCAGGAATGCTATGATAGACGACGAGAATATCAATT

ATCTGACTCTACCAAATACTATCTTAATGACTTGGACCGCGTAGCTGAC

CCTGCCTACCTGCCTACGCAACAAGATGTGCTTAGAGTTCGAGTCCCCA

CCACAGGGATCATCGAATACCCCTTTGACTTACAAAGTGTCATTTTCAG

AATGGTCGATGTAGGGGGCCAAAGGTCAGAGAGAAGAAAATGGATACAC

TGCTTTGAAAATGTCACCTCTATCATGTTTCTAGTAGCGCTTAGTGAAT

ATGATCAAGTTCTCGTGGAGTCAGACAATGAGAACCGAATGGAGGAAAG

CAAGGCTCTCTTTAGAACAATTATCACATACCCCTGGTTCCAGAACTCC

TCGGTTATTCTGTTCTTAAACAAGAAAGATCTTCTAGAGGAGAAAATCA

TGTATTCCCATCTAGTCGACTACTTCCCAGAATATGATGGACCCCAGAG

AGATGCCCAGGCAGCCCGAGA

Wild type reverse
(SEQ ID NO: 11)
GGCGGATCAACGACGAGATCGAGCGGCAGCTCCGCAGGGACAAGCGGGAC

GCCCGCCGGGAGCTCAAGCTGCTGCTGCTCGGGACAGGAGAGAGTGGCAA

GAGTACGTTTATCAAGCAGATGAGAATCATCCATGGGTCAGGATACTCTG

ATGAAGATAAAAGGGGCTTCACCAAGCTGGTGTATCAGAACATCTTCACG

GCCATGCAGGCCATGATCAGAGCCATGGACACACTCAAGATCCCATACAA

GTATGAGCACAATAAGGCTCATGCACAATTAGTTCGAGAAGTTGATGTGG

AGAAGGTGTCTGCTTTTGAGAATCCATATGTAGATGCAATAAAGAGTTTA

TGGAATGATCCTGGAATCCAGGAATGCTATGATAGACGACGAGAATATCA

ATTATCTGACTCTACCAAATACTATCTTAATGACTTGGACCGCGTAGCTG

ACCCTGCCTACCTGCCTACGCAACAAGATGTGCTTAGAGTTCGAGTCCCC

ACCACAGGGATCATCGAATACCCCTTTGACTTACAAAGTGTCATTTTCAG

AATGGTCGATGTAGGGGGCCAAAGGTCAGAGAGAAGAAAATGGATACACT

GCTTTGAAAATGTCACCTCTATCATGTTTCTAGTAGCGCTTAGTGAATAT

GATCAAGTTCTCGTGGAGTCAGACAATGAGAACCGAATGGAGGAAAGCAA

GGCTCTCTTTAGAACAATTATCACATACCCCTGGTTCCAGAACTCCTCGG

TTATTCTGTTCTTAAACAAGAAAGATCTTCTAGAGGAGAAAATCATGTAT

TCCCATCTAGTCGACTACTTCCCAGAATATGATGGACCCCAGAGAGATGC

CCAGGCAGCCCGAGAATTCATTCTGAAGATGTTCGTGGACCTGAACCCAG

ACAGTGACAAAATTATCTACTCCCACTTCACGTGCGCCACAGACACCGAG

AATATCCGCTTTGTCTTTGCTGCCGTCAAGGACACCATCCTCCAGTTGAA

CCTGAAGGAGTACAATCTGGTCTAACTCGAGTCTAGNGNNNNNNNNNNNN

183 Forward
(SEQ ID NO: 12)
NNNNNNNNNNNNNNNCTTNNNCTTGGTACCNCCATGACTCTGGAGTCCATCA

TGGCGTGCTGCCTGAGCGAGGAGGCCAAGGAAGCCCGGCGGATCAACGAC

GAGATCGAGCGGCAGCTCCGCAGGGACAAGCGGGACGCCCGCCGGGAGCT

CAAGCTGCTGCTGCTCGGGACAGGAGAGAGTGGCAAGAGTACGTTTATCA

AGCAGATGAGAATCATCCATGGGTCAGGATACTCTGATGAAGATAAAAGG

GGCTTCACCAAGCTGGTGTATCAGAACATCTTCACGGCCATGCAGGCCAT

GATCAGAGCCATGGACACACTCAAGATCCCATACAAGTATGAGCACAATA

AGGCTCATGCACAATTAGTTCGAGAAGTTGATGTGGAGAAGGTGTCTGCT

TTTGAGAATCCATATGTAGATGCAATAAAGAGTTTATGGAATGATCCTGG

AATCCAGGAATGCTATGATAGACGACGAGAATATCAATTATCTGACTCTA

CCAAATACTATCTTAATGACTTGGACCGCGTAGCTGACCCTGCCTACCTG

CCTACGCAACAAGATGTGCTTAGAGTTCAAGTCCCCACCACAGGGATCAT

CGAATACCCCTTTGACTTACAAAGTGTCATTTTCAGAATGGTCGATGTAG

GGGGCCAAAGGTCAGAGAGAAGAAAATGGATACACTGCTTTGAAAATGTC

ACCTCTATCATGTTTCTAGTAGCGCTTAGTGAATATGATCAAGTTCTCGT

GGAGTCAGACAATGAGAACCGAATGGAGGAAAGCAAGGCTCTCTTTAGAA

CAATTATCACATACCCCTGGTTCCAGAACTCCTCGGTTATTCTGTTCTTA

AACAAGAAAGATCTTCTAGAGGAGAAAATCATGTATTCCCATCTAGTCGA

CTACTTCCCAGAATATGATGGACCCCAGAGAGATGCCCAGGCAGCCCGAG

AATTCATTCTGAAGATGTTCGTGGACCTGAACCCAGACAGTGACAAAATT

ATCTACTCCCACTTCACGTGCGCCACAGACACCGAGAATATCCGCTTTGT

183 Reverse
(SEQ ID NO: 13)
GATCAACGACGAGATCGAGCGGCAGCTCCGCAGGGACAAGCGGGACGCCC

GCCGGGAGCTCAAGCTGCTGCTGCTCGGGACAGGAGAGAGTGGCAAGAGT

ACGTTTATCAAGCAGATGAGAATCATCCATGGGTCAGGATACTCTGATGA

AGATAAAAGGGGCTTCACCAAGCTGGTGTATCAGAACATCTTCACGGCCA

TGCAGGCCATGATCAGAGCCATGGACACACTCAAGATCCCATACAAGTAT

GAGCACAATAAGGCTCATGCACAATTAGTTCGAGAAGTTGATGTGGAGAA

GGTGTCTGCTTTTGAGAATCCATATGTAGATGCAATAAAGAGTTTATGGA

-continued

```
ATGATCCTGGAATCCAGGAATGCTATGATAGACGACGAGAATATCAATTA

TCTGACTCTACCAAATACTATCTTAATGACTTGGACCGCGTAGCTGACCC

TGCCTACCTGCCTACGCAACAAGATGTGCTTAGAGTTCAAGTCCCCACCA

CAGGGATCATCGAATACCCCTTTGACTTACAAAGTGTCATTTTCAGAATG

GTCGATGTAGGGGGCCAAAGGTCAGAGAGAAGAAAATGGATACACTGCTT

TGAAAATGTCACCTCTATCATGTTTCTAGTAGCGCTTAGTGAATATGATC

AAGTTCTCGTGGAGTCAGACAATGAGAACCGAATGGAGGAAAGCAAGGCT

CTCTTTAGAACAATTATCACATACCCCTGGTTCCAGAACTCCTCGGTTAT

TCTGTTCTTAAACAAGAAAGATCTTCTAGAGGAGAAAATCATGTATTCCC

ATCTAGTCGACTACTTCCCAGAATATGATGGACCCCAGAGAGATGCCCAG

GCAGCCCGAGAATTCATTCTGAAGATGTTCGTGGACCTGAACCCAGACAG

TGACAAAATTATCTACTCCCACTTCACGTGCGCCACAGACACCGAGAATA

TCCGCTTTGTCTTTGCTGCCGTCAAGGACACCATCCTCCAGTTGAACCTG

AAGGAGTACAATCTGGTCTAACNNGANNNNNNNNNNNNNNNNNNNNNNNC
```

209 Forward
(SEQ ID NO: 14)

```
NNNNNNNNNNNNNNNNNNNNNANCTCTCTGGCTANCTAGAGAACCCACTGC

TTACTGGCTTATCGAAATTAATACGACTCACTATAGGGAGACCCAAGCTG

GCTAGCGTTTAAACTTAAGCTTGGTACCACCATGACTCTGGAGTCCATCA

TGGCGTGCTGCCTGAGCGAGGAGGCCAAGGAAGCCCGGCGGATCAACGACG

AGATCGAGCGGCAGCTCCGCAGGGACAAGCGGGACGCCCGCCGGGAGCTCA

AGCTGCTGCTGCTCGGGACAGGAGAGAGTGGCAAGAGTACGTTTATCAAGC

AGATGAGAATCATCCATGGGTCAGGATACTCTGATGAAGATAAAAGGGGCT

TCACCAAGCTGGTGTATCAGAACATCTTCACGGCCATGCAGGCCATGATCA

GAGCCATGGACACACTCAAGATCCCATACAAGTATGAGCACAATAAGGCTC

ATGCACAATTAGTTCGAGAAGTTGATGTGGAGAAGGTGTCTGCTTTTGAGA

ATCCATATGTAGATGCAATAAAGAGTTTATGGAATGATCCTGGAATCCAGG

AATGCTATGATAGACGACGAGAATATCAATTATCTGACTCTACCAAATACT

ATCTTAATGACTTGGACCGCGTAGCTGACCCTGCCTACCTGCCTACGCAAC

AAAGATGTGCTTAGAGTTCGAGTCCCCACCCAGGGATCATCGAATACCCCT

TTGACTTACAAAGTGTCATTTTCAGAATGGTCGATGTAGGGGGCCTAAGGT

CAGAGAGAAGAAAATGGATACACTGCTTTGAAAATGTCACCTCTATCATGT

TTCTAGTAGCGCTTAGTGAATATGATCAAGTTCTCGTGGAGTCAGACAATG

AGAACCGAATGGAGGAAAGCAAGGCTCTCTTTAGAACAATTATCACATACC

CCTGGTTCCAGAACTCCTCGGTTATTCTGTTCTTAAACAAGAAAGATCTTC

TAGAGGAGAAAATCATGTATTCCCATCTAGTCGACTACTTCCCAGAATATG

ATGGACCCCAGAGAGATGCCCAGGCAGCCCGAGA
```

209 Reverse
(SEQ ID NO: 15)

```
GGCGGATCAACGACGAGATCGAGCGGCAGCTCCGCAGGGACAAGCGGGAC

GCCCGCCGGGAGCTCAAGCTGCTGCTGCTCGGGACAGGAGAGAGTGGCAA

GTGAGTACTTATCAAGCAGATGAGAATCATCCATGGGTCAGGATACTCTG

ATGAAGATAAAAGGGGCTTCACCAAGCTGGTGTATCAGAACATCTTCACG
```

```
GCCATGCAGGCCATGATCAGAGCCATGGACACACTCAAGATCCCATACAA

GTATGAGCACAATAAGGCTCATGCACAATTAGTTCGAGAAGTTGATGTGG

AGAAGGTGTCTGCTTTTGAGAATCCATATGTAGATGCAATAAAGAGTTTA

TGGAATGATCCTGGAATCCAGGAATGCTATGATAGACGACGAGAATATCA

ATTATCTGACTCTACCAAATACTATCTTAATGACTTGGACCGCGTAGCTG

ACCCTGCCTACCTGCCTACGCAACAAGATGTGCTTAGAGTTCGAGTCCCC

ACCACAGGGATCATCGAATACCCCTTTGACTTACAAAGTGTCATTTTCAG

AATGGTCGATGTAGGGGGCCTAAGGTCAGAGAGAAGAAAATGGATACACT

GCTTTGAAAATGTCACCTCTATCATGTTTCTAGTAGCGCTTAGTGAATAT

GATCAAGTTCTCGTGGAGTCAGACAATGAGAACCGAATGGAGGAAAGCAA

GGCTCTCTTTAGAACAATTATCACATACCCCTGGTTCCAGAACTCCTCGG

TTATTCTGTTCTTAAACAAGAAAGATCTTCTAGAGGAGAAAATCATGTAT

TCCCATCTAGTCGACTACTTCCCAGAATATGATGGACCCCAGAGAGATGC

CCAGGCAGCCCGAGAATTCATTCTGAAGATGTTCGTGGACCTGAACCCAG

ACAGTGACAAAATTATCTACTCCCACTTCACGTGCGCCACAGACACCGAG

AATATCCGCTTTGTCTTTGCTGCCGTCAAGGACACCATCCTCCAGTTGAA

CCTGAAGGAGTACAATCGAGTCTAGNGNNCCNNNNNNN
```

Stable Transfection Experiments

Confluent GP2-293T cells in T75 flasks were transfected using LIPOFECTAMINE® transfection reagent with packaging vector (VSV-G) and plasmid containing either WT, R183Q or Q209L GNAQ. Supernatant containing virus was collected 48 hours later and filtered. HMECs, at ~50% confluent, were infected with viral supernatant and polybrene (Sigma-Aldrich Al-118) and then re-infected 24 hours later for a total infection time of 48 hours. Cells were grown to confluency then split 1:3. Puromycin was added at this point to select for transformed cells. The dosage was determined by a dose response curve performed in untransformed HMECs. 1 ug/ml killed 100% of the cells after 48 hours.

Transient Transfection

HEK293T cells (ATCC) ($5 \times 10^5$/well) plated in 6 well plates, which had been coated with poly-L-lysine (Sigma-Aldrich, P8920), were incubated at 37° C., 5% $CO_2$ overnight. On the second day, the plasmids of pcDNA3.1E, pcDNA3.1-GNAQ, pcDNA3.1-R183Q and pcDNA3.1-Q209L were transiently transfected into the HEK293T cells by using FUGENE 6® transfection reagent. For each plasmid, 1 μg plasmid DNA was added into 100 μl serum-free OPTI-MEM. 6 μl FUGENE 6® transfection reagent was added into 100 μl serum-free OPTI-MEM® medium. After being incubated for 5 minutes at room temperature, the diluted DNA and diluted FUGENE 6® transfection reagent were combined together and were incubated in hood for 15 min. Then, the DNA: FUGENE 6® transfection reagent mixture was added into HEK293T cells cultured in 2 ml of Dulbecco's Modified Eagle Medium (DMEM) without antibiotics. Plates were swirled to disperse mixture evenly. After being incubated at 37° C., 5% $CO_2$ for 24 hours, the transiently transfected cells were fed with 2 ml of fresh media.

Western Blot Assay

Treated cells were harvested with ice-cold radioimmuno-precipitation assay (RIPA) buffer (150 mM NaCl, 1.0% IGEPAL® CA-630, 0.5% sodium deoxycholate, 0.1% SDS, and 50 mM Tris, pH 8.0) (Sigma-Aldrich) plus phosphatase inhibitor cocktail (Cell signaling technology, #5870) and analyzed by western blot as follows: Quantitative protein samples were denatured in 4×LDS Sample buffer (Invitrogen) at 100° C. for 6 minutes. Samples were then subjected to SDS-PAGE by using Bio-Rad 4-15% gradient gels and transferred to PVDF membrane. The membranes were blocked with Li-cor ODYSSEY® Blocking buffer for 30 minutes at room temperature. Then the membranes were incubated with primary antibody (GaQ 1:125, Santa Cruz Biotechnology, sc-393; p-ERK 1:1000, Cell Signaling Technology, 4370; ERK 1:1000, Cell signaling Technology, 4696; HSP90 1:1000, Cell Signaling Technology, 4877) in a 1:1 solution of Li-cor ODYSSEY® blocking buffer and Tris-Buffered Saline and 0.1% Tween 20 (TBST) overnight at 4° C. The membranes were then washed three times for 10 min each in Tris-Buffered Saline and 0.1% Tween 20 (TBST) then probed with goat anti-mouse (IR-Dye 680RD) or goat anti Rabbit (IR-Dye-800CW) labeled secondary antibody in 1:1 Li-cor ODYSSEY® blocking buffer to TBST for 1 hour at room temperature. After being washed three times with TBST, the membranes were imaged using a Li-cor ODYSSEY® scanner. Bands were quantified using Image J software program.

MTT Assay

HEK293T cells ($5\times10^5$ cells/well) in 6 well-plates were transiently transfected with 1 µg (pcDNA3.1-E, pcDNA3.1-GNAQ, pcDAN3.1-R183Q and pcDNA3.1-Q209L) per well using FUGENE 6®. Twenty-four (24) hours later, the cells were digested, counted and aliquoted into 96-well plates ($1\times10^4$ cells/well). After another 24 hours, the transfected cells were incubated with a 100-fold concentration series of puromycin. Three days later, the relative cell numbers were detected using CELLTITER 96® Aqueous One Solution Cell Proliferation Assay Reagents (Promega #G3582) as follows: After being thawed at room temperature, 10 µl of CELLTITER 96® Aqueous One Solution Reagent was pipet into each well of the 96-well assay plate containing the samples in 100 µl of culture medium. Then, the plates were incubated at 37° C. for 2 hours in a humidified, 5% $CO_2$ atmosphere. The absorbance at 490 nm of each sample was read by using SpectraMAX M5. Readings were normalized to that in pcDNA3.1-GNAQ cells receiving vehicle. Results were analyzed in GraphPad. Experiment was done in quadruplicate samples.

RNA Isolation

HEK293T cells ($5\times10^5$ cells/well) were transfected with 1 µg plasmid (pcDNA3.1-GNAQ, pcDAN3.1-R183Q or pcDNA3.1-Q209L) in 6-well plates. Twenty-four (24) hours later, cells were digested and re-plated into 6-well plates. Twenty-four (24) hours later, the plates were incubated in DMEM (10% FBS) with or without 0.04 µg/ml puromycin. Three days later, total RNA of treated HEK293T cells were isolated by using RNEASY® Mini Kit (QIAGEN) as follows. Media was aspirated, and the cells washed twice with PBS. 350 µl Buffer RLT with B-Mercaptoethanol was added to the each well. The lysate was pipetted into a microcentrifuge tube and pipetted to mix. 1 volume of 70% ethanol was added to the lysate. Lysate was transferred to an RNEASY® spin column placed in a 2 ml collection tube (supplied) and centrifuged. RNEASY® spin column was washed as per kit instructions. 50 µl RNase-free water was added directly to the center of the spin column membrane which was centrifuged for 1 min at 12,000 rpm to elute the RNA. Three separate experiments were performed to obtain triplicate mRNA and protein samples for analysis.

Reverse Transcription

Reverse Transcription was carried out with the using the High Capacity cDNA Reverse Transcription Kits and based on Applied Biosystems' protocol. 2×RT master mix is prepared using the kit components before preparing the reaction plate and kit components allowed to thaw on ice. Referring to one reaction amount of components, the volume of components needed to prepare the required number of reactions was calculated. Then 10 µl of 2×RT master mixes was pipetted into each well of 500 µl PCR clean tubes. 10 µL of RNA sample (1 µg) was pipetted into each tube which is then mixed, centrifuged and then placed in a thermal cycler with the program of (10 min at 25° C., 120 min at 37° C., 5 min at 85° C., then 4° C.). After the thermal cycler, 1 µl RNase H was added into the tubes and incubated at 37° C. for 20 min. Finally, 600 µl Nuclease-free $H_2O$ was added into each tube.

Real Time PCR

The primers for Real-Time PCR were designed online with Primer-BLAST software tool. For each gene, at least three primers at different locations were designed based on the cDNA of the genes. The primer concentrations were normalized and were adjusted to 5 pmol/µl. The real-time PCR reaction mixture of 20 µl included 10 µl SYBR Green Mix (2×), 2 µl primer pair mix, and 8 µl diluted cDNA solution. The Real-time PCR of loaded samples were run on CFX Connect™ real-time PCR system (Bio-rad) with extension steps of (50° C. 2 min 1 cycle, 95° C. 10 min 1 cycle, 95° C. 15 sec then 60° C. 1 min 40 cycles, 72° C. 10 min, 1 cycle) followed by a melting curve analysis (from 55° C. to 95° C. increments 0.05° C./Sec) to guarantee absence of nonspecific amplification. The primers with a unique peak in melting curve were chosen for next step. The primers were also only used for next experiments after they were confirmed by obtaining the same results from other primers for the same gene. With the final confirmed primers, the RNA levels in triplicate samples, obtained from three separate experiments, were measured.

Immunohistochemistry

Series of slides from Sturge-Weber Syndrome fixed brain tissue and surgical epilepsy focal cortical dysplasia disease fixed control samples were deparaffinized with HemoDe solvent and rehydrated with ethanol. Antigen retrieval was then done for an hour at steaming temperature in 1× Citrate buffer. Slides were cooled, washed in TBS, blocked for nonspecific reactivity and then stained for CD34 and alpha-tubulin. The slides were incubated overnight at 4° C. in the primary antibodies; anti CD34 (rabbit monoclonal, 1:1000, Abcam Inc., Cambridge, Mass., Cat #ab81289) and alpha-tubulin (mouse monoclonal, 1:1000; Santa Cruz Biotechnology, Cat #sc-23948). The secondary antibodies were applied the next day; Alexa 594 (1:500; Invitrogen, Carlsbad, Calif.) for cells marked with CD34, and Alexa 488 (1:500; Invitrogen, Carlsbad, Calif.) for alpha-tubulin detection. Slides were coverslipped with prolong antifade medium with DAPI (Cell Signaling). Intact tissue (determine by robust alpha-tubulin staining and CD34 staining) were stained (adjacent sections) for p-ERK and total ERK using rabbit monoclonal Phospho-p44/42 MAPK (p-ERK, 1:100, Cell Signaling Technology, Cat #4370) and mouse p44/42 MAPK (Total ERK, 1:300, Cell Signaling Technology, Cat #4696). The secondary antibodies applied were Alexa 594 (1:500; Invitrogen, Carlsbad, Calif.) for cells marked with p-ERK, and Alexa 488 (1:500; Invitrogen, Carlsbad, Calif.) for total ERK detection.

p-ERK intensity levels in the endothelial cells of blood vessels in the leptomeninges were visualized using the AxioVision Apotome System microscope and software (Carl Zeiss MicroImaging). Representative images from the greatest p-ERK labeling seen in that brain section (2 fields of view/sample) were taken at 20× using standardized camera settings. Image J software was used to determine the average intensity density of all leptomeningeal vessels wholly contained within the field of view captured in each image. Each cross-sectional blood vessel image was traced on the inside of the blood vessel (inner most ring of the vessel) and was also traced on the outer aspect of the cross-sectional endothelial layer. The average intensity density of p-ERK labeling for the endothelial cell layer was measured by Image J software analysis. Student's t-test was used to compare the average intensity density in the SWS leptomeningeal vessels versus the epilepsy control leptomeningeal vessels ±SEM.

TABLE 1

Results of initial induction studies with human mammary epithelial cells (HMEC)

| Infection | Dosage of Puromycin | Clones | Dox induced | GNAQ expressing | Observations |
|---|---|---|---|---|---|
| 1 | 1 ug/ml | 0 | | | |
| 2 | 1 ug/ml | 0 | | | |
| 3 | 0.25 ug/ml, 0.33 ug/ml, 1 ug/ml, 0.5 ug/ml | ~50 of each (WT, RQ, QL) | WT - 16 RQ - 17 QL - 17 | WT - 1 RQ - 1 QL - 1 | Morphology of mutants different and they grew more slowly than WT |
| 4 | 1 ug/ml | WT - 16 RQ - 12 QL - 16 | | | |
| 5 | 1 ug/ml | 0 | | | |
| 6 | 1 ug/ml | WT - 15 RQ - 9 QL - 12 | WT - 12 RQ - 5 QL - 9 | WT - 3 RQ - 1 QL - 1 | Morphology of mutants different and they grew more slowly than WT |

TABLE 2

RT-PCR primer sequences

| Name | | Sequence | SEQ ID NO: |
|---|---|---|---|
| ID3 | Forward 1 | AGGTCACTGTAGCGGACTTC | 16 |
| ID3 | Reverse 1 | CTTCATGCTGGGGAGTGAGT | 17 |
| TSC22D3 | Forward 1 | TCTGTTTCGTGAAGGCAGGG | 18 |
| TSC22D3 | Reverse 1 | TGTAATCCCACACTGGGCTG | 19 |
| TEAD3 | Forward 3 | TTGTGTACCGTATCCACCGC | 20 |
| TEAD3 | Reverse 3 | TTCTCCAGCACGCTGTTCAT | 21 |
| TRIO | Forward 3 | GCACCATGTCCTGGATGTCA | 22 |
| TRIO | Reverse 3 | CCTGCTGGAAAACACACAGC | 23 |
| PRKCQ | Forward 4 | TCCAACTTTGACTGCGGGTC | 24 |
| PRKCQ | Reverse 4 | ACATCTGCCCGTTCTCTGAT | 25 |
| TAF15 | Forward 3 | ATGGAAATCCAGGCAGCCAA | 26 |
| TAF15 | Reverse 3 | TGTCCATAACTGGAGTAACCGC | 27 |
| PIK3C2B | Forward 1 | TTTGTGCTTTGGGGAGCAGA | 28 |
| PIK3C2B | Reverse 1 | GCTAAGGCTTCCTTCAGCCA | 29 |

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for treating a vascular malformation in a subject, wherein the vascular malformation comprises endothelial cells having a GNAQ R193Q or Q209L mutation, comprising the step of administering to the vascular malformation an effective amount of puromycin or puromycin analog.

2. The method of claim 1, wherein the vascular malformation comprises a capillary malformation, vascular malformation in the brain, vascular malformation in the eye, or a birthmark.

3. The method of claim 1, wherein the puromycin or puromycin analog is administered topically, orally, by injection, or by ocular administration.

4. The method of claim 1, wherein the subject is a human.

5. The method of claim 2, wherein the vascular malformation is a symptom of Sturge-Weber syndrome or uveal melanoma.

6. The method claim 1, further comprising administering laser treatment to the vascular malformation.

* * * * *

SEQUENCE LISTING

```
<160> NUMBER OF SEQ ID NOS: 29

<210> SEQ ID NO 1
<211> LENGTH: 359
<212> TYPE: PRT
<213> ORGANISM: Homo sapiens

<400> SEQUENCE: 1

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95
```

-continued

```
Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355
```

```
<210> SEQ ID NO 2
<211> LENGTH: 6343
<212> TYPE: DNA
<213> ORGANISM: Homo sapiens

<400> SEQUENCE: 2
```

| | | |
|---|---|---|
| agactatccg ctcccaccgc gcccccggcc cacctggtgg ccccggccct ggccgccgcc | 60 |
| cccgcggcgg ttcccggagc tcgtcccgga cgcgcgcccg ggcggcgggg gctcggcggc | 120 |
| caccgctgcc tcgggggagc gagggcggga gggtgtgtgt gcgcgctgtg agcaggggt | 180 |
| gccggcgggg ctgcagcgga ggcactttgg aagaatgact ctggagtcca tcatggcgtg | 240 |
| ctgcctgagc gaggaggcca aggaagcccg gcggatcaac gacgagatcg agcggcagct | 300 |
| ccgcagggac aagcgggacg cccgccggga gctcaagctg ctgctgctcg ggacaggaga | 360 |
| gagtggcaag agtacgttta tcaagcagat gagaatcatc catgggtcag atactctga | 420 |
| tgaagataaa aggggcttca ccaagctggt gtatcagaac atcttcacgg ccatgcaggc | 480 |
| catgatcaga gccatggaca cactcaagat cccatacaag tatgagcaca ataaggctca | 540 |
| tgcacaatta gttcgagaag ttgatgtgga gaaggtgtct gcttttgaga atccatatgt | 600 |

```
agatgcaata aagagtttat ggaatgatcc tggaatccag gaatgctatg atagacgacg    660
agaatatcaa ttatctgact ctaccaaata ctatcttaat gacttggacc gcgtagctga    720
ccctgcctac ctgcctacgc aacaagatgt gcttagagtt cgagtcccca ccacagggat    780
catcgaatac ccctttgact tacaaagtgt cattttcaga atggtcgatg taggggggcca   840 aaggtcagag agaagaaaat ggatacactg ctttgaaaat gtcacctcta tcatgtttct    900
agtagcgctt agtgaatatg atcaagttct cgtggagtca gacaatgaga accgaatgga    960
ggaaagcaag gctctcttta gaacaattat cacataccccc tggttccaga actcctcggt  1020
tattctgttc ttaaacaaga aagatcttct agaggagaaa atcatgtatt cccatctagt   1080
cgactacttc ccagaatatg atggacccca gagagatgcc caggcagccc gagaattcat   1140
tctgaagatg ttcgtggacc tgaacccaga cagtgacaaa attatctact cccacttcac   1200
gtgcgccaca gacaccgaga atatccgctt tgtctttgct gccgtcaagg acaccatcct   1260
ccagttgaac ctgaaggagt acaatctggt ctaattgtgc ctcctagaca cccgccctgc   1320
ccttccctgg tgggctattg aagatacaca agagggactg tatttctgtg gaaaacaatt   1380
tgcataatac taatttattg ccgtcctgga ctctgtgtga gcgtgtccac agagtttgta   1440
gtaaatatta tgatttatt taaactattc agaggaaaaa cagaggatgc tgaagtacag    1500
tcccagcaca tttcctctct atcttttttt taggcaaaac cttgtgactc agtgtatttt   1560
aaattctcag tcatgcactc acaaagataa gacttgtttc tttctgtctc tctctctttt   1620
tcttttctat ggagcaaaac aaagctgatt tcccttttttt cttccccccgc taattcatac 1680 ctccctcctg atgttttttcc caggttacaa tggcctttat cctagttcca ttcttggtca   1740 agttttctc tcaaatgata cagtcaggac acatcgttcg atttaagcca tcatcagctt    1800
aatttaagtt tgtagttttt gctgaaggat tatatgtatt aatacttacg gttttaaatg    1860
tgttgctttg gatacacaca tagttttcttt tttaatagaa tatactgtct tgtctcactt   1920
tggactggga cagtggatgc ccatctaaaa gttaagtgtc atttcttttta gatgtttacc   1980 ttcagcccata gcttgattgc tcagagaaat atgcagaagg caggatcaaa gacacacagg   2040 agtccttttct tttgaaatgc cacgtgccat tgtctttcct cccttctttg cttctttttc   2100
ttaccctctc tttcaattgc agatgccaaa aaagatgcca acagacacta cattaccctca  2160 atggctgcta cccagaacct ttttataggt tgttcttaat ttttttgttg ttgttgttca    2220
agcttttcct ttcttttttt tcttggtgtt tgggccacga ttttaaaatg acttttatta    2280
tgggtatgtg ttgccaaagc tggcttttg tcaaataaaa tgaatacgaa cttaaaaaat     2340
aaaagctggt atcttaaaat gtaagagagt aagactgtga agcctaaaat gactggctga    2400
gaatgaacca gaaatgccat ttgccaaaca gttgtaacta gaaatttgat tctcacggtc    2460
cattcttttc tttgtcctta agatgacatt gttagtgttc acgtcccatg ttcagtgtcc    2520
aaaccggcaa tgtaaaagt atcctgtgtg gtttaacagg aaatctgttt atgtctcttt     2580
atttgaaacc agttttactc tcagtggttc tttaagttca atgaagtctg ccaggaacat    2640
tggttggtag tattattccg cacacttttaa ttttccaaaat ctgaagttcc tgctagttta   2700
ccaccttcat gatcttcttg aactggtaac tgattaggtt gaacttatgg aagatttgtg    2760
gacttaactc aaaagtaacc tctcagtgtt ctatagaaca tgtatttgtg taactgaacc    2820
taccaggaga aatgttggga attctatatg tgcaatttttt caacaaatgc aaaaaaaata  2880
cagcacatgt attgacaagc ttctgtcaag cagcttgagt tgaaatttga tttaagaaaa    2940
```

```
taaatcatga ttgttcaaag ctgctgggac gttagaatta ggccatgata ctggtctcat    3000
tttaactaca gtggtatttg cactagtgt  aaacttccat ataaatcact cttttggaac    3060
aacaaagggg gagggagaaa aatcacggcc tgttaaatga gtaccaaagc cgcccaacag    3120
taatgagatg ttctcatcct tgattctccc agcctcaaac aacacagctt acttttttt    3180 tcccttgctc agaaagtacc tgtaatttaa caaacagact gcctgtaggt atagtgcaat    3240
tacaaatgct ctaatcattg tacatacatc tctcttgata ttgcagcatc catactggct    3300
ttgtaatcat taatttttg  gcagattgaa tgtgctgtat tgatatgtat ctatgtaatt    3360
gtattgtatg tctatagcta attcacgttt tgaataatgt tatttatt  acttttttaa    3420 gagaggagaa tgtaaatttg tcagtttatt tctgactagg gatattttct ttccatttag    3480
aaaagaagaa aaaaaaaaaa ccttactgtc atacagagcg gtactagcgt cgtgctgtat    3540
aaaatcattt gcacattcct gagtagaggt atactgatta taagacccaa aggtaatttc    3600
atagcaaaat acataaaatc agtcggagct tttatacaaa catggaaacc aactttgtag    3660 aactttgcc  atttgatcta ggattggaat atgagctttt atacaattca tattcttatt    3720
tggcaaatgc acagtttagt attacctctc tgatggcctt tactagaaag gcagttttag    3780
aagctattgt gatccactaa ggaaatgttt taacagctag agaccactgc ttgcctgaaa    3840
gggcgttctt aaatttggtg cagcaaaaaa aaaaaaaaa  aaaaaaaaaa ttaaacaaca    3900
acatttgaag gcctacagtg tgtatagaga aaacctcatc acaagatcat aagtgttaca    3960
gttttaggga atcaagatat tctatttaat agagctatag taaatgtagt caattaaacc    4020
tgatctcaaa gcttgaagaa gctgagcaaa cagggaaag  attgttatat ttgtctttat    4080
gaaattggga tggaatttgc tatgcagaat tgaggtttgt ggcttcgctg ttcctgtagg    4140
gtgcatgaca agatcccttc tcttgagaaa ggaaaaaatt gatcaccta  gcagcagtga    4200 tgcatagaaa cctaattta  gccacaccag tcaatcgaag ctaaaggatt ttctttttg    4260 tttcttcggg gttttattga aggggctagg ggcgggacgg gattctttc  agttttgtat    4320 aaaaacaaag tttactcatg ctttatatta tattgtgatt gcaagcgtta taagcgtgtg    4380
ccactggcct cctattgttg atgcttaggt aatggaggcc tgtggtgagt tttatggtga    4440
cttgggcatg tcttattcaa aaacaaaaac ataaaacaca gaaacctttc ttcagcatac    4500
caaggcaagc agccatttca tgactcactt aacacattgc agtgtaccag tttacagatg    4560 attttttccct ttttgcgtga catggcagtt ctaaccccca gagaattcct tatttgtaaa    4620
ttggaagttt ctactatgcc ttacagagct taaattcaga agtttgtgcc tcatatctga    4680
aacaaaggga aataacacac ccattcaaaa gtaaataaat ctcctagaag ttttgttttt    4740
taacatttcc atataaagag ctctgttgaa tgtcatgaat agactggaaa aaaaaatttt    4800
aagaacctgc atatgttgtt tactagcaga tgacaactac aaaaggaatc tgaagaacac    4860
gtaaaacttg ttttttttt  tttttggtag attaactagc aggcctattt taaaaaggta    4920
attcagctaa agggcaattt acttttttgt acttcagact atcttgattg tcaaagtgta    4980
cgaactgtaa ttttaaaatt tatactgcca catgattgta aattttagtt gtcttaagtt    5040
aggaattggt gaaaagctat ttatgctgga tttgggtcaa aatgacttat ttgcaaaaaa    5100
ataaataatg ggaagaaagg gctgtataat gaaatactgc aagactcaca tattggttgg    5160
aaatttccct caaatcacct accgattacc cttgatttcc ctttgttttc agtttctcaa    5220
aacgaatgaa atgaaatata gcagaatgtt aacccatata aaaataaagt gtacccaaat    5280
attgtaatgt atattgctgc tcttcttcaa attaaataag ggtttaaaac cacttaattg    5340
```

```
gtaatcaaca tctcaattga tacaaataag gtgtgcttgg tatacattaa tattttcttc    5400
caaagatata tctttggtta gaaacacaaa aaaataaaac tagtaatatt gtatgtttat    5460
ctatctctac atatttccag catatgtagc gttaatagat ctgtcctggt aactgtgtct    5520
ttgggatttc attttggttc catcaaatta ggaaaagaaa tggcttagtt gtatatgatt    5580
agctagagat ttttggagcc agacacctgc tgtttagtag ataacttagt acagaccta     5640 aacttgtcat ttgttttct cacagaatag ccatttcctg ctgtcttccc aatgatcact    5700 gcccttt caa taacactctt gcctctagaa tcatatgttc aaagtatgaa tacacaccta   5760
gcacatagta ggtgctcaaa tattaatttc ctccttgcct tccttatcta ccctgtgtcc    5820
tccatttccc cgtatgattc caacccaata tagcaaatga catttacatg ttatgaaaac    5880
atctattggg taaaatcaga tcttggataa agaaattctg acttttatat aagcttttgg    5940
tagacagaaa aaacagaaag gtattcgttg gtagaacatt tttaagttca ggaaagaaag    6000 ctgaataat actacgtaac tttgtccagg ttactttgac tgaaacacgt ttttggtgga    6060
tttcttttcc tcaaagaact ctctaaatgc aactccttgc tggattcctc acccatcatc    6120
ctgttggaaa cccttactag acctatgtat ttagggagtt ttgtcagaaa acattttaa     6180 cttgcagtat ttaaaagaat atttactgtt cctaaaatgt cattcaaatg catgtactgt    6240
ctattgtttg gggatgggaa ctagttttgc aaaaaacacc taatgttgta taataatgcc    6300
ccaatgatct tgctggttaa aaatacagta tttttggcca taa                      6343

<210> SEQ ID NO 3
<211> LENGTH: 119
<212> TYPE: PRT
<213> ORGANISM: Homo sapiens

<400> SEQUENCE: 3

Met Lys Ala Leu Ser Pro Val Arg Gly Cys Tyr Glu Ala Val Cys Cys
1               5                   10                  15

Leu Ser Glu Arg Ser Leu Ala Ile Ala Arg Gly Arg Gly Lys Gly Pro
            20                  25                  30

Ala Ala Glu Glu Pro Leu Ser Leu Leu Asp Asp Met Asn His Cys Tyr
        35                  40                  45

Ser Arg Leu Arg Glu Leu Val Pro Gly Val Pro Arg Gly Thr Gln Leu
    50                  55                  60

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
                85                  90                  95

Leu Pro Ile Gln Thr Ala Glu Leu Thr Pro Glu Leu Val Ile Ser Asn
            100                 105                 110

Asp Lys Arg Ser Phe Cys His
        115

<210> SEQ ID NO 4
<211> LENGTH: 1252
<212> TYPE: DNA
<213> ORGANISM: Homo sapiens

<400> SEQUENCE: 4
gatctggggt gctgccagga aaagcaaat tctggaagtt aatggttttg agtgattttt      60
aaatccttgc tggcggagag gcccgcctct ccccggtatc agcgcttcct cattctttga    120
```

```
atccgcggct ccgcggtctt cggcgtcaga ccagccggag gaagcctgtt tgcaatttaa      180
gcgggctgtg aacgcccagg gccggcgggg gcagggccga ggcgggccat tttgaataaa      240
gaggcgtgcc ttccaggcag gctctataag tgaccgccgc ggcgagcgtg cgcgcgttgc      300
aggtcactgt agcgggactt cttttggttt tctttctctt tggggcacct ctggactcac      360
tccccagcat gaaggcgctg agcccggtgc gcggctgcta cgaggcggtg tgctgcctgt      420
cggaacgcag tctggccatc gcccggggcc gagggaaggg cccggcagct gaggagccgc      480
tgagcttgct ggacgacatg aaccactgct actcccgcct gcgggaactg gtacccggag      540
tcccgagagg cactcagctt agccaggtgg aaatcctaca gcgcgtcatc gactacattc      600
tcgacctgca ggtagtcctg gccgagccag ccctggacc ccctgatggc ccccaccttc      660
ccatccagac agccgagctc actccggaac ttgtcatctc caacgacaaa aggagctttt      720
gccactgact cggccgtgtc ctgacacctc cagaacgcag gtgctggcgc ccgttctgcc      780
tgggaccccg ggaacctctc ctgccggaag ccggacggca gggatgggcc ccaacttcgc      840
cctgcccact tgacttcacc aaatcccttc ctggagacta aacctggtgc tcaggagcga      900
aggactgtga acttgtggcc tgaagagcca gagctagctc tggccaccag ctgggcgacg      960
tcaccctgct cccaccccac ccccaagttc taaggtctct tcagagcgtg gaggtgtgga     1020
aggagtggct gctctccaaa ctatgccaag gcggcggcag agctggtctt ctggtctcct     1080
tggagaaagg ttctgttgcc ctgatttatg aactctataa tagagtatat aggttttgta     1140
cctttttttac aggaaggtga ctttctgtaa caatgcgatg tatattaaac ttttttataaa   1200
agttaacatt ttgcataata aacgattttt aaacacttga aaaaaaaaaa aa             1252
```

<210> SEQ ID NO 5
<211> LENGTH: 199
<212> TYPE: PRT
<213> ORGANISM: Streptomyces alboniger

<400> SEQUENCE: 5

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

```
Thr Val Thr Ala Asp Val Glu Val Pro Glu Gly Pro Arg Thr Trp Cys
                180                 185                 190
Met Thr Arg Lys Pro Gly Ala
        195
```

<210> SEQ ID NO 6
<211> LENGTH: 435
<212> TYPE: PRT
<213> ORGANISM: Homo sapiens

<400> SEQUENCE: 6

```
Met Ala Ser Asn Ser Trp Asn Ala Ser Ser Pro Gly Glu Ala Arg
1               5                   10                  15
Glu Asp Gly Pro Glu Gly Leu Asp Lys Gly Leu Asp Asn Asp Ala Glu
                20                  25                  30
Gly Val Trp Ser Pro Asp Ile Glu Gln Ser Phe Gln Glu Ala Leu Ala
            35                  40                  45
Ile Tyr Pro Pro Cys Gly Arg Arg Lys Ile Ile Leu Ser Asp Glu Gly
        50                  55                  60
Lys Met Tyr Gly Arg Asn Glu Leu Ile Ala Arg Tyr Ile Lys Leu Arg
65                  70                  75                  80
Thr Gly Lys Thr Arg Thr Arg Lys Gln Val Ser Ser His Ile Gln Val
                85                  90                  95
Leu Ala Arg Lys Lys Val Arg Glu Tyr Gln Val Gly Ile Lys Ala Met
                100                 105                 110
Asn Leu Asp Gln Val Ser Lys Asp Lys Ala Leu Gln Ser Met Ala Ser
                115                 120                 125
Met Ser Ser Ala Gln Ile Val Ser Ala Ser Val Leu Gln Asn Lys Phe
        130                 135                 140
Ser Pro Pro Ser Pro Leu Pro Gln Ala Val Phe Ser Thr Ser Ser Arg
145                 150                 155                 160
Phe Trp Ser Ser Pro Pro Leu Leu Gly Gln Gln Pro Gly Pro Ser Gln
                165                 170                 175
Asp Ile Lys Pro Phe Ala Gln Pro Ala Tyr Pro Ile Gln Pro Pro Leu
                180                 185                 190
Pro Pro Thr Leu Ser Ser Tyr Glu Pro Leu Ala Pro Leu Pro Ser Ala
            195                 200                 205
Ala Ala Ser Val Pro Val Trp Gln Asp Arg Thr Ile Ala Ser Ser Arg
        210                 215                 220
Leu Arg Leu Leu Glu Tyr Ser Ala Phe Met Glu Val Gln Arg Asp Pro
225                 230                 235                 240
Asp Thr Tyr Ser Lys His Leu Phe Val His Ile Gly Gln Thr Asn Pro
                245                 250                 255
Ala Phe Ser Asp Pro Pro Leu Glu Ala Val Asp Val Arg Gln Ile Tyr
                260                 265                 270
Asp Lys Phe Pro Glu Lys Lys Gly Gly Leu Lys Glu Leu Tyr Glu Lys
            275                 280                 285
Gly Pro Pro Asn Ala Phe Phe Leu Val Lys Phe Trp Ala Asp Leu Asn
        290                 295                 300
Ser Thr Ile Gln Glu Gly Pro Gly Ala Phe Tyr Gly Val Ser Ser Gln
305                 310                 315                 320
Tyr Ser Ser Ala Asp Ser Met Thr Ile Ser Val Ser Thr Lys Val Cys
                325                 330                 335
Ser Phe Gly Lys Gln Val Val Glu Lys Val Glu Thr Glu Tyr Ala Arg
                340                 345                 350
```

```
Leu Glu Asn Gly Arg Phe Val Tyr Arg Ile His Arg Ser Pro Met Cys
        355                 360                 365

Glu Tyr Met Ile Asn Phe Ile His Lys Leu Lys His Leu Pro Glu Lys
370                 375                 380

Tyr Met Met Asn Ser Val Leu Glu Asn Phe Thr Ile Leu Gln Val Val
385                 390                 395                 400

Thr Ser Arg Asp Ser Gln Glu Thr Leu Leu Val Ile Ala Phe Val Phe
            405                 410                 415

Glu Val Ser Thr Ser Glu His Gly Ala Gln His His Val Tyr Lys Leu
            420                 425                 430

Val Lys Asp
        435

<210> SEQ ID NO 7
<211> LENGTH: 3023
<212> TYPE: DNA
<213> ORGANISM: Homo sapiens

<400> SEQUENCE: 7
tcctcaacac aaactttccg tcccgctcgc tccctcctcc gcgctcggcg cctcccgctc      60
cagcccggct cattccgcac attccggcca gcccctccc cacgaccccc cttccccggc     120
cccccttgcg gctccctcgg gccggcgga gcggcccggc cggagcgccc ccgcgagctc     180
ggaccaggct cagccgccca gtgggctcag gcccagagcc cagagcaacc agcacaatag     240
cgtccaacag ctggaacgcc agcagcagcc ccggggaggc ccggggaggat gggcccgagg     300 gcctggacaa ggggctggac aacgatgcgg agggcgtgtg gagcccggac atcgagcaga     360
gcttccagga ggccctggcc atctacccgc cctgcggccg gcggaagatc atcctgtcag     420
acgagggcaa gatgtacggc cgaaatgagt tgattgcacg ctatattaaa ctgaggacgg     480
ggaagactcg gacgagaaaa caggtgtcca gccacataca ggttctagct cggaagaagg     540
tgcgggagta ccaggttggc atcaaggcca tgaacctgga ccaggtctcc aaggacaaag     600
cccttcagag catggcgtcc atgtcctctg cccagatcgt ctctgccagt gtcctgcaga     660
acaagttcag cccaccttcc cctctgcccc aggccgtctt ctccacttcc tcgcggttct     720
ggagcagccc ccctctcctg ggacagcagc ctggaccctc tcaggacatc aagcccttg      780 cacagccagc ctaccccatc cagccgcccc tgccgccgac gctcagcagt tatgagcccc     840 tggcccccgct cccctcagct gctgcctctg tgcctgtgtg caggaccgt accattgcct     900 cctcccggct gcggctcctg gagtattcag ccttcatgga ggtgcagcga gaccctgaca     960
cgtacagcaa acacctgttt gtgcacatcg gcagcgaacaac cccgccttc tcagacccac    1020 ccctggagcc agtagatgtg cgccagatct atgacaaatt ccccgagaaa aagggaggat    1080
tgaaggagct ctatgagaag gggcccccta atgccttctt ccttgtcaag ttctgggccg    1140
acctcaacag caccatccag aggccccgg gagccttcta tgggtcagc tctcagtaca    1200 gctctgctga tagcatgacc atcagcgtct ccaccaaggt gtgctccttt ggcaaacagg    1260
tggtagagaa ggtgggagact gagtatgcca ggctggagaa cgggcgcttt gtgtaccgta    1320
tccaccgctc gcccatgtgc gagtacatga tcaacttcat ccacaagctg aagcacctgc    1380
ccgagaagta catgatgaac agcgtgctgg agaacttcac catcctgcag gtggtcacga    1440
gccgggactc ccaggagacc ctgcttgtca ttgcttttgt cttcgaagtc tccaccagtg    1500
agcacggggc ccagcaccat gtctacaagc tcgtcaaaga ctagggtgcc ctctgcgcct    1560
```

```
ccttaaggat gcagggtgag catctcctct ccacacctgc ctggcacccc tgggggggtc      1620
caggattgag gattcatcta cctgccaggc ctcaggccca ggacccagga ggcctcccca      1680
cctaccccag cacacacact ccctgccact gttctgcgct ttaattgtgg gagaagagag      1740
gagaggaggg ctcagcggtg gggcagcctg tccggggcgc tgacccacca tcaccctgct      1800
ctgcccagcc tcgcgtgacc tcagagaggt ggggataggg gacaccttca gcctccagca      1860
tgtgtggcca ctgtaccccc acccacccct gggggagcat gatgggcagg tgagggcagg      1920
atggagacca agggagtcag tgagcagagg ccctgggagt gtccggttgg ggttggactg      1980
aggacagagg ggcccacact tccttgcccc tttgtgtccc aggcctggtg cccagactcc      2040
ttgcatggct tgtgtggtcc tcagactccg cacagcgagc gtaggtctct gggtttcaga      2100
tgaagtgccc aggctccagg aagttgaggg acccacagga gaggtgggca gagctggagt      2160
tctcatccag ggctgcttgt ccccagagcc caggtttata ctacctccct ggggcggggg      2220
ctggccgcag ggtaggggag aggctctgca gtgtggagtg gagcctcatc gagggcgct      2280 gggttagggg agcacctgtt tcagactggg catgaagaag ggagcacagc agctactaga      2340
ccccattagc acctcattag cccacaagcc agccaggggc cccaggaaga tggggcaccc      2400
cccagcaccc tccagattga gagcaaggta gaggaaggag tcccagcctc tgggcagacc      2460
agaggcccag agggagagag tagcagaagg cttttgattt ttctcttgcc tgaggcttga      2520
atctgacaaa cccttggtgg gcactgctcc cttaggttct tccccacctc aatctacctg      2580
cctagagtag cagctcccag acccagttct gggactgaag gttaacccctt cacctgctgt      2640 ccccttcttaa cacccaggcc cccagagcca gctgggcctg tccagcagcc acctgtgggt      2700
atttatgagt ttcatatgaa gtactgtgcc ccttcccttc ctcatcccga ccctgcccga      2760
gcttcctgaa ggtcctcact gtttgcatat cgctcaggcc acctccaaac cccacctagg      2820
ttttataatg tatattatat attttttgt gtatttttaa aatccagctg tgatgggtta      2880
tatcataaat gcagcttggg gttggagcag gggccctcaa aggcccagct cctgctcaaa      2940
aaaaaaaaaa aaaaaaaatt aaagttattt gtttgtgggt cagtcatgta aaaaaaaaa      3000 aaaaaaaaaa aaaaaaaaaa aaa                                              3023
```

<210> SEQ ID NO 8
<211> LENGTH: 200
<212> TYPE: PRT
<213> ORGANISM: Homo sapiens

<400> SEQUENCE: 8

```
Met Ala Gln Ser Lys Leu Asp Cys Arg Ser Pro Val Gly Leu Asp Cys
1               5                   10                  15

Cys Asn Cys Cys Leu Asp Leu Ala His Arg Ser Gly Leu Gln Arg Gly
            20                  25                  30

Ser Ser Gly Glu Asn Asn Asn Pro Gly Ser Pro Thr Val Ser Asn Phe
        35                  40                  45

Arg Gln Leu Gln Glu Lys Leu Val Phe Glu Asn Leu Asn Thr Asp Lys
    50                  55                  60

Leu Asn Ser Ile Met Arg Gln Asp Ser Leu Glu Pro Val Leu Arg Asp
65                  70                  75                  80

Pro Cys Tyr Leu Ile Asn Glu Gly Ile Cys Asn Arg Asn Ile Asp Gln
                85                  90                  95

Thr Met Leu Ser Ile Leu Leu Phe Phe His Ser Ala Ser Gly Ala Ser
            100                 105                 110
```

| Val | Val | Ala | Ile | Asp | Asn | Lys | Ile | Glu | Gln | Ala | Met | Asp | Leu | Val | Lys |
| | 115 | | | | | 120 | | | | | 125 | | | | |

| Asn | His | Leu | Met | Tyr | Ala | Val | Arg | Glu | Glu | Val | Glu | Ile | Leu | Lys | Glu |
| 130 | | | | | 135 | | | | | 140 | | | | | |

| Gln | Ile | Arg | Glu | Leu | Val | Glu | Lys | Asn | Ser | Gln | Leu | Glu | Arg | Glu | Asn |
| 145 | | | | | 150 | | | | | 155 | | | | | 160 |

| Thr | Leu | Leu | Lys | Thr | Leu | Ala | Ser | Pro | Glu | Gln | Leu | Glu | Lys | Phe | Gln |
| | | | | 165 | | | | | 170 | | | | | 175 | |

| Ser | Cys | Leu | Ser | Pro | Glu | Glu | Pro | Ala | Pro | Glu | Ser | Pro | Gln | Val | Pro |
| | | | 180 | | | | | 185 | | | | | 190 | | |

| Glu | Ala | Pro | Gly | Gly | Ser | Ala | Val |
| | | | 195 | | | | 200 |

```
<210> SEQ ID NO 9
<211> LENGTH: 2223
<212> TYPE: DNA
<213> ORGANISM: Homo sapiens

<400> SEQUENCE: 9
gtcatatccc agtgctgact cccgggcgtg cagaccgcta actagctcac tcgctctcag      60
ctcctgccac cgctcagccg tcacagccca ggggagcccg agagcctgag agcctgcaaa     120
ccggggaggg agggagcaaa ggagggaggg agcaagggcg cgccctggct ctccctctgc     180
cctgctgccc gccttcctg cctccacagg caccctggag tcccctcagg ccagctcggt      240
gggcgcgcac ctgccagccg cccctgacct cgcaggccag gcgacctccg agcctgagaa     300
gatggcccag tccaagctcg attgccgctc acctgtcggc ctcgactgct gcaactgctg     360
cctggacctg gccatcggag tgggctccca gcgaggcagc agcggggaga caacaacccc     420
gggcagccct acagtgagca actttcggca gctgcaggaa aagctggtct ttgagaacct     480
caataccgac aagctcaaca gcataatgcg gcaggattcg ctagagccgg tgctgcggga     540
ccctgctac ctgatcaacg agggcatctg caaccgcaac atcgaccaga ccatgctctc      600
catcctgctc ttcttccaca gtgcctccgg agccagcgtg gtggccatag acaacaagat     660
cgaacaggcc atggatctgg tgaagaatca tctgatgtat gctgtgagag aggaggtgga     720
gatcctgaag gagcagatcc gagagctggt ggagaagaac tcccagctag agcgtgagaa     780
caccctgttg aagaccctgg caagcccaga gcagctggaa agttccagt cctgtctgag      840
ccctgaagag ccagctcccg aatccccaca agtgcccgag gcccctggtg gttctgcggt     900
gtaagtggct ctgtcctcag ggtgggcaga gccactaaac ttgttttacc tagttctttc     960
cagtttgttt ttggctcccc aagcatcatc tcacgaggag aactttacac ctagcacagc    1020
tggtgccaag agatgtccta aggacatggc cacctgggtc cactccagcg acagacccct    1080
gacaagagca ggtctctgga ggctgagttg catggggcct agtaacacca agccagtgag    1140
cctctaatgc tactgcgccc tggggctcc cagggcctgg gcaacttagc tgcaactggc     1200
aaaggagaag ggtagtttga ggtgtgacac cagtttgctc cagaaagttt aagggtctg    1260
tttctcatct ccatggacat cttcaacagc ttcacctgac aacgactgtt cctatgaaga    1320
agccacttgt gttttaagca gaggcaacct ctctcttctc ctctgtttcg tgaaggcagg    1380
ggacacagat gggagagatt gagccaagtc agccttctgt tggttaatat ggtataatgc    1440
atggctttgt gcacagccca gtgtgggatt acagctttgg gatgaccgct tacaaagttc    1500
tgtttggtta gtattggcat agttttcta tatagccata aatgcgtata tacccata       1560
gggctagatc tgtatcttag tgtagcgatg tatacatata cacatccacc tacatgttga    1620
```

```
agggcctaac cagccttggg agtattgact ggtcccttac ctcttatggc taagtctttg    1680
actgtgttca tttaccaagt tgacccagtt tgtcttttag gttaagtaag actcgagagt    1740
aaaggcaagg agggggggcca gcctctgaat gcggccacgg atgccttgct gctgcaaccc    1800
tttccccagc tgtccactga aacgtgaagt cctgttttga atgccaaacc caccattcac    1860
tggtgctgac tacatagaat ggggttgaga gaagatcagt ttgggcttca cagtgtcatt    1920
tgaaaacgtt ttttgttttg ttttgtaatt attgtgaaaa actttcaagt gaacagaagg    1980
atggtgtcct actgtggatg agggatgaac aaggggatgg ctttgatcca atggagcctg    2040
ggaggtgtgc ccagaaagct tgtctgtagc gggttttgtg agagtgaaca ctttccactt    2100
tttgacacct tatcctgatg tatggttcca ggatttggat tttgattttc caaatgtagc    2160
ttgaaatttc aataaacttt gctctgtttt tctaaaaata aaaaaaaaaa aaaaaaaaa     2220 aaa                                                                  2223
```

<210> SEQ ID NO 10
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(18)
<223> OTHER INFORMATION: a, c, t, g, unknown or other

<400> SEQUENCE: 10

```
nnnnnnnnnn nnnnnnnnga gctctctggc taactagaga acccactgct tactggctta      60
tcgaaattaa tacgactcac tatagggaga cccaagctgg ctagcgttta aacttaagct     120
tggtaccacc atgactctgg agtccatcat ggcgtgctgc ctgagcgagg aggccaagga     180
agcccggcgg atcaacgacg agatcgagcg gcagctccgc agggacaagc gggacgcccg     240
ccgggagctc aagctgctgc tgctcgggac aggagagagt ggcaagagta cgtttatcaa     300
gcagatgaga atcatccatg ggtcaggata ctctgatgaa gataaagggg gcttcaccaa     360
gctggtgtat cagaacatct tcacggccat gcaggccatg atcagagcca tggacacact     420
caagatccca tacaagtatg agcacaataa ggctcatgca caattagttc gagaagttga     480
tgtggagaag gtgtctgctt ttgagaatcc atatgtagat gcaataaaga gtttatggaa     540
tgatcctgga atccaggaat gctatgatag acgacgagaa tatcaattat ctgactctac     600
caaatactat cttaatgact tggaccgcgt agctgaccct gcctacctgc ctacgcaaca     660
agatgtgctt agagttcgag tccccaccac agggatcatc gaataccccct ttgacttaca     720 aagtgtcatt ttcagaatgg tcgatgtagg gggccaaagg tcagagagaa gaaaatggat     780
acactgcttt gaaaatgtca cctctatcat gtttctagta gcgcttagtg aatatgatca     840
agttctcgtg gagtcagaca atgagaaccg aatggaggaa agcaaggctc tctttagaac     900
aattatcaca taccctggt tccagaactc ctcggttatt ctgttcttaa acaagaaaga     960
tcttctagag gagaaaatca tgtattccca tctagtcgac tacttcccag aatatgatgg    1020
accccagaga gatgcccagg cagcccgaga                                      1050
```

<210> SEQ ID NO 11
<211> LENGTH: 1050
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<221> NAME/KEY: modified_base
<222> LOCATION: (1037)..(1037)
<223> OTHER INFORMATION: a, c, t, g, unknown or other
<220> FEATURE:
<221> NAME/KEY: modified_base
<222> LOCATION: (1039)..(1050)
<223> OTHER INFORMATION: a, c, t, g, unknown or other

<400> SEQUENCE: 11
ggcggatcaa cgacgagatc gagcggcagc tccgcaggga caagcgggac gcccgccggg     60
agctcaagct gctgctgctc gggacaggag agagtggcaa gagtacgttt atcaagcaga    120
tgagaatcat ccatgggtca ggatactctg atgaagataa aggggcttc accaagctgg    180 tgtatcagaa catcttcacg gccatgcagg ccatgatcag agccatggac acactcaaga    240
tcccatacaa gtatgagcac aataaggctc atgcacaatt agttcgagaa gttgatgtgg    300
agaaggtgtc tgcttttgag aatccatatg tagatgcaat aaagagttta tggaatgatc    360
ctggaatcca ggaatgctat gatagacgac gagaatatca attatctgac tctaccaaat    420
actatcttaa tgcttggac cgcgtagctg accctgccta cctgcctacg caacaagatg    480
tgcttagagt tcgagtcccc accacaggga tcatcgaata ccccttgac ttacaaagtg    540 tcattttcag aatggtcgat gtaggggcc aaaggtcaga gagaagaaaa tggatacact    600
gctttgaaaa tgtcacctct atcatgtttc tagtagcgct tagtgaatat gatcaagttc    660
tcgtggagtc agacaatgag aaccgaatgg aggaaagcaa ggctctcttt agaacaatta    720
tcacataccc ctggttccag aactcctcgg ttattctgtt cttaaacaag aaagatcttc    780
tagaggagaa aatcatgtat tcccatctag tcgactactt cccagaatat gatggaccc    840 agagagatgc ccaggcagcc cgagaattca ttctgaagat gttcgtggac ctgaacccag    900
acagtgacaa aattatctac tcccacttca cgtgcgccac agacaccgag aatatccgct    960
ttgtctttgc tgccgtcaag gacaccatcc tccagttgaa cctgaaggag tacaatctgg   1020
tctaactcga gtctagngnn nnnnnnnnnn                                    1050

<210> SEQ ID NO 12
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (17)..(19)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other

<400> SEQUENCE: 12
nnnnnnnnnn nnncttnnnc ttggtaccnc catgactctg gagtccatca tggcgtgctg     60
cctgagcgag gaggccaagg aagcccggcg gatcaacgac gagatcgagc ggcagctccg    120
cagggacaag cgggacgccc gccgggagct caagctgctg ctgctcggga caggagagag    180
```

| | | |
|---|---|---|
| tggcaagagt acgtttatca agcagatgag aatcatccat gggtcaggat actctgatga | 240 |
| agataaaagg ggcttcacca agctggtgta tcagaacatc ttcacggcca tgcaggccat | 300 |
| gatcagagcc atggacacac tcaagatccc atacaagtat gagcacaata aggctcatgc | 360 |
| acaattagtt cgagaagttg atgtggagaa ggtgtctgct tttgagaatc catatgtaga | 420 |
| tgcaataaag agtttatgga atgatcctgg aatccaggaa tgctatgata gacgacgaga | 480 |
| atatcaatta tctgactcta ccaaatacta tcttaatgac ttggaccgcg tagctgaccc | 540 |
| tgcctacctg cctacgcaac aagatgtgct tagagttcaa gtccccacca cagggatcat | 600 |
| cgaatacccc tttgacttac aaagtgtcat tttcagaatg gtcgatgtag ggggccaaag | 660 |
| gtcagagaga agaaaatgga tacactgctt tgaaaatgtc acctctatca tgtttctagt | 720 |
| agcgcttagt gaatatgatc aagttctcgt ggagtcagac aatgagaacc gaatggagga | 780 |
| aagcaaggct ctctttagaa caattatcac ataccctgg ttccagaact cctcggttat | 840 |
| tctgttctta aacaagaaag atcttctaga ggagaaaatc atgtattccc atctagtcga | 900 |
| ctacttccca gaatatgatg accccagag agatgcccag gcagcccgag aattcattct | 960 |
| gaagatgttc gtggacctga acccagacag tgacaaaatt atctactccc acttcacgtg | 1020 |
| cgccacagac accgagaata tccgctttgt | 1050 |

<210> SEQ ID NO 13
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1023)..(1024)
<223> OTHER INFORMATION: a, c, t, g, unknown or other
<220> FEATURE:
<221> NAME/KEY: modified_base
<222> LOCATION: (1027)..(1049)
<223> OTHER INFORMATION: a, c, t, g, unknown or other

<400> SEQUENCE: 13

| | |
|---|---|
| gatcaacgac gagatcgagc ggcagctccg cagggacaag cgggacgccc gccgggagct | 60 |
| caagctgctg ctgctcggga caggagagag tggcaagagt acgtttatca agcagatgag | 120 |
| aatcatccat gggtcaggat actctgatga agataaaagg ggcttcacca agctggtgta | 180 |
| tcagaacatc ttcacggcca tgcaggccat gatcagagcc atggacacac tcaagatccc | 240 |
| atacaagtat gagcacaata aggctcatgc acaattagtt cgagaagttg atgtggagaa | 300 |
| ggtgtctgct tttgagaatc catatgtaga tgcaataaag agtttatgga atgatcctgg | 360 |
| aatccaggaa tgctatgata gacgacgaga atatcaatta tctgactcta ccaaatacta | 420 |
| tcttaatgac ttggaccgcg tagctgaccc tgcctacctg cctacgcaac aagatgtgct | 480 |
| tagagttcaa gtccccacca cagggatcat cgaatacccc tttgacttac aaagtgtcat | 540 |
| tttcagaatg gtcgatgtag ggggccaaag gtcagagaga agaaaatgga tacactgctt | 600 |
| tgaaaatgtc acctctatca tgtttctagt agcgcttagt gaatatgatc aagttctcgt | 660 |
| ggagtcagac aatgagaacc gaatggagga aagcaaggct ctctttagaa caattatcac | 720 |
| ataccctgg ttccagaact cctcggttat tctgttctta aacaagaaag atcttctaga | 780 |
| ggagaaaatc atgtattccc atctagtcga ctacttccca gaatatgatg accccagag | 840 |
| agatgcccag gcagcccgag aattcattct gaagatgttc gtggacctga acccagacag | 900 |

```
tgacaaaatt atctactccc acttcacgtg cgccacagac accgagaata tccgctttgt    960
ctttgctgcc gtcaaggaca ccatcctcca gttgaacctg aaggagtaca atctggtcta   1020
acnngannnn nnnnnnnnnn nnnnnnnnnc                                    1050
```

```
<210> SEQ ID NO 14
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(19)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other

<400> SEQUENCE: 14
nnnnnnnnnn nnnnnnnnna nctctctggc tanctagaga acccactgct tactggctta     60
tcgaaattaa tacgactcac tatagggaga cccaagctgg ctagcgttta aacttaagct    120
tggtaccacc atgactctgg agtccatcat ggcgtgctgc ctgagcgagg aggccaagga    180
agcccggcgg atcaacgacg agatcgagcg gcagctccgc agggacaagc gggacgcccg    240
ccgggagctc aagctgctgc tgctcgggac aggagagagt ggcaagagta cgtttatcaa    300
gcagatgaga atcatccatg ggtcaggata ctctgatgaa gataaaaggg gcttcaccaa    360
gctggtgtat cagaacatct tcacggccat gcaggccatg atcagagcca tggacacact    420
caagatccca tacaagtatg agcacaataa ggctcatgca caattagttc gagaagttga    480
tgtggagaag gtgtctgctt ttgagaatcc atatgtagat gcaataaaga gtttatggaa    540
tgatcctgga atccaggaat gctatgatag acgacgagaa tatcaattat ctgactctac    600
caaatactat cttaatgact tggaccgcgt agctgaccct gcctacctgc ctacgcaaca    660
agatgtgctt agagttcgag tccccaccac agggatcatc gaatacccct ttgacttaca    720
aagtgtcatt ttcagaatgg tcgatgtagg gggcctaagg tcagagagaa gaaaatggat    780
acactgcttt gaaaatgtca cctctatcat gtttctagta gcgcttagtg aatatgatca    840
agttctcgtg gagtcagaca atgagaaccg aatggaggaa agcaaggctc tctttagaac    900
aattatcaca taccccctggt tccagaactc ctcggttatt ctgttcttaa acaagaaaga    960
tcttctagag gagaaaatca tgtattccca tctagtcgac tacttcccag aatatgatgg   1020
accccagaga gatgcccagg cagcccgaga                                    1050
```

```
<210> SEQ ID NO 15
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1018)..(1018)
<223> OTHER INFORMATION: a, c, t, g, unknown or other
<220> FEATURE:
<221> NAME/KEY: modified_base
```

```
<222> LOCATION: (1037)..(1037)
<223> OTHER INFORMATION: a, c, t, g, unknown or other
<220> FEATURE:
<221> NAME/KEY: modified_base
<222> LOCATION: (1039)..(1040)
<223> OTHER INFORMATION: a, c, t, g, unknown or other
<220> FEATURE:
<221> NAME/KEY: modified_base
<222> LOCATION: (1043)..(1050)
<223> OTHER INFORMATION: a, c, t, g, unknown or other

<400> SEQUENCE: 15
ggcggatcaa cgacgagatc gagcggcagc tccgcaggga caagcgggac gcccgccggg      60
agctcaagct gctgctgctc gggacaggag agagtggcaa gagtacgttt atcaagcaga     120
tgagaatcat ccatgggtca ggatactctg atgaagataa aggggcttc accaagctgg      180
tgtatcagaa catcttcacg gccatgcagg ccatgatcag agccatggac acactcaaga     240
tcccatacaa gtatgagcac aataaggctc atgcacaatt agttcgagaa gttgatgtgg     300
agaaggtgtc tgcttttgag aatccatatg tagatgcaat aaagagttta tggaatgatc     360
ctggaatcca ggaatgctat gatagacgac gagaatatca attatctgac tctaccaaat     420
actatcttaa tgacttggac cgcgtagctg accctgccta cctgcctacg caacaagatg     480
tgcttagagt tcgagtcccc accacaggga tcatcgaata ccccttgac ttacaaagtg      540
tcattttcag aatggtcgat gtaggggggcc taaggtcaga gagaagaaaa tggatacact    600
gctttgaaaa tgtcacctct atcatgtttc tagtagcgct tagtgaatat gatcaagttc     660
tcgtggagtc agacaatgag aaccgaatgg aggaaagcaa ggctctcttt agaacaatta     720
tcacataccc ctggttccag aactcctcgg ttattctgtt cttaaacaag aaagatcttc     780
tagaggagaa aatcatgtat tcccatctag tcgactactt cccagaatat gatggacccc     840
agagagatgc ccaggcagcc cgagaattca ttctgaagat gttcgtggac ctgaacccag     900
acagtgacaa aattatctac tcccacttca cgtgcgccac agacaccgag aatatccgct     960
tgtctttgc tgccgtcaag gacaccatcc tccagttgaa cctgaaggag tacaatcngg    1020
tctaactcga gtctagngnn ccnnnnnnnn                                     1050

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aggtcactgt agcggacttc                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttcatgctg gggagtgagt                                                  20

<210> SEQ ID NO 18
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 18
tctgtttcgt gaaggcaggg                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtaatccca cactgggctg                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttgtgtaccg tatccaccgc                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttctccagca cgctgttcat                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcaccatgtc ctggatgtca                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctgctggaa aacacacagc                                              20

<210> SEQ ID NO 24
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
tccaactttg actgcgggtc                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acatctgccc gttctctgat                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atggaaatcc aggcagccaa                                                    20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgtccataac tggagtaacc gc                                                 22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttgtgcttt ggggagcaga                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctaaggctt ccttcagcca                                                    20
```